(12) United States Patent
Terasaka et al.

(10) Patent No.: US 6,596,738 B1
(45) Date of Patent: Jul. 22, 2003

(54) HETEROCYCLIC COMPOUND, COMPOSITION AND METHOD FOR INHIBITING ADENOSINE DEAMINASE

(75) Inventors: Tadashi Terasaka, Ikeda (JP); Nobuo Seki, Takarazuka (JP); Kiyoshi Tsuji, Kishiwada (JP); Isao Nakanishi, Tenri (JP); Takayoshi Kinoshita, Tsukuba (JP); Katsuya Nakamura, Takatsuki (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/926,134

(22) PCT Filed: Mar. 3, 2000

(86) PCT No.: PCT/JP00/01316

§ 371 (c)(1),
(2), (4) Date: Sep. 7, 2001

(87) PCT Pub. No.: WO00/55155

PCT Pub. Date: Sep. 21, 2000

(30) Foreign Application Priority Data

Mar. 15, 1999 (AU) .................................. PP9212

(51) Int. Cl.[7] .................. A61K 31/4164; C07D 403/06; C07D 403/14

(52) U.S. Cl. .................. 514/337; 514/367; 514/397; 514/400; 546/14; 546/274.7; 548/159; 548/171; 548/305.4; 548/311.7; 548/312.1; 548/333.5

(58) Field of Search ................ 546/14, 274.7; 548/159, 171, 305.4, 311.7, 312.1, 333.5; 514/337, 367, 397, 400

(56) References Cited

U.S. PATENT DOCUMENTS

| | | | |
|---|---|---|---|
| 4,243,405 A | * | 1/1981 | Balasubramanyan et al. ............. 504/181 |
| 4,603,140 A | * | 7/1986 | Reiser et al. ............... 514/383 |
| 6,359,145 B1 | | 3/2002 | Terasaka et al. ......... 548/333.5 |

FOREIGN PATENT DOCUMENTS

| | | |
|---|---|---|
| DE | 31 39 250 | 4/1983 |
| DE | 32 24 129 | 12/1983 |
| DE | 32 34 627 | 3/1984 |
| DE | 33 21 422 | 12/1984 |
| DE | 34 16 444 | 11/1985 |
| EP | 56089 | * 7/1982 |
| GB | 1555576 | * 11/1979 |
| GB | 2 050 334 | 1/1981 |
| JP | 55-94384 | * 7/1980 |
| WO | WO 97/28803 | 8/1997 |
| WO | WO 98/02166 | 1/1998 |

OTHER PUBLICATIONS

Montignoul et al., J. Heterocyclic Chem., 1984, 21(5), 1509–1519.*

Yong–Zhong Zhao, et al., J. Med. Chem., vol. 40, No. 25, pp. 4006–4012, "Screening Solution–Phase Combinatorial Libraries Using Pulsed Ultrafiltration/Electrospray Mass Spectrometry", 1997.

M. Curtis, et al., Chemical Abstracts, vol. 129, No. 19, AN 129:245403u, Nov. 11, 1998, "Adenosine Deaminase Inhibitors. Synthesis and Biological Evaluation of Aralkyladenines (ARADS)", 1998.

P. Cozzi, et al., J. Med. Chem., vol. 37, No. 21, pp. 3588–3604, "Agents Combining Thromboxane Receptor Antagonism with Thromboxane Synthase Inhibition: [[[2(1H–Imidazol–1–yl) Ethylidene]Amino]Oxy]Alkanoic Acids", 1994.

(List continued on next page.)

*Primary Examiner*—Fiona T. Powers
(74) *Attorney, Agent, or Firm*—Oblon, Spivak, McClelland, Maier & Neustadt, P.C.

(57) ABSTRACT

Heterocyclic compounds of the following formula:

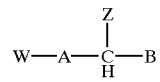

wherein
B is

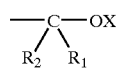

[wherein $R_1$ is hydrogen or lower alkyl;
$R_2$ is hydrogen or lower alkyl; and
X is hydrogen or hydroxy protective group], lower alkanoyl or hydroxyimino(lower)alkyl A is lower alkylene;

W is heterocyclic or carbocyclic group, each of which may have one or more substituent(s);

Z is heterocyclic group selected from the group consisting of imidazolyl, triazolyl, imidazopyridyl and adenyl, each of which may have one or more substituent(s);

or a salt thereof, provided that when W is aryl which may have one or more substituent(s), then (i) Z is triazolyl, imidazopyridyl or adenyl, each of which may have one or more substituent(s); (ii) Z is imidazolyl which may have one or more substituent(s) and B is lower alkanoyl or hydroxyimino(lower)alkyl; or (iii) Z is imidazolyl which may have one or more substituent(s) and $R_1$ and $R_2$ are both lower alkyl.

or pharmaceutically acceptable salts thereof, which are useful as a medicament.

27 Claims, No Drawings

H. Zheng, et al., Chemical Abstracts, vol.125, No. 7, AN 125:86571w, Aug. 12, 1996, "Synthesis and Biological Activities of Diclobutrazol", 1995.

L. Liao, et al., Chemical Abstracts, vol. 110, No. 23, AN 110:212710w, Jun. 5, 1989, "Synthesis of 1–Substituted 1–(1,2,4–Triazol–1–yl)–3,3–Dimethylbutane–2–Ones", 1988.

* cited by examiner

# HETEROCYCLIC COMPOUND, COMPOSITION AND METHOD FOR INHIBITING ADENOSINE DEAMINASE This application is a 371 of PCT/JP00/01316 filed Mar. 3, 2000.

TECHNICAL FIELD

This invention relates to new heterocyclic compounds having pharmacological activity, to processes for their production and to a pharmaceutical composition containing the same.

BACKGROUND ART

Some imidazole derivatives, which have inhibiting activity to adenosine deaminase (hereinafter described as ADA) are known, for example, by Drug Development Research 28, p253–258 (1993).

DISCLOSURE OF INVENTION

This invention relates to novel heterocyclic compounds which have pharmacological activity such as ADA inhibiting activity, to processes for their production, to a pharmaceutical composition containing the same and to a use thereof.

Accordingly, one object of this invention is to provide the novel heterocyclic compounds which have an ADA inhibiting activity.

Another object of this invention is to provide processes for their production of the new heterocyclic compounds.

A further object of this invention is to provide a pharmaceutical composition containing, as active ingredient, the new heterocyclic compounds.

Still further object of this invention is to provide a use of the new heterocyclic compounds for manufacturing a medicament for treating or preventing various diseases.

The new heterocyclic compounds of this invention can be represented by the following general formula (I):

$$W-A-\underset{H}{\overset{Z}{\underset{|}{C}}}-B \quad [I]$$

wherein
B is

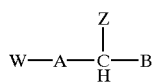

[wherein $R_1$ is hydrogen or lower alkyl;
$R_2$ is hydrogen or lower alkyl; and
X is hydrogen or hydroxy protective groups], lower alkanoyl or hydroxyimino(lower)alkyl;
A is lower alkylene;
W is heterocyclic or carbocyclic group, each of which may have one or more substituent(s);
Z is heterocyclic group selected from the group consisting of imidazolyl, triazolyl, imidazopyridyl and adenyl, each of which may have one or more substituent(s);
or a salt thereof,
provided that when W is aryl which may have one or more substituent(s), then (i) Z is triazolyl, imidazopyridyl or adenyl, each of which may have one or more substituent(s); (ii) Z is imidazolyl which may have one or more substituent(s) and B is lower alkanoyl or hydroxyimino(lower)alkyl; or (iii) Z is imidazolyl which may have one or more substituent(s) and $R_1$ and $R_2$ are both lower alkyl.

The compounds of formula (I) may contain one or more asymmetric centers and thus they can exist as syn- or anti-isomers. In each instance, the invention includes both mixtures and separate individual isomers.

The compounds of the formula (I) may exist in tautomeric forms and the invention includes both mixtures and separate individual tautomers.

The compounds of the formula (I) and a salt thereof can be in a form of solvate, which is included within the scope of the present invention. The solvate preferably includes a hydrate and an ethanolate.

Also included in the scope of this invention are radiolabelled derivatives of the compounds of formula (I) which are suitable for biological studies.

According to the present invention, the object compound (I) or a salt thereof can be prepared by the processes which are illustrated in the following scheme.

Process 1

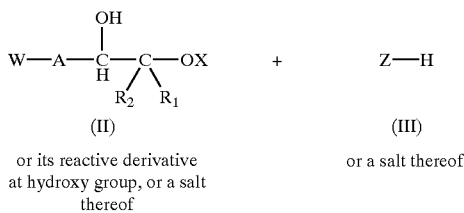

or its reactive derivative at hydroxy group, or a salt thereof or a salt thereof

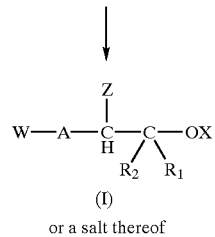

(I)
or a salt thereof

Process 2

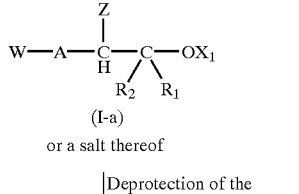

(I-a)
or a salt thereof

Deprotection of the hydroxy protective group

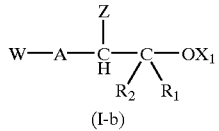

(I-b)
or a salt thereof

Process 3

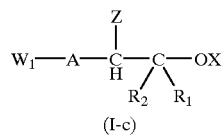
(I-c)
or a salt thereof

↓ reduction

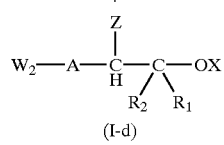
(I-d)
or a salt thereof

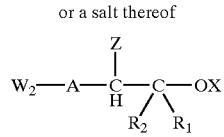
(I-d)
or a salt thereof

Process 4

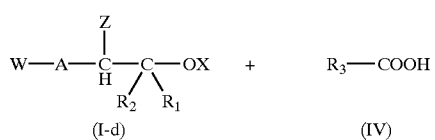
(I-d)                    (IV)
or its reactive derivative    or its reactive derivative
at the amino group,           at the carboxy group,
or a salt thereof             or a salt thereof

↓

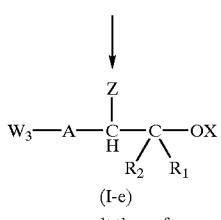
(I-e)
or a salt thereof

Process 5

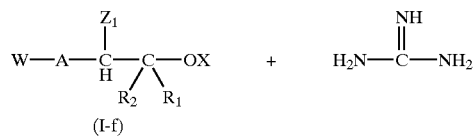
(I-f)
or its reactive derivative               or a salt thereof
at the carboxy group,
or a salt thereof

↓

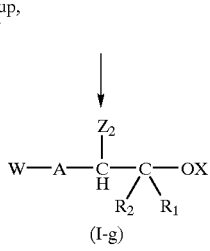
(I-g)
or a salt thereof

Process 6

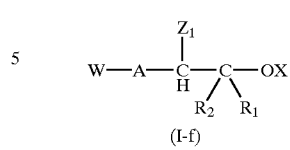
(I-f)
or its reactive derivative
at the carboxy group,
or a salt thereof ↓ amidation

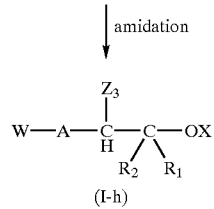
(I-h)
or a salt thereof

Process 7

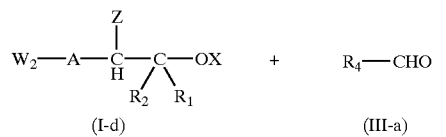
(I-d)                        (III-a)
or its reactive derivative       or a salt thereof
at the amino group,
or a salt thereof

↓

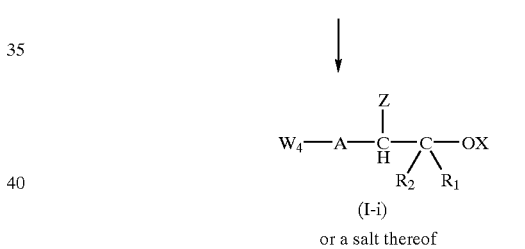
(I-i)
or a salt thereof

Process 8

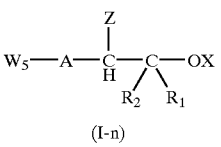
(I-n)
or a salt thereof

↓ ← deprotection of the hydroxy protective group

↓ ← + $R_5$—Y  or  $R_6$—$OR_7$
      (III-b)         (III-c)

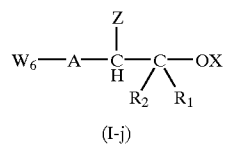
(I-j)
or a salt thereof

Process 9

W—A—CH(R₉)—C(R₈)(Z)—OH (I-o)
or reactive derivatives
at the hydroxy group,
or a salt thereof ↓ oxidation

W—A—CH(R₉)—C(Z)=O (I-k)
or a salt thereof

Process 10

W—A—CH(R₉)—C(Z)=O + NH₂OH or a salt thereof (I-k)
or a salt thereof

↓

W—A—CH(R₉)—C(Z)=NOH (I-l)
or a salt thereof

Process 11

W—A—CH(R₉)—C(Z)=O + R₁₀—Y (I-k)
or a salt thereof (III-d)
or a salt thereof

↓

W—A—CH(R₉)—C(R₁₀)(Z)—OH (I-m)
or a salt thereof wherein A, R₁, R₂, W, X and Z are each as defined above, R₃ is lower alkyl, optionally substituted ar(lower)alkyl, ar(lower)alkylamino, heterocyclic(lower)alkyl or heterocyclicthio(lower)alkyl, each of which may have one or more substituent(s), W₁ is heterocyclic group or carbocyclic group, each of which has nitro, W₂ is heterocyclic group or carbocyclic group, each of which has amino, W₃ is heterocyclic group or carbocyclic group, each of which has a group of the following formula:

—NH—C(O)—R₃ (R₃ is as defined above),

X₁ is hydroxy protective group,

Z₁ is imidazolyl, triazolyl, imidazopyridyl or adenyl, each of which has carboxy, Z₂ is imidazolyl, triazolyl, imidazopyridyl or adenyl, each of which has guanidinocarbonyl, Z₃ is imidazolyl, triazolyl, imidazopyridyl or adenyl, each of which has carbamoyl.

R₄ is lower alkyl, carbocyclic(lower)alkyl or heterocyclic(lower)alkyl,

W₄ is carbocyclic or heterocyclic group, each of which has lower alkylamino, carbocyclic(lower)alkylamino or heterocyclic(lower)alkylamino, W₅ is carbocyclic or heterocyclic group, each of which has a hydroxy protective group, R₅ and R₆ are lower alkyl, heterocyclic(lower)alkyl or carbocyclic(lower)alkyl, R₇ is hydrogen or methanesulfonyl, W₆ is heterocyclic or carbocyclic group, each of which has OR₅ or OR₆ [wherein R₅ and R₆ are as defined above].

R₈ is hydrogen,

R₉ is lower alkyl,

R₁₀ is lower alkyl, and

Y is halogen.

The starting compound (II), wherein B is

—C(R₁)(R₂)—OX, can be prepared by the following processes.

Process (A)

HO—A—[acetonide-protected diol with R₁, R₂] + W—H (V)
or its reactive derivative
at hydroxy group,
or a salt thereof (Vi)
or a salt thereof

↓

W—A—[acetonide-protected diol with R₁, R₂]

(V)
or a salt thereof

↓ deprotection of the hydroxy protective group

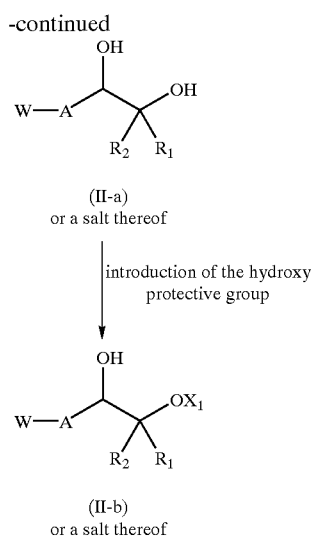

(II-a)
or a salt thereof

↓ introduction of the hydroxy protective group (II-b)
or a salt thereof wherein A, $R_1$, $R_2$, W and $X_1$ are each as defined above.

In the above and subsequent description of the present specification, suitable examples of the various definitions to be included within the scope of the present invention are explained in detail as follows.

The term "lower" is intended to mean a group having one to six carbon atom(s), unless otherwise indicated.

Suitable "lower alkyl" and "lower alkyl moiety" in the terms "hydroxyimino(lower)alkyl", "optionally substituted ar(lower)alkyl", "ar(lower)alkylamino", "N-containing heterocyclic(lower)alkyl", "heterocyclicthio(lower)alkyl", "phenyl(lower)alkylamino", "phenyl(lower)alkyl", "lower alkylphenyl(lower)alkyl", "lower alkoxyphenyl(lower) alkyl", "benzimidazolyl(lower)alkyl", "pyridyl(lower) alkyl", "benzothiazolylthio(lower)alkyl", "indolyl(lower) alkyl" and "lower alkylcarbamoyl" may include straight or branched one such as methyl, ethyl, propyl, isopropyl, butyl, isobutyl, sec-butyl, tert-butyl, pentyl, hexyl, or the like.

Suitable "lower alkylene" may include straight or branched one having one to eight carbon atom(s), such as methylene, ethylene, propylene, butylene, amylene, hexylene, or the like.

Suitable "heterocyclic group" for W and "heterocyclic moiety" in the terms "heterocyclic(lower)alkyl" heterocyclicthio(lower)alkyl for $R_3$ or $R_4$, etc., may include the one containing at least one heteroatom selected from nitrogen, sulfur and oxygen atom, and may include saturated or unsaturated, monocyclic or bicyclic heterocyclic group. Preferable heterocyclic group may be N-containing heterocyclic group containing one to four nitrogen atom(s).

Suitable "N-containing heteromonocyclic group" may include the following groups.

(1) unsaturated three to eight membered (more preferably five to six membered) heteromonocyclic group containing one to four nitrogen atom(s), for example, pyrrolyl, pyrrolinyl, imidazolyl, pyrazolyl, pyridyl, pyrimidinyl, pyrazinyl, pyridazinyl, triazolyl, tetrazolyl, etc.;

(2) saturated three to eight membered (more preferably five to six membered) heteromonocyclic group containing one to three nitrogen atom(s), for example, pyrrolidinyl, imidazolidinyl, piperidyl, piperazinyl, etc.;

(3) unsaturated three to eight membered (more preferably five to six membered) heteromonocyclic group containing one to two oxygen atom(s) and one to three nitrogen atom(s), for example, oxazolyl, isoxazolyl, oxadiazolyl, etc.;

(4) saturated three to eight membered (more preferably five to six membered) heteromonocyclic group containing one to two oxygen atom(s) and one to three nitrogen atom(s), for example, morpholinyl, etc.;

(5) unsaturated three to eight membered (more preferably five to six membered) heteromonocyclic group containing one to two sulfur atom(s) and one to three nitrogen atom(s), for example, thiazolyl, thiadiazolyl, etc.;

(6) saturated three to eight membered (more preferably five to six membered) heteromonocyclic group containing one to two sulfur atom(s) and one to three nitrogen atom(s), for example, thiomorpholinyl, etc.

Suitable "N-containing heterobicyclic group may include benzimidazolyl, benzothiazolyl, imidazopyridyl, indolyl, isoindolyl, indazolyl, purinyl, adenyl, quinolyl, isoquinolyl, etc.

Suitable non N-containing heterocyclic group may include the following groups.

(1) heteromonocyclic group containing 1 to 2 sulfur atom(s), for example, thienyl, dihydrodithiinyl, dihydrodithionyl, etc.;

(2) unsaturated 3 to 8-membered (more preferably 5 or 6-memberd) heteromonocyclic group containing an oxygen atom, for example, furyl, pyranyl, etc.;

(3) saturated 3 to 8-membered (more preferably 5 or 6-membered) heteromonocyclic group containing 1 to 2 oxygen atom(s), for example, oxiranyl, oxolanyl, dioxolanyl, tetrahydrofuranyl, etc.;

(4) unsaturated 3 to 8-membered (more preferably 5 or 6-membered) heteromonocyclic group containing an oxygen atom and 1 to 2 sulfur atom(s), for example, dihydrooxathiinyl, etc.;

(5) unsaturated condensed heterocyclic group containing 1 to 4 oxygen atom(s), for example, methylenedioxyphenyl, benzodioxanyl, etc.;

(6) unsaturated condensed heterocyclic group containing 1 to 2 sulfur atom(s), for example, benzothienyl, benzodithiinyl, etc.;

(7) unsaturated condensed heterocyclic group containing an oxygen atom and 1 to 2 sulfur atom(s), for example, benzoxathiinyl; and the like.

Suitable "carbocyclic group" may be the one having three to ten carbon atoms, saturated or unsaturated such as cyclo(lower)alkyl or aryl, more preferably aryl, each of which may have one or more substituent(s).

Suitable "substituent" in the terms "heterocyclic or carbocyclic group" for W, "heterocyclic group selected from the group consisting of imidazolyl, imidazopyridyl, triazolyl or adenyl" for Z, and "lower alkyl, optionally substituted ar(lower)alkyl, ar(lower)alkylamino or heterocyclic(lower) alkyl, each of which may have one or more substituent(s)" for $R_3$ may include lower alkyl; hydroxy; lower alkoxy; amino; nitro; cyano; halogen; oxo; carboxy; esterified carboxy; carbamoyl, N-substituted carbamoyl; guanidinocarbonyl; aminotriazolyl; substituted or unsubstituted heterocyclic group; a group of the following formula; —NHC(O)—$R_3$ (wherein $R_3$ is as defined above); acyl; or the like.

Suitable "substituent" for "N-substituted carbamoyl" is lower alkyl such as the one mentioned above.

Suitable "lower alkoxy" and "lower alkoxy moiety" in the terms of "optionally substituted (lower)alkoxy", "phenyl (lower)alkoxy", "halophenyl(lower)alkoxy", "indolyl (lower)alkoxy" and "lower alkoxycarbonyl" may include methoxy, ethoxy, propoxy, isopropoxy, butoxy, isobutoxy, t-butoxy, pentyloxy, t-pentyloxy, hexyloxy, and the like.

Suitable "lower alkanoyl" may include formyl, acetyl, propionyl, butyryl, isobutyryl, valeryl, isovaleryl, oxalyl, succinyl, pivaloyl, etc.

Suitable "halogen" and "halogen moiety" in the term "halophenyl(lower)alkoxy" may be fluoro, chloro, bromo, or iodo.

Suitable "esterified carboxy" may be substituted or unsubstituted lower alkoxycarbonyl, for example, methoxycarbonyl, ethoxycarbonyl, propoxycarbonyl, etc., substituted or unsubstituted aryloxycarbonyl, for example, phenoxycarbonyl, 4-nitrophenoxycarbonyl, and the like.

Suitable "cyclo(lower)alkyl" may include cyclopropyl, cyclobutyl, cyclopentyl, cyclohexyl or the like.

Suitable "aryl" and "aryl moiety" in the terms "optionally substituted ar(lower)alkyl", "ar(lower)alkylamino" and "aryloxycarbonyl" may be phenyl, naphtyl, tolyl, xylyl, and the like.

Suitable "hydroxy protective group" may include common protective group and the like.

Suitable "common protective group" may include acyl, mono(or di or tri)phenyl(lower)alkyl which may have one or more substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

Suitable "acyl" may include aliphatic acyl group and acyl group containing an aromatic ring or heterocyclic ring.

And, suitable examples of the said acyl may be lower alkanoyl, lower alkoxycarbonyl (e.g., methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, etc.); lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, xyloyl, naphthoyl, phthaloyl, indancarbonyl, etc.); ar(lower)alkanoyl (e.g., phenylacetyl, phenylpropionyl, etc.); ar(lower)alkoxycarbonyl (e.g., benzyloxycarbonyl, phenethyloxycarbonyl, etc.).

Preferred embodiments of the object compounds (I) are represented by the following formula:

A compound of the formula [I]:

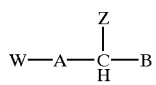

[I]

wherein
B is

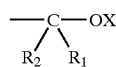

[wherein $R_1$ is hydrogen;
$R_2$ is hydrogen or lower alkyl; and
X is hydrogen], A is ethylene;

W is indolyl, benzothiazolyl, indazolyl, phenyl or naphthyl, each of which may have one or two substituent(s) selected from the group consisting of cyano, hydroxy, halogen, oxo, lower alkoxy, pheny(lower)alkoxy, halophenyl(lower)alkoxy, indolyl(lower)alkoxy which may have lower alkyl, lower alkyl, phenyl(lower)alkylamino, amino, nitro and —NH—C(O)—$R_3$ [wherein $R_3$ is lower alkyl, phenyl(lower)alkyl, lower alkylphenyl(lower)alkyl, lower alkoxyphenyl(lower)alkyl, phenyl(lower)alkylamino, phenyl, benzimidazolyl(lower)alkyl which may have lower alkyl, pyridyl(lower)alkyl, benzothiazolylthio(lower)alkyl or indolyl(lower)alkyl which may have one or two oxo]; and Z is imidazolyl, triazolyl or imidazopyridyl, each of which may have one substituent selected from the group consisting of carbamoyl, lower alkylcarbamoyl, (lower)alkoxycarbonyl and guanidinocarbonyl.

or a salt thereof.

More preferred embodiments of the object compound [I] are represented by the following formula:

A compound of the formula [I]:

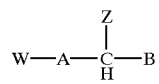

[I]

wherein
B is

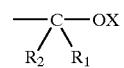

[wherein $R_1$ is hydrogen;
$R_2$ is hydrogen or lower alkyl; and
X is hydrogen], A is ethylene;

W is indolyl, benzothiazolyl, indazolyl, phenyl or naphthyl, each of which may have one or two substituent(s) selected from the group consisting of cyano, hydroxy, halogen, oxo, lower alkoxy, pheny(lower)alkoxy, halophenyl(lower)alkoxy, indolyl(lower)alkoxy which may have lower alkyl, lower alkyl, phenyl(lower)alkylamino, amino, nitro and —NH—C(O)—$R_3$ [wherein $R_3$ is lower alkyl, phenyl(lower)alkyl, (lower)alkylphenyl(lower)alkyl, (lower)alkoxyphenyl(lower)alkyl, phenyl(lower)alkylamino, phenyl, benzimidazolyl(lower)alkyl which may have lower alkyl, pyridyl(lower)alkyl, benzothiazolylthio(lower)alkyl or indolyl(lower)alkyl which may have one or two oxo]; and Z is imidazolyl which may have carbamoyl or guanidinocarbonyl; triazolyl which may have carbamoyl, (lower)alkylcarbonyl or lower alkoxycarbonyl; or imidazopyridyl, or a salt thereof.

Further more preferred embodiments of the object compound [I] are represented by the following formula:

A compound of the formula [I]:

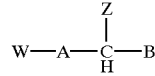

[I]

wherein
B is

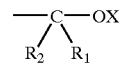

[wherein $R_1$ is hydrogen;
$R_2$ is hydrogen or lower alkyl; and
X is hydrogen], A is ethylene;

W is indolyl which may have one or two substituent(s) selected from the group consisting of cyano, hydroxy, halogen, oxo, lower alkoxy, pheny(lower)alkoxy, halophenyl(lower)alkoxy, indolyl(lower)alkoxy which may have lower alkyl, lower alkyl, phenyl(lower) alkylamino, amino, nitro and —NH—C(O)—R$_3$ [wherein R$_3$ is lower alkyl, phenyl(lower)alkyl, (lower) alkylphenyl(lower)alkyl, (lower)alkoxyphenyl(lower) alkyl, phenyl(lower)alkylamino, phenyl, benzimidazolyl(lower)alkyl which may have lower alkyl, pyridyl(lower)alkyl, benzothiazolylthio(lower) alkyl or indolyl(lower)alkyl which may have one or two oxo]; benzothiazolyl which may have oxo; indazolyl; phenyl which may have one or two halogen(s); or naphthyl; and Z is imidazolyl which may have carbamoyl or guanidinocarbonyl; triazolyl which may have carbamoyl, (lower)alkylcarbonyl or lower alkoxycarbonyl; or imidazopyridyl, or a salt thereof.

The processes for preparing the object compounds (I) and the starting compounds of the present invention are explained in detail in the following.

PROCESS 1

The compounds (I) or a salt thereof can be prepared by reacting the compound (II) or its reactive derivative at the hydroxy group or a salt thereof with the compound (III) or a salt thereof.

Suitable reactive derivative at the hydroxy group of the compound (II) may include halide, sulfonate, sulfate, diazo compound, and the like. More suitable derivatives at the hydroxy group of the compound (II) are loweralkylsulfonyloxy derivatives formed by the reaction of the compound (II) with (lower)alkylsulfonyl halide such as methylsulfonyl chloride and the like.

The reaction usually carried out in a solvent such as water, an alcohol [e.g. methanol, ethanol, etc.], methylene chloride, tetrahydrofuran, N,N-dimethylformamide a mixture thereof or any other solvent which does not adversely used as the solvent. The reaction temperature is not critical and the reaction is usually carried out under cooling to warming.

PROCESS 2

The compound (I-b) or a salt thereof can be prepared by deprotection of the hydroxy protective group of the compound (I-a) or a salt thereof. Suitable method of the deprotection may include conventional one such as hydrolysis, reduction and the like.

(1) For Hydrolysis:

The hydrolysis is preferably carried out in the presence of a base or an acid including Lewis acid.

Suitable base may be include an inorganic base and an organic base such as an metal hydroxide [e.g., sodium hydroxide, magnesium hydroxide, etc.], metal alkoxide [e.g., sodium methoxide, potassium methoxide, etc.], metal carbonate or metal bicarbonate, trialkylamine [e.g., trimethylamine, triethylamine, etc.], picoline, 1,5-diazabicyclo[4.3.0]non-5-ene, 1,4-diazabicyclo[2.2.2] octane, 1,8-diazabicyclo[5.4.0]undec-7-ene, and the like.

Suitable acid may include an organic acid, [e.g., formic acid, acetic acid, propionic acid, trichloroacetic acid, trifluoroacetic acid, etc.] and an inorganic acid [e.g., hydrochloric acid, hydrobromic acid, sulfuric acid, hydrogen chloride, hydrogen bromide, ammonium chloride, etc.]. The elimination using Lewis acid such as trihaloacetic acid [e.g., trichloroacetic acid, trifluoroacetic acid, etc.] or the like is preferably carried out in the presence of cation trapping agents [e.g., anisole, phenol, etc.].

The reaction usually carried out in a solvent such as water, an alcohol [e.g., methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(2) For Reduction:

Reduction is carried out in a conventional manner, including chemical reduction and catalytic reduction.

Suitable reducing agents to be used in chemical reduction are a combination of a metal (e.g., tin, zinc, iron, etc.) or metallic compound (e.g., chromium chloride, chromium acetate, etc.) and organic or inorganic acid (e.g., formic acid, acetic acid, propionic acid, trifluoroacetic acid, p-toluenesulfonic acid, hydrochloric acid, hydrobromic acid, etc.).

Suitable catalyst to be used in catalytic reduction are conventional ones such as platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, etc.), copper catalysts (e.g., reduced copper, Raney copper, Ullman copper, etc.), or the like. The reduction is usually carried out in a conventional solvent which does not adversely influence the reaction such as water, methanol, ethanol, propanol, dioxane, tetrahydrofuran, N,N-dimethylformamide, or a mixture thereof. Additionally, in case that the above mentioned acids to be used in chemical reduction are in liquid, they can also be used as a solvent.

The reaction temperature of this reduction is not critical and the reaction is usually carried out under cooling to warming.

PROCESS 3

The compound (I-d) or a salt thereof can be prepared by reduction of the compound (I-c) or a salt thereof.

Reduction is carried out in same manner as mentioned in Process 2.

PROCESS 4

The compound (I-e) can be prepared by reacting the compound (I-d) or its reactive derivative at the amino group or a salt thereof with the compound (IV) or its reactive derivative at the carboxy group or a salt thereof.

Suitable reactive derivative at the amino group of the compound (I-d) may include Schiffs base type imino or its tautomeric enamine type isomer formed by the reaction of the compound (I-d) with a catbonyl compound such as aldehyde, ketone, or the like; a silyl derivative formed by the reaction of the compound (I-d) with a silyl compound such as N,N-bis(trimethylsilyl)acetamide, N-trimethylsilylacetamide or the like; a derivative formed by the reaction of the compound (I-d) with phosphorus trichloride or phosgene or the like.

Suitable reactive derivative at the carboxy group of the compound (IV) may include conventional one such as an acid halide, an acid anhydride, an activated amide, an activated ester, and the like.

The reaction usually carried out in a solvent such as water, an alcohol [e.g., methanol, ethanol, etc.], methylene chloride, tetrahydrofuran, a mixture thereof or any other solvent which does not adversely influence the reaction.

PROCESS 5

The compound (I-g) or a salt thereof can be prepared by reacting the compound (I-f) or its reactive derivative at the carboxy group or a salt thereof with guanidine or a salt thereof.

Suitable salt of guanidine may include hydrochloride, hydrobromide, or the like.

Suitable reactive derivative at the carboxy group can be referred to the ones exemplified in the Process 4.

This reaction can be carried out in a similar manner to that of Example 10. Therefore, reacting condition such as reagent, solvent, temperature, etc. are referred to those described in Example 10.

PROCESS 6

The compound (I-h) or a salt thereof can be prepared by subjecting the compound (I-f) or its reactive derivative at the carboxy group or a salt thereof to amidation.

Suitable reactive derivative at the carboxy group of the compound (I-h) can be referred to the ones as exemplified in the Process 4.

Amidation reaction can be carried out by reacting the compound (I-f) or its reactive derivative at the carboxy group or a salt thereof with an amidation reagent.

This amidation reagent is the "amine compound" or its reactive derivative at the amino group or a salt thereof corresponding to the object amide, and the suitable examples thereof may include ammonia; lower alkylamine; higher alkylamine; N,N-di(lower)alkylamine; N-(lower)alkyl-N-ar(lower)alkylamine; N-carboxy(lower)alkylamine; etc.

This reaction can be carried out in a similar manner to that of Example 11. Therefore, reacting condition, such as reagent, solvent, temperature, etc. are referred to those described in Example 11.

PROCESS 7

The compound (I-i) or a salt thereof can be prepared by the compound (I-d) or its reactive derivative at the amino group or a salt thereof with the compound (III-a) or a salt thereof.

Suitable reactive derivative at the amino group of the compound (I-i) can be referred to the ones exemplified in the Process 4.

Suitable salt of the compound (III-a) may include hydrochloride, hydrobromide, or the like.

This reaction can be carried out in a similar manner to that of Preparation 12.

PROCESS 8

The compound (I-j) or a salt thereof can be prepared by subjecting the compound (I-n) to deprotection of the hydroxy protective group and then reacting the deprotected compound with the compound $R_5$—Y or $R_6$—$OR_7$.
(wherein $R_5$, $R_6$, $R_7$ and Y are each as defined above)

The deprotection can be carried out in a similar manner described in Process 1.

This reaction can be carried out in a similar manner to that of Preparation 21 or Preparation 23.

PROCESS 9

The compound [I-k] or a salt thereof can be prepared by oxidation reaction of the compound [I-o] or a reactive derivatives at the hydroxy group.

Suitable reactive derivatives at the hydroxy group can be referred to ones in Process 1.

For Oxidation:

Oxidation in this process is carried out in a conventional manner with a conventional oxidizing agent.

Suitable examples of such oxidizing agent are inorganic peracid or its salt (e.g., periodic acid, persulfuric acid, etc.) or the sodium or potassium salt thereof, an organic peracid or its salt (e.g., perbenzoic acid, 2-chloroperbenzoic acid, 3-chloroperbenzoic acid, trifluoroperacetic acid, etc. or the sodium or potassium salt thereof, etc.), ozone, hydrogen peroxide, urea-hydrogen and the like.

The present reaction is preferably conducted in the presence of a compound comprising a Group Vb or VIb metal in the Periodic Table, for example, tungstic acid, molybdic acid, vanadic acid, etc. or their salt with an alkali metal (e.g., sodium, potassium, etc.), an alkaline earth metal (e.g., calcium, magnesium, etc.) or ammonium, etc., or vanadium pentoxide.

The present oxidation is usually conducted in a solvent such as water, acetic acid, ethyl acetate, chloroform, dichloromethane, tetrahydrofuran, dioxane, N,N-dimethylformamide or any other solvent which does not have any adverse effect to the reaction.

This reaction can be carried out in a similar manner to that of Example 18.

PROCESS 10

The compound [I-l] or a salt thereof can be prepared by reacting the compound of [I-k] or a salt thereof with hydroxylamine or a salt thereof.

This reaction can be carried out in a similar manner to that of Example 19.

PROCESS 11

The compound [I-m] or a salt thereof can be prepared by reacting the compound [I-k] or a salt thereof with the compound [III-d] or a salt thereof.

This reaction can be carried out in a similar manner to that of Example 20.

The starting compound (II) or a salt thereof can be prepared by the following processes.

PROCESS A

The compound (V-a) or a salt thereof can be prepared by reacting the compound (V) or its reactive derivative at the hydroxy group or a salt thereof with the compound (VI) or a salt thereof. And, by deprotection of the hydroxy group of the compound (V-a), the compound (II-a) or a salt thereof can be prepared. And then, the compound (II-b) or a salt thereof can be prepared by introduction of a hydroxy protective group to the compound (II-a) or a salt thereof.

Suitable derivative at the hydroxy group of the compound (V) may be the same one as described in Process 1.

These reactions can be carried out in a similar manner to those of Preparation 2 and Preparation 3. Therefore, reacting conditions, such as reagent, solvent, reacting temperature, etc., are referred to those in Preparation 2 and Preparation 3.

Suitable salt of the compounds (I), (I-a)–(I-o), starting compounds (II), (II-a), (II-b), and also (III), (III-a)–(III-d), (IV), (V), (V-a), (VI) and their reactive derivatives in Process 1 to Process 11 and Process A are pharmaceutically acceptable conventional non-toxic salts and may be a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an organic acid addition salt, for example, formate, acetate, trifluoroacetate, maleate, tartrate, fumarate, methanesulfonate, etc., an inorganic acid salt, for example, hydrochloride, hydrobromide, sulfate, phosphate, etc., a salt with an amino acid, for example, aspartic acid salt, glutamic acid salt, etc., or the like.

The object compounds (I) or a pharmaceutically acceptable salt thereof can usually be administered to mammals including human being in the form of a conventional pharmaceutical composition such as oral dosage form (e.g., capsule, micro-capsule, tablet, granule, powder, troche, syrup, aerosol, inhalation, suspension, emulsion, etc.), injection dosage form, suppository, ointment, or the like.

The pharmaceutical composition of this invention can contain various organic or inorganic carrier materials, which are conventionally used for pharmaceutical purpose such as excipient (e.g., sucrose, starch, mannit, sorbit, lactose, glucose, cellulose, talc, calcium phosphate, calcium carbonate, etc.), binding agent (e.g., cellulose, methyl cellulose, hydroxypropyl cellulose, gelatin, gum arabic, starch, etc.), disintegrator (e.g., starch, carboxymethyl cellulose, etc.), lubricant (e.g., magnesium stearate, talc, sodium laurylsulfate, etc.), flavoring agent (e.g., citric acid, mentol, glycerine, orange powders, etc.), preservative (e.g., sodium benzoate, sodium bisulfate, methylparaben, etc.), stabilizer (e.g., citric acid, sodium citrate, acetic acid, etc.), suspending agent (e.g., methyl cellulose, polyvinylpyrrolidine, aluminum stearate, etc.), dispersing agent, aqueous diluting agent (e.g., water, etc.), base wax (e.g., cacao butter, polyethyleneglycol, white petrolatum).

While the dosage of therapeutically effective amount of a compound (I) will vary depending on the age and condition of each individual patient, an average single dose of about 0.01 mg, 0.1 mg, 1 mg, 10 mg, 50 mg, 100 mg, 250 mg, 500 mg and 1000 mg of the compound (I) may be effective for treating the above-mentioned diseases. In general, amounts between 0.01 mg/body and about 1,000 mg/body may be administered per day.

Adenosine (Ado) is an endogenous purine nucleoside released by cells as part of the normal metabolic machinery. Ado has wide variety of biological activities, namely potent antiinflammatory and immunosuppressive properties, protective effects in cardiovascular and cerebrovascular ischemia anticonvulsant effects and modulation effects of platelet aggregation, lipolysis, glycogenesis, blood flow and neurotransmission. Ado shows the biological activities by binding to its receptors anchored in the cell membrane. Therefore, it is the beneficial treatment for many diseases to perform the pharmacological elevation of extracellular Ado concentrations.

Adenosine deaminase (ADA) catalyzes an essentially irreversible deamination of adenosine or deoxyadenosine to inosine or deoxyinosine, respectively. In the last 10 years, ADA, which was considered to be cytosolic, has been found on the cell surface of many cells. Thus, blocking ADA activity with specific inhibitor is the potent way to elevate Ado concentrations in biological systems and the beneficial treatment for many diseases.

The object compound (I) or pharmaceutically acceptable salts thereof of this invention possesses ADA inhibiting activity. The object compound (I) and pharmaceutically acceptable salt, therefore, are useful in immunomodulation, especially immunosuppression, antiinflammation and various diseases on which Ado is effective, as follows:

a) Treating and/or preventing autoimmune diseases and inflammatory conditions, e.g., various pains collagen diseases, autoimmune diseases, various immunity diseases, and the like in human beings or animals, and more particularly for the treating and/or preventing inflammation and pain in joint and muscle [e.g., rheumatoid arthritis, rheumatoid spondylitis, osteoarthritis, gouty arthritis, etc.], inflammatory skin condition [e.g., sunburn, eczema, etc.], inflammatory eye condition [e.g., conjunctivitis, etc.], lung disorder in which inflammation is involved [e.g., asthma, bronchitis, pigeon fancier's disease, farmer's lung, etc.], condition of the gastrointestinal tract associated with inflammation [e.g., aphthous ulcer, Crohn's diseases, atrophic gastritis, ulcerative colitis, coeliac disease, regional ileitis, irritable bowel syndrome, etc.], gingivitis, (inflammation, pain and tumescence after operation or injury), pyrexia, pain and other conditions associated with inflammation, systemic lupus erythematosus, scleroderma, polymyositis, polychondritis, periarteritis nodose, ankylosing spondylitis, inflammatory chronic renal condition [e.g., nephrotic syndrome, glomerulonephritis, membranous nephritis, etc.], acute nephritis, rheumatic fever, Sjogren's syndrome, Behcet disease, thyroiditis, type diabetes, dermatomyositis, chronic active hepatitis, acute hepatitis, myasthenia gravis, idiopathic sprue, Grave's disease, multiple sclerosis, primary biliary cirrhosis, Reiter's syndrome, autoimmune hematological disorders [e.g., hemolytic anemia, pure red cell anemia, idiopathic thrombocytopenia; aplastic anemia, etc.], myasthenia gravis, uveitis, contact dermatitis, psoriasis, Kawasaki disease, sarcoidosis, Wegner's granulomatosis, Hodgkin's disease, or the like.

b) Treating and/or preventing organ or tissue allo- or xeno-transplant rejection, e.g., kidney, liver, heart, lung, combined hart-lung, bone marrow, islet cells, pancreatic, skin, chromaffin or dopamine producing cells, small bowel, or corneal transplantation. Treating and/or preventing graft-versus-host disease, such as occurs following bone marrow transplantation.

c) Treating and/or preventing various leukemias, including virus induced, or various lymphomas.

d) Treating and/or preventing diseases that arise from, or are aggravated by, insufficient blood flow through a particular organ or portion thereof, e.g., heart attacks or strokes, the microvascular disease of diabetes mellitus, atherosclerosis, or events resulting in a less prolonged loss of blood flow (e.g., angina pectoris, transient ischemic attacks, bowel ischemia, kidney ischemia, intermittent claudication of skeletal muscle, migraine headaches, Raynaud's phenomenon), or the like.

In order to illustrate the usefulness of the object compound (I), the pharmacological test data of the compound (I) are shown in the following.

Adenosine Deaminase (ADA) Enzyme Assay

[1]

| Test Compound: | 1-[ (R)-1-hydroxy-4-(6-(4-phenylbutyrylamino)-indol-1-yl)-2-butyl]imidazole-4-carboxamide |
|---|---|

Test Method:

The reaction velocity (V) is measured by a change in absorbance at 265 nm (A265) resulting from the deamination of adenosine. Human ADA was expressed and purified from ADA-deficient bacterial strain. Reaction mixtures in a total volume of 200 μl contained 25 mU/ml of ADA and varying concentrations of adenosine and test compounds in 10 mM phosphate buffer saline (pH 7.4). The reaction was started by addition of ADA to a mixture of adenosine and test compound. The reaction was followed at room temperature by recording decrease in A265 for 5 minutes in SPECTRAmax 250 (Molecular Devices, USA) to automatically calculate Vmax. The inhibition constant (Ki) values of test compounds were determined by Dixon plot.

Results:

| Test Compound: | Ki = 16 nM (Example 6-(2)) |
|---|---|

[2]
Test Method:

The reaction velocity (V) is measured by a change in absorbance at 265 nm (A265) resulting from the deamination of adenosine. Human ADA was expressed and purified from ADA-deficient bacterial strain. Reaction mixture of a total volume of 200 μl contained 0.16 μg/ml of ADA, 0.1 mM of adenosine and test compound in 10 mM phosphate buffer saline (pH 7.4). The reaction was started by addition of ADA to a mixture of adenosine and test compound. The reaction was followed at room temperature by recording decrease in A265 for 3 minutes in SPECTRAmax 250 (Molecular Devices, USA) to automatically calculate Vmax. Inhibitory potency of test compound was expressed as $IC_{50}$ value, the drug concentration required to produce 50% inhibition of Vmax in comparison to vehicle treatment.

| Test compound: | 1-[(2S,3R)-2-hydroxy-5-(1-naphthyl)-3-pentyl]-1,2,4-triazole (Compound A)<br>1-[(R)-1-hydroxy-4-(1-methyl-5-(3-phenylpropoxy)indol-3-yl)-2-butyl)imidazole-4-carboxamide (Compound B) |
|---|---|

Results

| Test compound | $IC_{50}$ (nM) |
|---|---|
| Compound A (Example No. 14(7)) | 27 |
| Compound B (Example No. 12(21)) | 10 |

The following Preparations and Examples are given for the purpose of illustrating the present invention in detail.

PREPARATION 1

To an ice cooled solution of methyl (4S)-2,2-dimethyl-1,3-dioxolane-4-acetate (1.0 g, 5.74 mmol) in methanol (10 ml) was added portionwise $NaBH_4$ (1.3 g, 34.4 mmol). After the addition was completed, the reaction mixture was stirred at room temperature for 3 hours. Water (40 ml) was added, and the resulting mixture was stirred for several minutes and concentrated in vacuo. The residue was extracted with ethyl acetate. The organic layer was washed with brine, dried (magnesium sulfate), and concentrated in vacuo to give 2-[(4S)-2,2-dimethyl-1,3-dioxolan-4-yl]ethanol (808.9 mg, 96.4%) as a colorless oil.

IR (Neat): 3700–3100, 2985, 2940, 2881, 1234, 1062 $cm^{-1}$; NMR ($CDCl_3$, δ): 1.37 (3H, s), 1.43 (3H, s), 1.83 (2H, q, J=5.9 Hz), 2.21 (1H, br), 3.55–3.90 (3H, m), 4.05–4.35 (2H, m).

PREPARATION 2

To a stirred mixture of 2-[(4S)-2,2-dimethyl-1,3-dioxolan-4-yl]ethanol (803 mg, 5.50 mmol) and methanesulfonyl chloride (882 mg, 7.69 mmol) in dichloromethane (10 ml) was added dropwise triethylamine (778 mg, 7.69 mmol) at ice-bath temperature. After 1 hour, the reaction mixture was partitioned between dichloromethane and water. The organic layer was washed with brine and dried ($MgSO_4$), and concentrated in vacuo to give a methanesulfonate (1.23 g, 100%) as an oil. This material was used immediately without further purification. To a solution of indole (634 mg, 5.50 mmol) in DMF (10 ml) was added NaH (60% in mineral oil, 220 mg, 5.50 mmol) at room temperature. The reaction mixture was stirred for 30 minutes. A solution of the methanesulfonate prepared above in DMF (5 ml) was added and the resulting mixture was stirred for 1 hour at room temperature. The reaction mixture was cooled to 10° C. in an ice-bath, and the insoluble material was filtered and washed thoroughly with dichloromethane. The filtrate and the washing were combined and then washed with brine. The organic layer was dried (magnesium sulfate) and concentrated in vacuo. The residue was purified by silica gel (40 g) column chromatography eluting with toluene/ethyl acetate (50:1) to give 1-[2-((4S)-2,2-dimethyl-1,3-dioxolan-4-yl)ethyl]-1H-indole (1.15 g, 85.6%).

IR (KBr): 2983, 2933, 2875, 1236, 1083 $cm^{-1}$; NMR ($CDCl_3$, δ): 1.35 (3H, s), 1.46 (3H, s), 1.90–2.20 (2H, m), 3.40–4.35 (5H, m), 6.50 (1H, d, J=3.2 Hz), 7.05–7.25 (3H, m), 7.38 (1H, d, J=7.3 Hz), 7.64 (1H, d, J=7.5 Hz); MS: 246 $(M+H)^+$.

PREPARATION 3

To an ice cooled solution of 1-[2-((4S)-2,2-dimethyl-1,3-dioxolan-4-yl)ethyl]-1H-indole (520 mg, 2.12 mmol) in THF (10 ml) was added portionwise 1N-HCl (8.48 ml). After the addition was completed, the reaction mixture was stirred at room temperature for 2.5 hours. An aqueous solution of $NaHCO_3$ was added, and the resulting mixture was stirred for several minutes. The mixture was extracted with ethyl acetate. The organic layer was washed with brine, dried (magnesium sulfate) and concentrated in vacuo to give (S)-4-(1-indolyl)-butane-1,2-diol (449.3 mg, 103%) as an oil. This material was used immediately without further purification. To an ice cooled solution of (S)-4-(1-indolyl)-butane-1,2-diol in DMF (10 ml) was added imidazole (433 mg, 6.36 mmol) followed by tert-butyldimethylsilylchloride (335 mg, 2.23 mmol). After 30 minutes, the ice-bath was removed and then the mixture was stirred overnight at room temperature. The reaction mixture was poured into water (100 ml) and extracted with ethyl acetate. The organic layer was washed with brine, dried (magnesium sulfate), and concentrated in vacuo. The residue was purified by silica gel (15 g) column chromatography eluting with hexane/ethyl acetate (20:1) to give (S)-[1-(tert-butyldimethylsilyloxy)-4-(1-indolyl)]-butan-2-ol (542 mg, 80.0%) as a colorless oil.

IR (Neat): 3800–2800, 1238, 1087 cm$^{-1}$; NMR (CDCl$_3$, δ): 0.03 (6H, s), 0.88 (9H, s), 1.80–2.05 (2H, m), 2.47 (1H, d, J=3.7 Hz), 3.30–3.70 (3H, m), 4.25–4.40 (2H, m), 6.49 (1H, d, J=3.1 Hz), 7.05–7.30 (3H, m), 7.40 (1H, d, J=7.4 Hz), 7.63 (1H, d, J=7.6 Hz); MS: 320 (M+H)$^+$.

PREPARATION 4

This compound was prepared by a similar procedure to that of Preparation 2.
1-[2-((4S)-2,2-Dimethyl-1,3-dioxolan-4-yl)ethyl]-1H-6-nitroindole (2.19 g, 66.8%)

IR (KBr): 2985, 2938, 2879, 1583, 1504, 1321, 1236, 1074 cm$^{-1}$; NMR (CDCl$_3$, δ): 1.34 (3H, s), 1.48 (3H, s), 1.90–2.25 (2H, m), 3.45–3.60 (1H, m), 3.85–4.05 (2H, m), 4.41 (2H, dd, J=7.9 Hz, 5.6 Hz), 6.61 (1H, d, J=3.1 Hz), 7.42 (1H, d, J=3.1 Hz), 7.65 (1H, d, J=8.8 Hz), 8.01 (1H, dd, J=8.8 Hz, 2.0 Hz), 8.41 (1H, d, J=2.0 Hz); MS: 291 (M+H)$^+$.

PREPARATION 5

This compound was prepared by a similar procedure to that of Preparation 3.
(S)-[1-(tert-Butyldimethylsilyloxy)-4-(6-nitroindol-1-yl)]-butan-2-ol (1.61 g, 88.3%)

IR (KBr): 3558, 2954, 2857, 1511, 1463, 1330, 1238, 1089 cm$^{-1}$; NMR (CDCl$_3$, δ): 0.04 (6H, s), 0.88 (9H, s), 1.80–2.00 (2H, m), 2.51 (1H, d, J=3.2 Hz), 3.30–3.65 (3H, m), 4.43 (2H, dd, J=7.7 Hz, 6.0 Hz), 6.59 (1H, d, J=3.1 Hz), 7.45 (1H, d, J=3.1 Hz), 7.65 (1H, d, J=8.8 Hz), 8.01 (1H, dd, J=8.8 Hz, 2.0 Hz), 8.39 (1H, d, J=2.0 Hz); MS: 365 (M+H)$^+$.

PREPARATION 6

This compound was prepared by a similar procedure to that of Preparation 2. In this case, 3-methylindole was added instead of indole.
1-[2-((4S)-2,2-dimethyl-1,3-dioxolan-4-yl)ethyl]-1H-3-methylindole (1.34 g, 75.9%)

IR (KBr): 3050, 2983, 2927, 2873, 1238, 1070 cm$^{-1}$; NMR (CDCl$_3$, δ): 1.34 (3H, s), 1.45 (3H, s), 1.90–2.20 (2H, m), 2.32 (3H, s), 3.45 (1H, dd, J=7.5 Hz, 6.7 Hz), 3.85–4.35 (4H, m), 6.88 (1H, s), 7.05–7.30 (2H, m), 7.33 (1H, d, J=7.9 Hz), 7.56 (1H, d, J=7.6 Hz); MS: 260 (M+H)$^+$.

PREPARATION 7

This compound was prepared by a similar procedure to that of Preparation 3.
(S)-[1-(tert-Butyldimethylsilyloxy)-4-(3-methylindol-1-yl)]-butan-2-ol (1.50 g, 90.2%)

IR (Neat): 3700–3100, 3050, 2948, 2929, 2859, 1249, 1087, 840 cm$^{-1}$; NMR (CDCl$_3$, δ): 0.03 (6H, s), 0.88 (9H, s), 1.80–2.00 (2H, m), 2.32 (3H, s), 2.45 (1H, d, J=3.8 Hz), 3.34 (1H, dd, J=9.8 Hz, 7.1 Hz), 3.50–3.70 (2H, m), 4.26 (2H, dd, J=7.6 Hz, 6.0 Hz), 6.91 (1H, s), 7.05–7.30 (2H, m), 7.34 (1H, d, J=8.0 Hz), 7.56 (1H, d, J=7.6 Hz); MS: 334 (M+H)$^+$.

PREPARATION 8

To a stirred mixture of (S)-[1-(tert-butyldimethylsilyloxy)-4-(3-methylindol-l-yl)]-butan-2-ol (1.37 g, 4.11 mmol) and methanesulfonyl chloride (565 mg, 4.93 mmol) in dichloromethane (20 ml) was added dropwise triethylamine (499 mg, 4.93 mmol) at ice-bath temperature. After 1 hour, the reaction mixture was partitioned between dichloromethane and water. The organic layer was washed with brine and dried (MgSO$_4$), and concentrated in vacuo to give the methanesulfonate (1.69 g, 100%) as an oil. This material was used for the next reaction without further purification. To a solution of methyl 4-imidazolecarboxylate (518 mg, 4.11 mmol) in DMF (20 ml) was added NaH (60% in mineral oil, 164 mg, 4.11 mmol) at room temperature. The reaction mixture was stirred for 30 minutes. The methanesulfonate prepared above was added and the resulting mixture was stirred for 48 hours at 75° C. The reaction mixture was cooled to 10° C. in an ice-bath, and the insoluble material was filtered and washed thoroughly with dichloromethane. The filtrate and the washing were combined and then washed with brine. The organic layer was dried (sodium sulfate) and concentrated in vacuo. The residue was purified by silica gel (40 g) column chromatography eluting with toluene/ethyl acetate (20:1) to give methyl 1-[(R)-1-(tert-butyldimethylsilyloxy)-4-(3-methylindol-1-yl)-2-butyl] imidazole-4-carboxylate (681 mg, 7.6%).

IR (Neat): 2948, 2888, 2857, 1727, 1189, 1124, 840 cm$^{-1}$; NMR (CDCl$_3$, δ): −0.08 (6H, s), 0.82 (9H, s), 2.20–2.55 (5H, m), 3.60–4.25 (8H, m), 6.68 (1H, s), 7.05–7.25 (3H, m), 7.45 (1H, s), 7.57 (1H, d, J=7.6 Hz), 7.68 (1H, s); MS: 442 (M+H)$^+$.

EXAMPLE 1

To a stirred mixture of (S)-[1-(tert-butyldimethylsilyloxy)-4-(1-indolyl)]-butan-2-ol (520 mg, 1.63 mmol) and methanesulfonyl chloride (261 mg, 2.28 mmol) in dichloromethane (10 ml) was added dropwise triethylamine (231 mg, 2.28 mmol) at ice-bath temperature. After 1 hour, the reaction mixture was partitioned between dichloromethane and water. The organic layer was washed with brine and dried (MgSO$_4$), and concentrated in vacuo to give the methanesulfonate (687 mg, 106%) as an oil. This material was used for the next reaction without further purification. To a solution of 4-imidazolecarboxamide (181 mg, 1.63 mmol) in DMF (10 ml) was added NaH (60% in mineral oil, 65 mg, 1.63 mmol) at room temperature. The reaction mixture was stirred for 1 hour at 70° C. The methanesulfonate prepared above was added and the resulting mixture was stirred for 38 hours at 70° C. The reaction mixture was cooled to 10° C. in an ice-bath, and the insoluble material was filtered and washed thoroughly with dichloromethane. The filtrate and the washing were combined and then washed with brine. The organic layer was dried (sodium sulfate) and concentrated in vacuo. The residue was purified by silica gel (24 g) column chromatography eluting with chloroform/methanol (30:1) to give 1-[(R)-1-(tert-butyldimethylsilyloxy)-4-(1-indolyl)-2-butyl] imidazole-4-carboxamide (312.3 mg, 46.5%).

IR (KBr): 3600–3000, 2950, 2857, 1662, 1594, 1259, 1126 cm$^{-1}$; NMR (CDCl$_3$, δ): −0.10 (3H, s), −0.08 (3H, s), 0.81 (9H, s), 2.25–2.60 (2H, m), 3.60–4.35 (5H, m), 5.41 (1H, brs), 6.52 (1H, d, J=3.1 Hz), 6.90 (1H, d, J=3.1 Hz), 6.98 (1H, brs), 7.05–7.30 (3H, m), 7.40 (1H, s), 7.64 (1H, d, J=7.6 Hz), 7.67 (1H, s); MS: 413 (M+H)$^+$.

EXAMPLE 2

To an ice cooled solution of 1-[(R)-1-(tert-butyldimethylsilyloxy)-4-(1-indolyl)-2-butyl]imidazole-4-carboxamide (176.3 mg, 0.427 mmol) in THF (5 ml) was added dropwise 1.0 M Bu$_4$NF in THF (641 ml). After the addition was completed, the reaction mixture was stirred at ice-bath temperature for 30 minutes. 25% AcONH$_4$ (4 ml) was added, and the resulting mixture was stirred for several minutes and then extracted with ethyl acetate. The organic layer was washed with brine, dried (sodium sulfate) and concentrated in vacuo. The residue was purified by silica gel (6 g) column chromatography eluting with chloroform/methanol. (10:1) to give 1-[(R)-1-hydroxy-4-(1-indolyl)-2-butyl]imidazole-4-carboxamide (81.7 mg, 64.1%) as a white solid.

mp: 127–130° C.; IR (KBr): 3700–2700, 1666, 1583 cm$^{-1}$; NMR (DMSO-d$_6$, δ): 2.20–2.40 (2H, m), 3.60 (2H, t, J=5.5 Hz), 3.90–4.20 (3H, m), 5.05 (1H, t, J=5.3 Hz), 6.43 (1H, d, J=3.1 Hz), 6.95–7.40 (6H, m), 7.54 (1H, d, J=7.3 Hz), 7.70 (1H, s), 7.79 (1H, s); MS: 299 (M+H)$^+$; [α]$_D^{26.5}$: +36.60° (C=0.50, EtOH).

EXAMPLE 3

This compound was prepared by a similar procedure to that of Example 1.
1-[(R)-1-(tert-Butyldimethylsilyloxy)-4-(6-nitroindol-1-yl)-2-butyl]imidazole-4-carboxamide (488.8 mg, 25.4%)

IR (KBr): 3600–3000, 2950, 2858, 1662, 1504, 1332, 1120, 840 cm$^{-1}$; NMR (CDCl$_3$, δ): −0.08 (3H, s), −0.06 (3H, s), 0.81 (9H, s), 2.25–2.65 (2H, m), 3.65–4.20 (5H, m), 5.44 (1H, brs), 6.62 (1H, d, J=3.1 Hz), 6.97 (1H, brs), 7.16 (1H, d, J=3.1 Hz), 7.40 (1H, s), 7.66 (1H, s), 7.68 (1H, d, J=8.8 Hz), 8.04 (1H, dd, J=8.8 Hz, 2.0 Hz), 8.18 (1H, d, J=2.0 Hz); MS: 458 (M+H)$^+$.

EXAMPLE 4

To a mechanically stirred mixture of 1-[(R)-1-(tert-butyldimethylsilyloxy)-4-(6-nitroindol-1-yl)-2-butyl]imidazole-4-carboxamide (450 mg, 0.98 mmol) and ammonium chloride (45 mg) in ethanol (10 ml) and water (5 ml) was added portionwise iron powder (450 mg) at 90° C. The resulting mixture was stirred for 40 minutes at 90° C. After cooling, the insoluble material was filtered through Celite and washed with ethanol and ethyl acetate. The filtrate and the washing were combined and concentrated in vacuo. The resulting residue was extracted with ethyl acetate and washed with brine. The organic layer was dried (sodium sulfate) and concentrated in vacuo to give 1-[(R)-4-(6-aminoindol-1-yl)-1-(tert-butyldimethylsilyloxy)-2-butyl]imidazole-4-carboxamide (397 mg, 94.7%). This material was used for the next reaction without further purification.

IR (KBr): 3700–3000, 2935, 2858, 1662, 1627 1594, 1257, 1126, 840 cm$^{-1}$; NMR (CDCl$_3$, δ): −0.10 (3H; s), −0.08 (3H, s), 0.81 (9H, s), 2.00–2.70 (4H, br), 3.60–4.15 (5H, m), 5.44 (1H, brs), 6.36 (1H, d, J=1.9 Hz), 6.38 (1H, d, J=3.2 Hz), 6.57 (1H, dd, J=8.3 Hz, 1.9 Hz), 6.71 (1H, d, J=3.2 Hz), 7.00 (1H, brs), 7.39 (1H, d, J=8.3 Hz), 7.41 (1H, s), 7.68 (1H, s); MS: 428 (M+H)$^+$. cl EXAMPLE 5

To a stirred mixture of 3-phenylpropionic acid (46 mg, 0.304 mmol) and 1-hydroxybenzotriazol (45 mg, 0.334 mmol) in dichloromethane (5 ml) was added 1-(3-dimethylaminopropyl)-3-ethylcarbodiimide (52 mg, 0.334 mmol) at ice-bath temperature. The mixture was stirred for 40 minutes at room temperature. And then 1-[(R)-4-(6-aminoindol-1-yl)-1-(tert-butyldimethylsilyloxy)-2-butyl]imidazole-4-carboxamide (130 mg, 0.304 mmol) was added to the mixture at ice-bath temperature. After adding, the resulting mixture was stirred for 4 hours at room temperature. The solvent was concentrated in vacuo. And then the residue was extracted with ethyl acetate and washed with water and brine. The organic layer was dried (sodium sulfate) and concentrated in vacuo. The residue was purified by silica gel (6 g) column chromatography eluting with chloroform/methanol (30:1) to give 1-[(R)-1-(tert-butyldimethylsilyloxy)-4-(6-(3-phenylpropionylamino)indol-1-yl)-2-butyl]imidazole-4-carboxamide (170.6 mg, 100%).

IR (KBr): 3600–3000, 2933, 2858, 1660, 1593, 1255, 1126, 840 cm$^{-1}$; NMR (CDCl$_3$, δ): −0.10 (3H, s), −0.08 (3H, s), 0.81 (9H, s), 2.20–2.55 (2H, m), 2.73 (2H, t, J=7.6 Hz), 3.10 (2H, t, J=7.6 Hz), 3.60–4.25 (5H, m), 5.42 (1H, brs), 6.45 (1H, d, J=3.1 Hz), 6.86 (1H, d, J=3.1 Hz), 6.90–7.05 (2H, m), 7.15–7.35 (5H, m), 7.40–7.65 (5H, m); MS: 560 (M+H)$^+$.

EXAMPLE 6

These compounds were prepared by a similar procedure to that of Example 2.
(1) 1-[(R)-1-Hydroxy-4-(6-(3-phenylpropionylamino)indol-1-yl)-2-butyl]imidazole-4-carboxamide (96.6 mg, 80.9%)

mp: amorphous (97–100° C.); IR (KBr): 3700–2800, 1656, 1590, 1259 cm$^{-1}$; NMR (DMSO-d$_6$, δ): 2.20–2.40 (2H, m), 2.63 (2H, t, J=7.5 Hz), 2.94 (2H, t, J=7.5 Hz), 3.60 (2H, t, J=5.2 Hz), 3.80–4.20 (3H, m), 5.07 (1H, t, J=5.2 Hz), 6.36 (1H, d, J=3.0 Hz), 6.95–7.35 (9H, m), 7.43 (1H, d, J=8.3 Hz), 7.65–7.90 (3H, m), 9.86 (1H, brs); MS: 446 (M+H)$^+$; [α]$_D^{24.6}$: +18.90+ (C=0.50, EtOH)
(2) 1-[(R)-1-Hydroxy-4-(6-(4-phenylbutyrylamino)indol-1-yl)-2-butyl]imidazole-4-carboxamide (96.6 mg, 80.9%)

mp: amorphous (134–140° C.); IR (KBr): 3600–3000, 2935, 1656, 1591, 1257 cm$^{-1}$; NMR (DMSO-d$_6$, δ): 1.80–2.05 (2H, m), 2.15–2.40 (4H, m), 2.64 (2H, t, J=7.5 Hz), 3.59 (2H, t, J=5.2 Hz), 3.80–4.20 (3H, m), 5.06 (1H, t, J=5.2 Hz), 6.36 (1H, d, J=3.0 Hz), 6.95–7.40 (9H, m), 7.43 (1H, d, J=8.5 Hz), 7.70–7.90 (3H, m), 9.82 (1H, brs); MS: 460 (M+H)$^+$. [α]$_D^{23.6}$: +19.0° (C=0.50, EtOH).
(3) 1-[(R)-4-(6-Hexanoylaminoindol-1-yl)-1-hydroxy-2-butyl]imidazole-4-carboxamide (96.6 mg, 80.9%)

mp: amorphous (86° C. decompose); IR (KBr): 3600–3000, 2954, 2929, 2863, 1656, 1590, 1259 cm$^{-1}$; NMR (DMSO-d$_6$, δ): 0.89 (3H, t, J=6.5 Hz), 1.20–1.45 (4H, m), 1.61 (2H, qui, J=7.0 Hz), 2.20–2.40 (4H, m), 3.60 (2H, t, J=5.2 Hz), 3.85–4.25 (3H, m), 5.06 (1H, t, J=5.2 Hz), 6.35 (1H, d, J=3.1 Hz), 7.00–7.15 (2H, m), 7.16 (1H, d, J=3.1 Hz), 7.29 (1H, brs), 7.42 (1H, d, J=8.5 Hz), 7.74 (1H, s), 7.78 (1H, s), 7.84 (1H, s), 9.80 (1H, brs); MS: 412 (M+H)$^+$; [α]$_D^{26.2}$: +25.80° (C=0.50, EtOH).

EXAMPLE 7

These compounds were prepared by a similar procedure to that of Example 5.
(1) 1-[(R)-1-(tert-Butyldimethylsilyloxy)-4-(6-(4-phenylbutyrylamino)indol-1-yl)-2-butyl]imidazole-4-carboxamide (170.6 mg, 100%)

IR (KBr): 3600–3000, 2935, 2858, 1662, 1590, 1255, 1128, 840 cm$^{-1}$; NMR (CDCl$_3$, δ): −0.10 (3H, s), −0.08 (3H, s), 0.80 (9H, s), 2.00–2.20 (2H, m), 2.20–2.50 (4H, m), 2.75 (2H, t, J=7.4 Hz), 3.60–4.25 (5H, m), 5.34 (1H, brs), 6.45 (1H, d, J=3.2 Hz), 6.86 (1H, d, J=3.2 Hz), 6.90–7.10 (2H, m), 7.15–7.40 (5H, m), 7.40–7.70 (5H, m); MS: 574 (M+H)$^+$; [α]$_D^{22.5}$: +15.10° (C=0.50, EtOH).
(2) 1-[(R)-1-(tert-Butyldimethylsilyloxy)-4-(6-hexanoylaminoindol-1-yl)-2-butyl]imidazole-4-carboxamide (170.6 mg, 100%)

IR (KBr): 3600–3000, 2954, 2933, 2859, 1660, 1592, 1255, 1126, 840 cm$^{-1}$; NMR (CDCl$_3$, δ): −0.10 (3H, s), −0.08 (3H, s), 0.80 (9H, s), 0.93 (3H, t, J=6.6 Hz), 1.30–1.50 (4H, m), 1.70–1.90 (2H, m), 2.20–2.50 (4H, m), 3.60–4.25 (5H, m), 5.43 (1H, brs), 6.45 (1H, d, J=3.1 Hz), 6.84 (1H, d, J=3.1 Hz), 6.95–7.10 (2H, m), 7.45–7.60 (3H, m), 7.63 (1H, s), 7.75 (1H, s); MS: 526 (M+H)$^+$; $[\alpha]_D^{24.0}$: +19.90° (C=0.50, EtOH).

EXAMPLE 8

These compounds were prepared by a similar procedure to that of Example 5.

(1) 1-[(R)-1-(tert-Butyldimethylsilyloxy)-4-(6-(5-phenylbutyrylamino)indol-1-yl)-2-butyl]imidazole-4-carboxamide (82.4 mg, 100%)

IR (KBr): 3600–3000, 2933, 2857, 1664, 1592, 1257, 1128, 840 cm$^{-1}$; NMR (CDCl$_3$, δ): −0.10 (3H, s), −0.08 (3H, s), 0.80 (9H, s), 1.60–1.95 (4H, m), 2.20–2.55 (4H, m), 2.69 (2H, t, J=7.0 Hz), 3.60–4.25 (5H, m), 5.37 (1H, brs), 6.45 (1H, d, J=3.2 Hz), 6.85 (1H, d, J=3.2 Hz), 6.90–7.10 (2H, m), 7.10–7.35 (5H, m), 7.40–7.60 (3H, m), 7.70 (1H, s), 7.78 (1H, s); MS: 588 (M+H)$^+$; $[\alpha]_D^{21.0}$: +16.60° (C=0.50, EtOH).

(2) In This Case 1-(3-Dimethylaminopropyl)-3-ethylcarbodiimide Hydrochloride was Added Instead of 1-(3-Dimethylaminopropyl)-3-ethylcarbodiimide. 1-[(R)-1-(tert-Butyldimethylsilyloxy)-4-(6-(3-(1-methylbenzimidazol-2-yl)propionylamino)indol-1-yl)-2-butyl]imidazole-4-carboxamide (95.9 mg, 77.3%)

IR (KBr): 3600–3000, 2935, 1664, 1594, 1253, 1126, 840 cm$^{-1}$; NMR (CDCl$_3$, δ): −0.11 (3H, s), −0.09 (3H, s), 0.79 (9H, s), 2.15–2.55 (2H, m), 3.05–3.40 (4H, m), 3.55–4.20 (8H, m), 5.88 (1H, brs), 6.42 (1H, d, J=3.0 Hz), 6.82 (1H, d, J=3.0 Hz), 6.95–7.10 (2H, m), 7.20–7.40 (3H, m), 7.46 (1H, s) 7.48 (1H, d, J=8.7 Hz), 7.60–7.80 (3H, m), 9.50 (1H, brs); MS: 614 (M+H)$^+$; $[\alpha]_D^{23.9}$: +9.20° (C=0.50, EtOH)

(3) 1-[(R)-1-(tert-Butyldimethylsilyloxy)-4-(6-(4-(4-methylphenyl)butyrylamino)indol-1-yl)-2-butyl]imidazole-4-carboxamide (103 mg, 78.9%)

IR (KBr): 3600–3000, 2933, 2857, 1664, 1592, 1253 cm$^{-1}$; NMR (CDCl$_3$, δ): −0.10 (3H, s), −0.08 (3H, s), 0.80 (9H, s), 1.95–2.20 (2H, m), 2.20–2.50 (7H, m), 2.71 (2H, t, J=7.4 Hz), 3.50–4.25 (5H, m), 5.37 (1H, brs), 6.45 (1H, d, J=3.0 Hz), 6.85 (1H, d, J=3.0 Hz), 6.90–7.20 (6H, m), 7.40–7.70 (5H, m); MS: 588 (M+H)$^+$; $[\alpha]_D^{24.9}$: +14.70° (C=0.50, EtOH).

(4) 1-[(R)-1-(tert-Butyldimethylsilyloxy)-4-(6-(3-(1,3-dioxo-1,3-dihydroisoindol-2-yl)propionylamino)indol-1-yl)-2-butyl]imidazole-4-carboxamide (110 mg, 78.5%)

IR (KBr): 3600–3000, 2935, 2857, 1714, 1664, 1592 cm$^{-1}$; NMR (CDCl$_3$, δ): −0.10 (3H, s), −0.08 (3H, s), 0.81 (9H, s), 2.20–2.50 (4H, m), 2.80–3.00 (2H, m), 3.60–4.25 (7H, m), 5.83 (1H, brs), 6.45 (1H, d, J=3.1 Hz), 6.89 (1H, d, J=3.1 Hz), 7.04 (1H, brs), 7.20–7.60 (4H, m), 7.63 (1H, s), 7.65–7.90 (4H, m), 30 8.19 (1H, brs); MS: 629 (M+H)$^+$; $[\alpha]_D^{24.6}$: +13.90° (C=0.50, EtOH).

(5) 1-[(R)-1-(tert-Butyldimethylsilyloxy)-4-(6-(3-(4-methoxyphenyl)propionylamino)indol-1-yl)-2-butyl]imidazole-4-carboxamide (105 mg, 80.2%)

IR (KBr): 3600–3000, 2950, 1664, 1592, 1247 cm$^{-1}$; NMR (CDCl$_3$, δ): −0.10 (3H, s), −0.08 (3H, s), 0.81 (9H, s), 2.20–2.55 (2H, m), 2.69 (2H, t, J=7.6 Hz), 3.04 (2H, t, J=7.6 Hz), 3.55–4.20 (10H, m), 5.44 (1H, brs), 6.45 (1H, d, J=3.0 Hz), 6.75–7.05 (5H, m), 7.15–7.25 (2H, m), 7.40–7.65 (5H, m), MS: 590 (M+H)$^+$; $[\alpha]_D^{26.7}$: +16.80° (C=0.50, EtOH).

(6) 1-[(R)-1-(tert-Butyldimethylsilyloxy)-4-(6-(3-(4-methylphenyl)propionylamino)indol-1-yl)-2-butyl]imidazole-4-carboxamide (103 mg, 80.7%)

IR (KBr): 3600–3000, 2931, 2857, 1664, 1592, 1251 cm$^{-1}$; NMR (CDCl$_3$, δ): −0.10 (3H, s), −0.08 (3H, s), 0.81 (9H, s), 2.20–2.55 (5H, m), 2.71 (2H, t, J=7.6 Hz), 3.05 (2H, t, J=7.6 Hz), 3.60–4.20 (5H, m), 5.42 (1H, brs), 6.45 (1H, d, J=3.0 Hz), 6.85 (1H, d, J=3.0 Hz), 6.90–7.25 (6H, m), 7.40–7.70 (5H, m); MS: 574 (M+H)$^+$; $[\alpha]_D^{26.4}$: +16.40° (C=0.50, EtOH).

EXAMPLE 9

These compounds were prepared by a similar procedure to that of Example 2.

(1) 1-[(R)-1-Hydroxy-4-(6-(5-phenylvalerylamino)indol-1-yl)-2-butyl]imidazole-4-carboxamide (54.1 mg, 70.3%)

mp: amorphous; IR (KBr): 3600–3000, 1664, 1656, 1592, 1259 cm$^{-1}$; NMR (DMSO-d$_6$, δ): 1.50–1.75 (4H, m), 2.10–2.45 (4H, m), 2.50–2.75 (2H, m), 3.59 (2H, t, J=5.2 Hz), 3.80–4.20 (3H, m), 5.06 (1H, t, J=5.2 Hz), 6.36 (1H, d, J=2.8 Hz), 6.95–7.35 (9H, m), 7.43 (1H, d, J=8.5 Hz), 7.70–7.90 (3H, m), 9.82 (1H, brs); MS: 474 (M+H)$^+$; $[\alpha]_D^{27.3}$: +19.00° (C=0.50, EtOH).

(2) 1-[(R)-1-Hydroxy-4-(6-(3-(1-methylbenzimidazol-2-yl)-propionylamino)indol-1-yl)-2-butyl]imidazole-4-carboxamide (69 mg, 91.5%)

mp: amorphous (110–113° C.); IR (KBr): 3700–2800, 1671, 1666, 1590 cm$^{-1}$; NMR (DMSO-d$_6$, δ): 2.20–2.40 (2H, m), 2.96 (2H, t, J=7.5 Hz), 3.20 (2H, t, J=7.5 Hz), 3.59 (2H, t, J=5.2 Hz), 3.79 (3H, s), 3.90–4.20 (3H, m), 5.05 (1H, t, J=5.2 Hz), 6.36 (1H, d, J=3.0 Hz), 7.00–7.35 (6H, m), 7.40–7.60 (3H, m), 7.77 (1H, s), 7.78 (1H, s), 7.86 (1H, s), 10.04 (1H, brs); MS: 500 (M+H)$^+$; $[\alpha]_D^{25.7}$: +10.20° (C=0.50, EtOH).

(3) 1-[(R)-1-Hydroxy-4-(6-(4-(4-methylphenyl)butyrylamino)indol-1-yl)-2-butyl]imidazole-4-carboxamide (63.8 mg, 82.5%)

mp: amorphous; IR (KBr): 3700–3000, 2931, 1656, 1590, 1238 cm$^{-1}$; NMR (DMSO-d$_6$, δ): 1.80–2.00 (2H, m), 2.20–2.40 (7H, m), 2.60 (2H, t, J=7.5 Hz), 3.60 (2H, d, J=5.2 Hz), 3.90–4.25 (3H, m), 5.08 (1H, brs), 6.36 (1H, d, J=3.0 Hz), 7.00–7.25 (7H, m), 7.40 (1H, brs), 7.42 (1H, d, J=8.5 Hz), 7.75–8.00 (3H, m), 9.81 (1H, brs); MS: 474 (M+H)$^+$; $[\alpha]_D^{27.4}$: +13.00° (C=0.50, EtOH).

(4) 1-[(R)-1-Hydroxy-4-(6-(3-(1,3-dioxo-1,3-dihydroisoindol-2-yl)propionylamino)indol-1-yl)-2-butyl]imidazole-4-carboxamide (45.5 mg, 54.5%)

mp: amorphous; IR (KBr): 3700–2800, 2956, 1710, 1658, 1592 cm$^{-1}$; NMR (DMSO-d$_6$, δ): 2.20–2.40 (2H, m), 2.70 (2H, t, J=7.2 Hz), 3.60 (2H, t, J=5.2 Hz), 3.80–4.20 (5H, m), 5.06 (1H, t, J=5.2 Hz), 6.36 (1H, d, J=3.0 Hz), 6.90–7.10 (2H, m), 71.7 (1H, d, J=3.0 Hz), 7.29 (1H, brs), 7.43 (1H, d, J=8.5 Hz), 7.60–7.95 (7H, m), 9.97 (1H, brs); MS: 515 (M+H)$^+$; $[\alpha]_D^{27.6}$: +15.10° (C=0.50, EtOH).

(5) 1-[(R)-1-Hydroxy-4-(6-(3-(4-methoxyphenyl)propionylamino)indol-1-yl)-2-butyl]imidazole-4-carboxamide (67 mg, 85.6%)

mp: amorphous; IR (KBr): 3700–3000, 2931, 1656, 1590, 1241 cm$^{-1}$; NMR (DMSO-d$_6$, δ): 2.20–2.40 (2H, m), 2.59 (2H, t, J=7.5 Hz), 2.87 (2H, t, J=7.5 Hz), 3.60 (2H, t, J=5.2 Hz), 3.71 (3H, s), 3.90–4.20 (3H, m), 5.06 (1H, t, J=5.2 Hz), 6.36 (1H, d, J=3.0 Hz), 6.85 (2H, d, J=8.6 Hz), 7.00–7.25 (5H, m), 7.28 (1H, brs), 7.43 (1H, d, J=8.5 Hz), 7.70–7.90 (3H, m), 9.83 (1H, brs); MS: 476 (M+H)$^+$; $[\alpha]_D^{27.6}$: +17.10° (C=0.50, EtOH).

(6) 1-[(R)-1-Hydroxy-4-(6-(3-(4-methylphenyl)propionylamino)indol-1-yl)-2-butyl]imidazole-4-carboxamide (71 mg, 92.5%)

mp: amorphous; IR (KBr): 3600–3000, 2927, 1656, 1590 cm$^{-1}$; NMR (DMSO-d$_6$, δ): 2.10–2.40 (5H, m), 2.60 (2H, t, J=7.5 Hz), 2.89 (2H, t, J=7.5 Hz), 3.61 (2H, t, J=5.2 Hz), 3.85–4.25 (3H, m), 5.08 (1H, brs), 6.36 (1H, d, J=3:.0 Hz), 6.95–7.25 (7H, m), 7.41 (1H, brs), 7.43 (1H, d, J=8.5 Hz), 7.70–8.00 (3H, m), 9.84 (1H, brs); MS: 460 (M+H)$^+$; $[\alpha]_D^{27.5}$: +11.90° (C=0.50, EtOH).

EXAMPLE 10

To an ice cooled solution of guanidine hydrochloride (216 mg, 2.26 mmol) in DMF (5 ml) was added a solution of 28% NaOMe in methanol (437 mg, 2.26 mmol). After 10 minutes, 1-[(R)-1-(tert-butyldimethylsilyloxy)-4-(3-methylindol-1-yl)-2-butyl]imidazole-4-carboxylate (150 mg, 0.340 mmol) in DMF (6 ml) was added to the mixture and the resulting mixture was stirred at 100° C. for 8 hours. After cooling, the reaction mixture was poured into water (30 ml) and the solution was extracted with ethyl acetate. The organic layer was washed with brine, dried (magnesium sulfate), and concentrated in vacuo. This material was used for the next reaction without further purification. To an ice cooled solution of the carboxamide prepared above (103 mg) in THF (10 ml) was added dropwise 1.0 M Bu$_4$NF in THF (340 ml). After the addition was completed, the reaction mixture was stirred at ice-bath temperature for 1 hour. 25% AcONH$_4$ (5 ml) was added, and the resulting mixture was stirred for several minutes. The solution was washed with ethyl acetate. The aqueous layer was purified by HP-20 (40 cc) column chromatography eluting with water/2-propanol (9:1) and lyophilized to give 1-[(R)-1-hydroxy-4-(3-methylindol-1-yl)-2-butyl]imidazole-4-carboxylguanidine (67.3 mg, 55.9%).

mp: amorphous (137–140° C.); IR (Neat): 3600–2700, 1702, 1592 cm$^{-1}$; NMR (CDCl$_3$, δ): 2.05–2.40 (5H, m), 3.50–4.20 (5H, m), 5.06 (1H, brs), 6.90–7.15 (4H, m), 7.22 (1H, d, J=7.9 Hz), 7.48 (1H, d, J=7.4 Hz), 7.85 (1H, s), 8.01 (1H, s); MS: 355 (M+H)$^+$; [α]$_D^{26.7}$: +49.70° (C=0.50, EtOH).

EXAMPLE 11

To a solution of 1-[(R)-1-(tert-butyldimethylsilyloxy)-4-(3-methylindol-1-yl)-2-butyl]imidazol-4-carboxylate (200 mg, 0.45 mmol) in DMF (5 ml) were added ammonium chloride (6 mg, 0.11 mmol) and aqueous 28% NH$_3$ solution (10 ml). And the mixture was heated at 100° C. in a sealed steel tube for 8 hours. After cooling, the reaction mixture was poured into water (50 ml) and extracted with ethyl acetate. The organic layer was washed with brine, dried (magnesium sulfate), and concentrated in vacuo. This material was used for the next reaction without further purification. To an ice cooled solution of the carboxamide prepared above (184 mg) in THF (10 ml) was added dropwise 1.0 M Bu$_4$NF in THF (453 ml). After the addition was completed, the reaction mixture was stirred at ice-bath temperature for 1 hour. 25% AcONH$_4$ (5 ml) was added, and the resulting mixture was stirred for several minutes and then extracted with ethyl acetate. The organic layer was washed with brine, dried (sodium sulfate) and concentrated in vacuo. The residue was triturated with a mixed solvent of isopropyl ether and chloroform (20:1). The resulting precipitates were collected by filtration and washed with the same mixed solvent, and dried in vacuo to give 1-[(R)-1-hydroxy-4-(3-methylindol-1-yl)-2-butyl]-imidazole-4-carboxamide (146 mg, 103%) as a white solid.

mp: amorphous (108–111° C.); IR (KBr): 3700–2800, 1664, 1583, 1238 cm$^{-1}$; NMR (CDCl$_3$, δ): 2.10–2.35 (5H, m), 3.59 (2H, t, J=5.5 Hz), 3.80–4.20 (3H, m), 5.03 (1H, t, J=5.3 Hz), 6.95–7.17 (4H, m), 7.22 (1H, d, J=7.8 Hz), 7.29 (1H, brs), 7.48 (1H, d, J=7.3 Hz), 7.68 (1H, s), 7.78 (1H, s); MS: 313 (M+H)$^+$.

PREPARATION 9

These compounds were prepared by a similar procedure to that of Example 8(2).

(1) 1-{(R)-1-(tert-Butyldimethylsilyloxy)-4-[6-(3-(3-pyridyl)propionylamino)indol-1-yl]-2-butyl}imidazole-4-carboxamide (103 mg, 82.8%)

IR (KBr): 3600–3000, 2950, 2933, 2858, 1664, 1593, 1255, 1126, 840 cm$^{-1}$; NMR (CDCl$_3$, δ): −0.09 (3H, s), −0.07 (3H, s), 0.81 (9H, s), 2.20–2.50 (2H, m), 2.76 (2H, t, J=8 Hz), 3.11 (2H, t, J=8 Hz), 3.55–4.20 (5H, m), 5.46 (1H, brs), 6.46 (1H, d, J=3 Hz), 6.89 (1H, d, J=3 Hz), 7.00 (1H, brs), 7.10–7.30 (2H, m), 7.40–7.70 (5H, m), 7.89 (1H, brs), 8.40–8.60 (2H, m); MS: 561 (M+H)$^+$; [α]$_D^{26.3}$=+13.30° (C=0.50, EtOH).

(2) 1-[(R)-1-(tert-Butyldimethylsilyloxy)-4-(6-(6-phenylhexanoylamino)indol-1-yl)-2-butyl]imidazole-4-carboxamide (73.7 mg, 74.8%)

IR (KBr): 3600–3000, 2931, 2858, 1658, 1593, 1493, 1255, 840 cm$^{-1}$; NMR (CDCl$_3$, δ): −0.10 (3H, s), −0.08 (3H, s), 0.80 (9H, s), 1.40–1.95 (6H, m), 2.20–2.50 (4H, m), 2.64 (2H, t, J=8 Hz), 3.55–4.25 (5H, m), 5.42 (1H, brs), 6.45 (1H, d, J=3 Hz), 6.85 (1H, d, J=3 Hz), 6.90–7.35 (7H, m), 7.45–7.75 (5H, m), MS: 602 (M+H)$^+$; [α]$_D^{22.5}$=+15.90° (C=0.50, EtOH).

(3) 1-[(R)-1-(tert-Butyldimethylsilyloxy)-4-(6-acetylaminoindol-1-yl)-2-butyl]imidazole-4-carboxamide (69.4 mg, 90.3%)

IR (KBr): 3600–3000, 2951, 2935, 1664, 1595, 1259, 1126, 840 cm$^{-1}$; NMR (CDCl$_3$, δ): −0.10 (3H, s), −0.08 (3H, s), 0.80 (9H, s), 2.23 (3H, s), 2.30–2.50 (2H, m), 3.60–4.20 (5H, m), 5.51 (1H, brs), 6.46 (1H, d, J=3 Hz), 6.88 (1H, d, J=3 Hz), 7.00–7.15 (2H, m), 7.40–7.75 (5H, m); MS: 470 (M+H)$^+$; [α]$_D^{2.7}$=+16.30° (C=0.50, EtOH).

(4) 1-{(R)-1-(tert-Butyldimethylsilyloxy)-4-[6-((2-benzothiazolylthio)acetylamino)indol-1-yl]-2-butyl}imidazole-4-carboxamide (118 mg, 83.9%)

IR (KBr): 3700–3000, 2931, 1660, 1593, 1249, 840 cm$^{-1}$; NMR (CDCl$_3$, δ): −0.12 (3H, s), −0.10 (3H, s), 0.79 (9H, s), 2.20–2.60 (2H, m), 3.55–4.30 (7H, m), 5.39 (1H, brs), 6.42 (1H, d, J=3 Hz), 6.75–6.90 (2H, m), 6.99 (1H, brs), 7.30–7.60 (4H, m), 7.65 (1H, s), 7.82 (1H, d, J=8 Hz), 7.95–8.10 (2H, m), 10.06 (1H, brs); MS: 635 (M+H)$^+$; [α]$_D^{28.1}$=+3.10° (C=0.50, EtOH).

(5) 1-[(R)-1-(tert-Butyldimethylsilyloxy)-4-(3-methyl-6-(4-phenylbutyrylamino)indol-1-yl)-2-butyl]imidazole-4-carboxamide (67.4 mg, 72.4%)

IR (KBr): 3600–3000, 2933, 2860, 1664, 1593, 1254, 1128, 841 cm$^{-1}$; NMR (CDCl$_3$, δ): −0.11 (3H, s), −0.09 (3H, s), 0.80 (9H, s), 2.00–2.50 (9H, m), 2.75 (2H, t, J=7 Hz), 3.50–4.20 (5H, m), 5.42 (1H, brs), 6.63 (1H, s), 6.90–7.65 (12H, m); MS: 588 (M+H)$^+$; [α]$_D^{25.1}$=+14.90° (C=0.50, EtOH).

(6) 1-{(R)-1-(tert-Butyldimethylsilyloxy)-4-[3-methyl-6-(3-(1-methylbenzimidazol-2-yl)propionylamino)indol-1-yl]-2-butyl}imidazole-4-carboxamide (123 mg, 72.1%)

IR (KBr): 3600–3000, 2933, 2858, 1666, 1595, 1254, 1124, 841 cm$^{-1}$; NMR (CDCl$_3$, δ): −0.11 (3H, s), −0.09 (3H, s), 0.80 (9H, s), 2.15–2.50 (5H, m), 3.05–3.40 (4H, m), 3.55–4.10 (8H, m), 5.84 (1H, brs), 6.60 (1H, s), 7.03 (1H, brs), 7.06 (1H, dd, J=9 Hz, 2 Hz), 7.20–7.80 (8H, m), 9.39 (1H, s); MS: 628 (M+H)$^+$; [α]$_D^{25.0}$=+7.70° (C=0.50, EtOH).

(7) 1-[(2S,3R)-2-Benzyloxy-5-[6-(4-phenylbutyrylamino)indol-1-yl]-3-pentyl]imidazole-4-carboxamide (86.3 mg, 79.7%)

IR (KBr): 3600–2800, 1658, 1591, 1250, 1090 cm$^{-1}$; NMR (CDCl$_3$, δ): 1.03 (3H, d, J=6 Hz), 2.00–2.85 (8H, m), 3.45–4.15 (4H, m), 4.31 (1H, d, J=12 Hz), 4.52 (1H, d, J=12

Hz), 5.38 (1H, brs), 6.44 (1H, d, J=3 Hz), 6.85 (1H, d, J=3 Hz), 6.98 (1H, brs), 7.05–7.70 (16H, m); MS: 564 (M+H)⁺; [α]$_D^{27.0}$=+17.10° (C=0.50, EtOH).

(8) 1-{(2S,3R)-2-Benzyloxy-5-[6-(3-(1-methylbenzimidazol-2-yl)propionylamino)indol-1-yl]-3-pentyl}imidazole-4-carboxamide (138 mg, 83.1%)

IR (KBr): 3700–2800, 1660, 1593, 1547, 1240, 1092 cm⁻¹; NMR (CDCl₃, δ): 1.01 (3H, d, J=6 Hz), 2.00–2.70 (2H, m), 3.05–3.40 (4H, m), 3.50–4.10 (7H, m), 4.29 (1H, d, J=12 Hz), 4.50 (1H, d, J=12 Hz), 6.08 (1H, brs), 6.41 (1H, d, J=3 Hz), 6.82 (1H, d, J=3 Hz), 6.95–7.55 (13H, m), 7.60–7.85 (2H, m), 9.49 (1H, brs); MS: 604 (M+H)⁺; [α]$_D^{26.9}$=+12.10° (C=0.50, EtOH).

PREPARATION 10

To a solution of 1-[(R)-4-(6-aminoindol-1-yl)-1-(tert-butyldimethylsilyloxy)-2-butyl]imidazole-4-carboxamide (100 mg, 0.234 mmol) in THF (5 ml) was added dropwise benzylisocyanate (32 µl, 0.257 mmol). The reaction mixture was stirred at room temperature for 2 hours and the solvent was concentrated in vacuo. The residue was purified by silica gel (4.5 g) column chromatography eluting with chloroform/methanol (30:1) to give 1-[(R)-4-(6-(3-benzylureido)indol-1-yl)-1-(tert-butyldimethylsilyloxy)-2-butyl]imidazole-4-carboxamide (101 mg, 77%) as a pale yellow solid.

IR (KBr): 3600–3000, 2933, 2858, 1654, 1590, 1252, 1126, 840 cm⁻¹; NMR (CDCl₃, δ): −0.10 (3H, s), −0.08 (3H, s), 0.81 (9H, s), 2.20–2.40 (2H, m), 3.55–4.10 (5H, m), 4.47 (2H, d, J=6 Hz), 5.39 (1H, brs), 5.66 (1H, t, J=6 Hz), 6.44 (1H, d, J=3 Hz), 6.85–6.92 (2H, m), 7.01 (1H, brs), 7.15–7.40 (7H, m), 7.40–7.65 (3H, m); MS: 561 (M+H)⁺; [α]$_D^{26.4}$=+17.90° (C=0.50, EtOH).

PREPARATION 11

This compound was prepared by a similar procedure to that of Preparation 10.
1-[(R)-1-(tert-Butyldimethylsilyloxy)-4-(6-(3-phenethylureido)indol-1-yl)-2-butyl]imidazole-4-carboxamide (170.6 mg, 100%)

IR (KBr): 3600–3000, 2933, 2858, 1657, 1593, 1552, 1252, 1126, 840 cm⁻¹; NMR (CDCl₃, δ): −0.10 (3H, s), −0.08 (3H, s), 0.81 (9H, s), 2.20–2.40 (2H, m), 2.87 (2H, t, J=7 Hz), 3.50–4.05 (7H, m), 5.22 (1H, brs), 5.29 (1H, t, J=6 Hz), 6.44 (1H, d, J=3 Hz), 6.76 (1H, s), 6.88 (1H, d, J=3 Hz), 6.94 (1H, brs), 7.10–7.70 (10H, m); MS: 575 (M+H)⁺; [α]$_D^{25.9}$=+16.90° (C=0.50, EtOH).

PREPARATION 12

Under N₂, to a stirred solution of 1-[(R)-4-(6-aminoindol-1-yl)-1-(tert-butyldimethylsilyloxy)-2-butyl]imidazole-4-carboxamide (164 mg, 0.383 mmol) in dichloromethane (10 ml) was added hydrocinnamaldehyde (51 mg, 0.383 mmol) at room temperature. The mixture was stirred for 30 minutes. Sodium triacetoxyborohydride (114 mg, 0.536 mmol) was added to the mixture at room temperature and the resulting mixture was stirred for 5 hours. And then the reaction mixture was partitioned between dichloromethane and water. The organic layer was washed with brine, dried (sodium sulfate), and concentrated in vacuo. The residue was purified by silica gel (10 g) column chromatography eluted with chloroform/methanol (100:1 to 10:1) to give 1-[(R)-1-(tert-butyldimethylsilyloxy)-4-(6-(3-phenylpropylamino)indol-1-yl)-2-butyl]imidazole-4-carboxamide (52.6 mg, 25.2%).

IR (Neat): 3600–3000, 2933, 2858, 1666, 1593, 1255, 1126, 1095, 839 cm⁻¹; NMR (CDCl₃, δ): −0.10 (3H, s), −0.08 (3H, s), 0.81 (9H, s), 1.90–2.55 (4H, m), 2.78 (2H, t, J=8 Hz), 3.05–4.20 (7H, m), 5.41 (1H, brs), 6.20 (1H, d, J=2 Hz), 6.37 (1H, d, J=3 Hz), 6.48 (1H, dd, J=9 Hz, 2 Hz), 6.67 (1H, d, J=3 Hz), 6.97 (1H, brs), 7.02–7.50 (8H, m), 7.68 (1H, s); MS: 546 (M+H)⁺.

PREPARATION 13

These compounds were prepared by a similar procedure to that of Preparation 2.

(1) 1-[2-((4S)-2,2-Dimethyl-1,3-dioxolan-4-yl)ethyl]-1H-3-methyl-6-nitroindole (1.91 g, 71.5%)

IR (Neat): 2960, 2929, 2867, 1236, 1080 cm⁻¹; NMR (CDCl₃, δ): 1.34 (3H, s), 1.47 (3H, s), 1.90–2.20 (2H, m), 2.34 (3H, s), 3.40–4.10 (3H, m), 4.33 (2H, dd, J=8 Hz, 6 Hz), 7.19 (1H, s), 7.58 (1H, d, J=9 Hz), 8.00 (1H, dd, J=9 Hz, 2 Hz), 8.36 (1H, d, J=2.0 Hz); MS: 305 (M+H)⁺.

(2) 1-[(3S,4S)-4-Benzyloxy-3-(tert-butyldimethylsilyloxy)pentyl]-6-nitroindole (3.43 g, 72.9%)

IR (Neat): 2935, 2858, 1333, 1242, 1093, 837 cm⁻¹; NMR (CDCl₃, δ): 0.00 (3H, s), 0.04 (3H, s), 0.93 (9H, s), 1.15 (3H, d, J=6 Hz), 1.75–2.35 (2H, m), 3.40 (2H, m), 3.95–4.50 (3H, m), 4.60 (1H, d, J=12 Hz), 6.58 (1H, d, J=3 Hz), 7.15–7.45 (6H, m), 7.65 (1H, d, J=9 Hz), 8.01 (1H, dd, J=9 Hz, 2 Hz), 8.33 (1H, d, J=2 Hz); MS: 469 (M+H)⁺.

(3) In This Case 1-[(2S,3R)-2-Benzyloxy-5-hydroxy-3-pentyl]imidazole-4-carboxamide was Added Instead of 2-[(4S)-2,2-Dimethyl-1,3-dioxolan-4-yl]ethanol. 1-[(2S,3R)-2-Benzyloxy-5-(indol-1-yl)-3-pentyl]imidazole-4-carboxamide (34.4 mg, 37.0%)

IR (Neat): 3700–3000, 2971, 2929, 1660, 1238, 1092 cm⁻¹; NMR (CDCl₃, δ): 1.00 (3H, d, J=6 Hz), 2.15–2.75 (2H, m), 3.45–4.25 (4H, m), 4.30 (1H, d, J=12 Hz), 4.52 (1H, d, J=12 Hz), 5.43 (1H, brs), 6.50 (1H, d, J=3 Hz), 6.87 (1H, d, J=3 Hz), 6.98 (1H, brs), 7.05–7.40 (9H, m), 7.55–7.75 (2H, m); MS: 403 (M+H)⁺.

(4) In This Case 3-Cyanoindole was Added instead of Indole. 1-(2S,3R)-2-Benzyloxy-5-(3-cyanoindol-1-yl)-3-pentyl]imidazole-4-carboxamide (73.9 mg, 95.5%)

IR (Neat): 3700–2800, 2218, 1658, 1531, 1259, 1095 cm⁻¹; NMR (CDCl₃, δ): 1.05 (3H, d, J=6 Hz), 2.15–2.75 (2H, m), 3.50–4.25 (4H, m), 4.33 (1H, d, J=12 Hz), 4.59 (1H, d, J=12 Hz), 5.45 (1H, brs), 6.98 (1H, brs), 7.05–7.45 (10H, m), 7.60–7.85 (2H, m); MS: 428 (M+H)⁺; [α]$_D^{27.5}$=+27.20° (C=0.50, EtOH).

(5) In This Case 6-Chloroindole was Added Instead of Indole. 1-[(2S,3R)-2-Benzyloxy-5-(6-chloroindol-1-yl)-3-pentyl]imidazole-4-carboxamide (89.6 mg, 73.2%)

IR (Neat): 3700–3000, 2972, 2933, 2873, 1664, 1600, 1458, 1238, 1097 cm⁻¹; NMR (CDCl₃, δ): 1.01 (3H, d, J=6 Hz), 2.10–2.75 (2H, m), 3.45–4.20 (4H, m), 4.42 (1H, d, J=12 Hz), 4.54 (1H, d, J=12 Hz), 5.44 (1H, brs), 6.47 (1H, d, J=3 Hz), 25 6.84 (1H, d, J=3 Hz), 7.00 (1H, brs), 7.05–7.45 (8H, m), 7.53 (1H, d, J=9 Hz), 7.66 (1H, s); MS: 437 (M+H)⁺ (³⁵Cl), 439 (M+H)⁺ (³⁷Cl); [α]$_D^{25.4}$=+22.20° (C=0.50, EtOH).

(6) In This Case 6-Benzyloxyindole was Added Instead of Indole. 1-[(2S,3R)-2-Benzyloxy-5-(6-benzyloxyindol-1-yl)-3-pentyl]imidazole-4-carboxamide (202 mg, 27.9%)

IR (Neat): 3600–3000, 2972, 2870, 1664, 1610, 1240, 1170, 1090 cm⁻¹; NMR (CDCl₃, δ): 1.00 (3H, d, J=6 Hz), 2.10–2.70 (2H, m), 3.45–4.20 (4H, m), 4.30 (1H, d, J=12 Hz), 4.52 (1H, d, J=12 Hz), 5.06 (2H, s), 5.36 (1H, brs), 6.43 (1H, d, J=3 Hz), 6.60 (1H, d, J=2 Hz), 6.77 (1H, d, J=3 Hz), 6.87 (1H, dd, J=9 Hz, 2 Hz), 6.96 (1H, brs), 7.15–7.60 (12H, m), 7.68 (1H, s); MS: 509 (M+H)⁺.

PREPARATION 14

These compounds were prepared by a similar procedure to that of Preparation 3.

(1) (S)-[1-(tert-Butyldimethylsilyloxy)-4-(3-methyl-6-nitroindol-1-yl)]-butan-2-ol (1.57 g, 84.8%)

IR (Neat): 3600–3200, 2929, 2857, 1508, 1469, 1336, 1248, 1082, 839 cm$^{-1}$; NMR (CDCl$_3$, δ): 0.04 (6H, s), 0.88 (9H, s), 1.80–2.00 (2H, m), 2.34 (3H, s), 2.49 (1H, d, J=4 Hz), 3.25–3.65 (3H, m), 4.36 (2H, dd, J=8 Hz, 6 Hz), 7.22 (1H, s), 7.57 (1H, d, J=9 Hz), 7.99 (1H, dd, J=9 Hz, 2 Hz), 8.34 (1H, d, J=2.0 Hz); MS: 379 (M+H)$^+$.

(2) (S)-4-(6-Benzyloxyindol-1-yl)-1-(tert-butyldimethylsilyloxy)butan-2-ol (2.12 g, 87.4%)

IR (Neat): 3566, 2952, 2860, 1540, 1238, 1086 cm$^{-1}$; NMR (CDCl$_3$, δ): 0.04 (6H, s), 0.88 (9H, s), 1.70–1.95 (2H, m), 2.41 (1H, brs), 3.25–3.65 (3H, m), 4.24 (2H, dd, J=8 Hz, 6 Hz), 5.13 (2H, s), 6.42 (1H, d, J=3 Hz), 6.86 (1H, dd, J=9 Hz, 2 Hz), 6.94 (1H, d, J=2 Hz), 7.03 (1H, d, J=3 Hz), 7.25–7.55 (6H, m); MS: 426 (M+H)$^+$.

(3) (S)-4-(5-Benzyloxyindol-1-yl)-1-(tert-butyldimethylsilyloxy)butan-2-ol (2.45 g, 88.0%)

IR (Neat): 3570, 2931, 2860, 1460, 1236, 1090, 840 cm$^{-1}$; NMR (CDCl$_3$, δ): 0.03 (6H, s), 0.88 (9H, s), 1.75–2.00 (2H, m), 2.47 (1H, brs), 3.25–3.65 (3H, m), 4.29 (2H, dd, J=7 Hz, 6 Hz), 5.10 (2H, s), 6.39 (1H, d, J=3 Hz), 6.95 (1H, dd, J=9 Hz, 2 Hz), 7.12 (1H, d, J=3 Hz), 7.17 (1H, d, J=2 Hz), 7.25–7.55 (6H, m); MS: 426 (M+H)$^+$.

(4) (S)-1-(tert-Butyldimethylsilyloxy)-4-(2-methylindol-1-yl)butan-2-ol (211 mg, 11.0%)

IR (Neat): 3700–3100, 2956, 2929, 2860, 1238, 1088 cm$^{-1}$; NMR (CDCl$_3$, δ): 0.04 (6H, s), 0.88 (9H, s), 1.70–1.95 (2H, m), 2.46 (3H, s), 2.50 (1H, brs), 3.36 (1H, dd, J=9 Hz, 7 Hz), 3.45–3.75 (2H, m), 4.27 (2H, t, J=7 Hz), 6.23 (1H, s), 6.95–7.25 (2H, m), 7.33 (1H, d, J=8 Hz), 7.51 (1H, d, J=6 Hz); MS: 334 (M+H)$^+$.

PREPARATION 15

These compounds were prepared by a similar procedure to that of Example 1.

(1) 1-[(R)-1-(tert-Butyldimethylsilyloxy)-4-(3-methyl-6-nitroindol-1-yl)-2-butyl]imidazole-4-carboxamide (488.8 mg, 25.4%)

IR (KBr): 3600–3000, 2933, 2858, 1664, 1336, 1254, 1119, 840 cm$^{-1}$; NMR (CDCl$_3$, δ): –0.08 (3H, s), –0.06 (3H, s), 0.81 (9H, s), 2.25–2.60 (5H, m), 3.65–4.35 (5H, m), 5.41 (1H, brs), 6.95 (1H, s), 6.96 (1H, brs), 7.38 (1H, s), 7.60 (1H, d, J=9 Hz), 7.65 (1H, s), 8.02 (1H, dd, J=9 Hz, 2.0 Hz), 8.12 (1H, d, J=2 Hz); MS: 472 (M+H)$^+$.

(2) 1-[(R)-4-(6-Benzyloxyindol-1-yl)-1-(tert-butyldimethylsilyloxy)-2-butyl]imidazole-4-carboxamide (982 mg, 42.2%)

IR (Neat): 3600–3000, 2939, 2860, 1666, 1254, 1124, 1093, 839 cm$^{-1}$; NMR (CDCl$_3$, δ): –0.10 (3H, s), –0.08 (3H, s), 0.81 (9H, s), 2.20–2.55 (2H, m), 3.55–4.25 (5H, m), 5.09 (2H, s), 5.38 (1H, brs), 6.44 (1H, d, J=3 Hz), 6.63 (1H, d, J=2 Hz), 6.79 (1H, d, J=3 Hz), 6.88 (1H, dd, J=9 Hz, 2 Hz), 6.96 (1H, brs), 7.30–7.55 (7H, m), 7.67 (1H, s); MS: 519 (M+H)$^+$; [α]$_D^{28.3}$=+8.70° (C=0.50, EtOH).

(3) 1-[(R)-4-(5-Benzyloxyindol-1-yl)-1-(tert-butyldimethylsilyloxy)-2-butyl]imidazole-4-carboxamide (515 mg, 33.1%)

NMR (CDCl$_3$, δ): –0.10 (3H, s), –0.08 (3H, s), 0.81 (9H, s), 2.20–2.40 (2H, m), 3.60–4.30 (5H, m), 5.11 (2H, s), 5.41 (1H, brs), 6.42 (1H, d, J=3 Hz), 6.86 (1H, d, J=3 Hz), 6.86 (1H, d, J=3 Hz), 6.96 (1H, dd, J=9 Hz, 2 Hz), 6.98 (1H, brs), 7.08 (1H, d, J=9 Hz), 7.17 (1H, d, J=2 Hz), 7.25–7.55 (6H, m), 7.67 (1H, s); MS: 519 (M+H)$^+$.

(4) 1-[(R)-1-(tert-Butyldimethylsilyloxy)-4-(1-methylindol-3-yl)-2-butyl]imidazole-4-carboxamide (290 mg, 37.6%)

IR (Neat): 3600–3000, 2991, 2935, 2858, 1668, 1593, 1471, 1255, 1124, 1090, 840 cm$^{-1}$; NMR (CDCl$_3$, δ): –0.08 (3H, s), –0.06 (3H, s), 0.82 (9H, s), 2.10–2.35 (2H, m), 2.45–2.90 (2H, m), 3.60–4.20 (6H, m), 5.38 (1H, brs), 6.75 (1H, s), 6.96 (1H, brs), 7.00–7.35 (3H, m), 7.45 (1H, s), 7.49 (1H, d, J=8 Hz), 7.66 (1H, s); MS: 427 (M+H)$^+$; [α]$_D^{28.7}$=+17.10° (C=0.50, EtOH).

(5) 1-[(R)-4-(5-Benzyloxy-1-methylindol-3-yl)-1-(tert-butyldimethylsilyloxy)-2-butyl]imidazole-4-carboxamide (3.10 g, 53.3%)

IR (Neat): 3700–3000, 2949, 2860, 1666, 1595, 1238, 1120, 1090, 839 cm$^{-1}$; NMR (CDCl$_3$, δ): –0.08 (3H, s), –0.06 (3H, s), 0.81 (9H, s), 2.05–2.25 (2H, m), 2.35–2.85 (2H, m), 3.55–4.15 (6H, m), 5.10 (2H, s), 5.35 (1H, brs), 6.71 (1H, s), 6.85–7.05 (3H, m), 7.10–7.55 (7H, m), 7.66 (1H, s); MS: 533 (M+H)$^+$; [α]$_D^{22.9}$=+14.40° (C=0.50, EtOH).

(6) 1-[(2S,3R)-2-Benzyloxy-5-(6-nitroindol-1-yl)-3-pentyl]imidazole-4-carboxamide (250 mg, 14.1%)

IR (Neat): 3600–3000, 2950, 1670, 1504, 1333, 1236, 1097 cm$^{-1}$; NMR (CDCl$_3$, δ): 1.03 (3H, d, J=6 Hz), 2.15–2.85 (2H, m), 3.50–3.80 (2H, m), 3.85–4.40 (3H, m), 4.56 (1H, d, J=12 Hz), 5.43 (1H, brs), 6.60 (1H, d, J=3 Hz), 6.98 (1H, brs), 7.12 (1H, d, J=3 Hz), 7.15–7.45 (6H, m), 7.65 (1H, s), 7.67 (1H, d, J=9 Hz), 8.03 (1H, dd, J=9 Hz, 2 Hz), 8.15 (1H, d, J=2 Hz); MS: 448 (M+H)$^+$.

(7) 1-[(2S,3R)-2-Benzyloxy-5-(tert-butyldimethylsilyloxy)-3-pentyl]imidazole-4-carboxamide (1.98 g, 28.2%)

IR (Neat): 3700–3000, 2958, 2860, 1655, 1238, 1090 cm$^{-1}$; NMR (CDCl$_3$, δ): –0.04 (3H, s), –0.02 (3H, s), 0.86 (9H, s), 1.13 (3H, d, J=6 Hz), 1.80–2.30 (2H, m), 3.24 (1H, m), 3.55–3.80 (2H, m), 4.32 (1H, m), 4.41 (1H, d, J=12 Hz), 4.61 (1H, d, J=12 Hz), 5.36 (1H, brs), 6.95 (1H, brs), 7.20–7.40 (5H, m), 7.44 (1H, s), 7.63 (1H, s); MS: 418 (M+H)$^+$.

(8) 1-[(R)-1-(tert-Butyldimethylsilyloxy)-4-(2-methylindol-1-yl)-2-butyl]imidazole-4-carboxamide (113 mg, 43.1%)

NMR (CDCl$_3$, δ): –0.09 (3H, s), –0.07 (3H, s), 0.82 (9H, s), 2.15–2.50 (5H, m), 3.60–4.15 (5H, m), 5.43 (1H, brs), 6.25 (1H, s), 6.90–7.25 (4H, m), 7.43 (1H, s), 7.51 (1H, dd, J=6 Hz, 2 Hz), 7.68 (1H, s); MS: 427 (M+H)$^+$.

(9) 1-[(2S,3R)-2-(Benzyloxy)-5-(1-naphthyl)-3-pentyl]-3-1,2,4-triazole

NMR (CDCl$_3$, δ): 1.02 (3H, d, J=6 Hz), 2.4–2.6 (2H, m), 2.7–3.0 (2H, m), 3.7–3.9 (1H, m), 4.2–4.6 (3H, m), 7.0–8.1 (12H, m), 8.05 (1H, s), 8.14 (1H, s); MS: 372 (M+H)$^+$.

(10) 1-[(2S,3R)-2-(Benzyloxy)-5-(1-naphthyl)-3-pentyl]-7-azabenzimidazole

NMR (CDCl$_3$, δ): 1.21 (3H, d, J=6 Hz), 2.5–3.0 (4H, m), 3.9–4.0 (1H, m), 4.3–4.9 (3H, m), 7.1–8.5 (16H, m); MS: 422 (M+H)$^+$.

(11) Ethyl 1-[(2S,3R)-2-(Benzyloxy)-5-(2,3-dichlorophenyl)-3-pentyl]-1,2,4-triazole-3-carboxylate NMR (CDCl$_3$, δ): 1.11 (3H, d, J=6 Hz), 1.46 (3H, t, J=7 Hz), 2.3–2.7 (4H, m), 3.8–3.9 (1H, m), 4.3–4.7 (5H, m), 6.9–7.4 (8H, m), 8.24 (1H, s); MS: 484 (M+Na)$^+$.

(12) Ethyl 1-[(2S,3R)-2-(Benzyloxy)-5-(2,3-dichlorophenyl)-3-pentyl]-1,2,4-triazole-5-carboxylate NMR (CDCl$_3$, δ): 0.99 (3H, d, J=6 Hz), 1.39 (3H, t, J=7 Hz), 2.3–2.8 (4H, m), 3.7–4.0 (1H, m), 4.3–4.7 (4H, m), 5.4–5.6 (1H, m), 6.9–7.4 (8H, m), 8.03 (1H, s); MS: 484 (M+Na)$^+$.

PREPARATION 16

These compounds were prepared by a similar procedure to that of Example 4.

(1) 1-[(R)-4-(6-Amino-3-methylindol-1-yl)-1-(tert-butyldimethylsilyloxy)-2-butyl]imidazole-4-carboxamide (264 mg, 94.0%).

IR (KBr): 3600–3000, 2931, 2858, 1664, 1625, 1597, 1255, 1128, 839 cm$^{-1}$; NMR (CDCl$_3$, δ): −0.10 (3H, s), −0.08 (3H, s), 0.81 (9H, s), 2.00–2.60 (5H, br), 3.55–4.15 (7H, m), 5.42 (1H, brs), 6.29 (1H, d, J=2 Hz), 6.50 (1H, s), 6.57 (1H, dd, J=8 Hz, 2 Hz), 6.99 (1H, brs), 7.32 (1H, d, J=8 Hz), 7.40 (1H, s), 7.67 (1H, s); MS: 442 (M+H)$^+$.

(2) 1-[(2S,3R)-5-(6-Aminoindol-1-yl)-2-benzyloxy-3-pentyl]imidazole-4-carboxamide (201 mg, 86.4%).

IR (KBr): 3700–3000, 1660, 1626, 1595, 1257, 1092 cm$^{-1}$; NMR (CDCl$_3$, δ): 1.02 (3H, d, J=6 Hz), 2.05–2.70 (2H, m), 3.40–4.20 (6H, m), 4.32 (1H, d, J=12 Hz), 4.53 (1H, d, J=12 Hz), 5.43 (1H, brs), 6.29 (1H, d, J=2 Hz), 6.37 (1H, d, J=3 Hz), 6.56 (1H, dd, J=9 Hz, 2 Hz), 6.70 (1H, d, J=3 Hz), 7.00 (1H, brs), 7.10–7.45 (7H, m), 7.69 (1H, s); MS: 418 (M+H)$^+$.

PREPARATION 17

To a stirred mixture of 2-[(4S)-2,2-dimethyl-1,3-dioxolan-4-yl]ethanol (50.89 g, 0.348 mol) and pyridine (113 ml, 1.39 mol) in dichloromethane (500 ml) was added gradually p-toluenesulfonyl chloride (79.65 g, 0.418 mmol) at ice-bath temperature. After removal of ice-bath, the reaction mixture was stirred at ambient temperature overnight. The mixture was poured into ice-cooled 1N-HCl (400 ml) and the mixture was extracted with dichloromethane. The organic layer was washed with saturated NaHCO$_3$ solution and brine, dried with MgSO$_4$, and concentrated in vacuo. The residue was purified by silica gel (800 g) column chromatography eluting with toluene/ethyl acetate (50:1 to 10:1) to give 2-((4S)-2,2-dimethyl-1,3-dioxolan-4-yl)ethyl p-toluenesulfonate (85.0 g, 81.3%) as an oil.

IR (Neat): 2985, 2935, 2879, 1599, 1456, 1358, 1236, 1180, 1097, 1059 cm$^{-1}$; NMR (CDCl$_3$, δ): 1.29 (3H, s), 1.34 (3H, s), 1.90 (2H, q, J=7 Hz), 2.45 (3H, s), 3.51 (1H, t, J=7 Hz), 3.95–4.30 (4H, m), 7.35 (2H, d, J=8 Hz), 7.80 (2H, d, J=8 Hz); MS: 301 (M+H)$^+$.

PREPARATION 18

Under N$_2$, to a solution of 6-benzyloxyindole (1.25 g, 5.58 mmol) in DMF (10 ml) was added NaH (60% in mineral oil, 245 mg, 6.13 mmol) at room temperature. The reaction mixture was stirred for 30 minutes. A solution of 2-((4S)-2,2-dimethyl-1,3-dioxolan-4-yl)ethyl p-toluenesulfonate (1.84 g, 6.13 mmol) in DMF (5 ml) was added and the resulting mixture was stirred for 2 hours at room temperature. The reaction mixture was cooled to 10° C. in an ice bath, and the insoluble material was filtered and washed thoroughly with ethyl acetate. The filtrate and the washing were combined and then washed with brine. The organic layer was dried (magnesium sulfate) and concentrated in vacuo. The residue was purified by silica gel (40 g) column chromatography eluting with toluene/ethyl acetate (50:1) to give 1-[2-((4S)-2,2-dimethyl-1,3-dioxolan-4-yl)ethyl]-1H-6-benzyloxyindole (2.01 g, 93.3%) as a colorless oil.

IR (Neat): 3031, 2937, 2873, 1238, 1080, 1053 cm$^{-1}$; NMR (CDCl$_3$, δ): 1.35 (3H, s), 1.45 (3H, s), 1.85–2.15 (2H, m), 3.35–4.30 (5H, m), 5.13 (2H, s), 6.42 (1H, d, J=3 Hz), 6.86 (1H, dd, J=9 Hz, 2 Hz), 6.92 (1H, d, J=2 Hz), 7.01 (1H, d, J=3 Hz), 7.25–7.55 (6H, m); MS: 352 (M+H)$^+$.

PREPARATION 19

These compounds were prepared by a similar procedure to that of Example 2.
(1) 1-[(R)-4-(6-Benzyloxyindol-1-yl)-1-hydroxy-2-butyl] imidazole-4-carboxamide (72 mg, 87.3%)

IR (KBr): 3600–2800, 1658, 1616, 1232, 1084 cm$^{-1}$; NMR (DMSO-d$_6$, δ): 2.10–2.35 (2H, m), 3.60 (2H, t, J=5 Hz), 3.80–4.20 (3H, m), 5.04 (1H, t, J=5 Hz), 5.09 (2H, s), 6.34 (1H, d, J=3 Hz), 6.74 (1H, dd, J=9 Hz, 2 Hz), 6.88 (1H, d, J=2 Hz), 7.06 (1H, brs), 7.13 (1H, d, J=3 Hz), 7.20–7.55 (7H, m), 7.70 (1H, s), 7.81 (1H, s); MS: 405 (M+H)$^+$.

(2) (3S,4S)-4-Benzyloxy-1-(6-nitroindol-1-yl)pentan-3-ol (1.40 g, 54.6%) IR (Neat): 3600–3000, 2962, 2927, 2868, 1593, 1238, 1086 cm$^{-1}$; NMR (CDCl$_3$, δ): 1.11 (3H, d, J=6 Hz), 1.70–2.15 (2H, m), 2.69 (1H, d, J=3 Hz), 3.20–3.45 (2H, m), 4.30–4.50 (3H, m), 4.65 (1H, d, J=12 Hz), 6.58 (1H, d, J=3 Hz), 7.20–7.50 (6H, m), 7.64 (1H, d, J=9 Hz), 8.00 (1H, dd, J=9 Hz, 2 Hz), 8.37 (1H, d, J=2 Hz) MS: 355 (M+H)$^+$.

(3) (3S,4S)-4-Benzyloxypentane-1,3-diol (2.2 g, 75.5%)

IR (Neat): 3700–3000, 2962, 2925, 2875, 1381, 1238, 1086 cm$^{-1}$; NMR (CDCl$_3$, δ): 1.20 (3H, d, J=6 Hz), 1.60–1.85 (2H, m), 2.66 (1H, t, J=6 Hz), 2.94 (1H, d, J=3 Hz), 3.30–3.95 (4H, m), 4.44 (1H, d, J=11 Hz), 4.69 (1H, d, J=11 Hz), 7.20–7.50 (5H, m); MS: 211 (M+H)$^+$.

(4) 1-[(2S,3R)-2-Benzyloxy-5-hydroxy-3-pentyl]imidazole-4-carboxamide (1.60 g, 96.9%)

IR (KBr): 3600–3000, 2958, 2860, 1649, 1597, 1421, 1338, 1265, 1103, 1066 cm$^{-1}$; NMR (CDCl$_3$, δ): 1.15 (3H, d, J=6 Hz), 1.80–2.40 (2H, m), 3.15–3.40 (2H, m), 3.55–3.85 (2H, m), 4.36 (1H, m), 4.42 (1H, d, J=12 Hz), 4.62 (1H, d, J=12 Hz), 5.45 (1H, brs), 6.98 (1H, brs), 7.20–7.40 (5H, m), 7.51 (1H, s), 7.66 (1H, s); MS: 304 (M+H)$^+$.

PREPARATION 20

To a solution of 1-[(R)-4-(6-Benzyloxyindol-1-yl)-1-(tert-butyldimethylsilyloxy)-2-butyl]imidazole-4-carboxamide (975 mg, 1.88 mmol) in cyclohexene (10 ml) and ethanol (20 ml) was added 20% palladium hydroxide on carbon (488 mg). The resulting mixture was stirred at reflux for 1 hour. After cooling to room temperature, the mixture was filtered through Celite and washed with ethanol. The filtrate was concentrated in vacuo and then the residue was purified by silica gel (20 g) chromatography eluted with chloroform/methanol (100:1 to 50:1) to give 1-[(R)-1-(tert-butyldimethylsilyloxy)-4-(6-hydroxyindol-1-yl)-2-butyl] imidazole-4-carboxamide (772 mg, 95.8%) as a colorless solid.

IR (KBr): 3700–3000, 2935, 1658, 1255, 1126, 839 cm$^{-1}$; NMR (CDCl$_3$, δ): −0.09 (3H, s), −0.07 (3H, s), 0.81 (9H, s), 2.20–2.55 (2H, m), 3.55–4.05 (5H, m), 5.64 (1H, brs), 6.43 (1H, d, J=3 Hz), 6.56 (1H, d, J=2 Hz), 6.74 (1H, dd, J=8 Hz, 2 Hz), 6.81 (1H, d, J=3 Hz), 7.06 (1H, brs), 7.44 (1H, d, J=8 Hz), 7.46 (1H, s), 7.73 (1H, s); MS: 429 (M+H)$^+$; [α]$_D^{26.0}$=+25.70° (C=0.50, EtOH).

PREPARATION 21

Under N$_2$, to a solution of 1-[(R)-1-(tert-butyldimethylsilyloxy)-4-(6-hydroxyindol-1-yl)-2-butyl]imidazole-4-carboxamide (80 mg, 0.187 mmol) in DMF (5 ml) was added potassium carbonate (38.7 mg, 0.280 mmol) at room temperature. The reaction mixture was stirred for 30 minutes. And then 1-iodobutane (51.5 mg, 0.280 mmol) was added and the resulting mixture was stirred for 24 hours at 60–80° C. The reaction mixture was poured into water (50 ml) and extracted with ethyl acetate. The organic layer was washed with brine, dried (sodium sulfate) and evaporated in vacuo. The residue was purified by silica gel (3 g) chromatography eluting with chloroform/methanol (50:1) to give 1-[(R)-4-(6-butoxyindol-1-yl)-1-(tert-butyldimethylsilyloxy)-2-butyl]imidazole-4-carboxamide (66.3 mg, 73.3%).

IR (KBr): 3600–3000, 2949, 2864, 1666, 1255, 840 cm$^{-1}$; NMR (CDCl$_3$, δ): −0.10 (3H, s), −0.08 (3H, s), 0.81 (9H, s), 1.00 (3H, t, J=7 Hz), 1.40–1.95 (4H, m), 2.20–2.60 (2H, m), 3.55–4.25 (7H, m), 5.39 (1H, brs), 6.43 (1H, d, J=3 Hz), 6.58 (1H, d, J=2 Hz), 6.78 (1H, d, J=3 Hz), 6.80 (1H, dd, J=9 Hz, 2 Hz), 6.97 (1H, brs), 7.38 (1H, s), 7.49 (1H, d, J=9 Hz), 7.68 (1H, s); MS: 485 (M+H)$^+$; $[α]_D^{27.8}$=+12.70° (C=0.50, EtOH).

PREPARATION 22

These compounds were prepared by a similar procedure to that of Preparation 21.

(1) 1-[(R)-1-(tert-Butyldimethylsilyloxy)-4-(6-hexyloxyindol-1-yl)-2-butyl]imidazole-4-carboxamide (72.9 mg, 76.1%)

IR (Neat): 3700–3000, 2935, 2862, 1666, 1254, 839 cm$^{-1}$; NMR (CDCl$_3$, δ): −0.10 (3H, s), −0.08 (3H, s), 0.81 (9H, s), 0.92 (3H, t, J=7 Hz), 1.20–1.95 (8H, m), 2.20–2.60 (2H, m), 3.55–4.25 (7H, m), 5.40 (1H, brs), 6.43 (1H, d, J=3 Hz), 6.59 (1H, d, J=2 Hz), 6.78 (1H, d, J=3 Hz), 6.80 (1H, dd, J=9 Hz, 2 Hz), 6.97 (1H, brs), 7.38 (1H, s), 7.49 (1H, d, J=9 Hz), 7.68 (1H, s); MS: 513 (M+H)$^+$; $[α]_D^{27.8}$=+10.40° (C=0.50, EtOH).

(2) 1-[(R)-1-(tert-Butyldimethylsilyloxy)-4-(5-(3-phenylpropoxy)indol-1-yl)-2-butyl]imidazole-4-carboxamide (88 mg, 76.6%)

IR (Neat): 3600–3000, 2935, 2860, 1662, 1240, 1126, 1093, 839 cm$^{-1}$; NMR (CDCl$_3$, δ): −0.10 (3H, s), −0.08 (3H, s), 0.81 (9H, s), 2.00–2.60 (4H, m), 2.85 (2H, t, J=8 Hz), 3.55–4.30 (7H, m), 5.41 (1H, brs), 6.41 (1H, d, J=3 Hz), 6.80–7.38 (5H, m), 7.40 (1H, s), 7.67 (1H, s); MS: 547 (M+H)$^+$; $[α]_D^{27.2}$=+16.30° (C=0.50, EtOH).

(3) 1-[(R)-1-(tert-Butyldimethylsilyloxy)-4-(5-hexyloxyindol-1-yl)-2-butyl]imidazole-4-carboxamide (57.9 mg, 53.8%)

IR (Neat): 3700–3000, 2933, 2862, 1662, 1473, 1240, 1126, 1095, 839 cm$^{-1}$; NMR (CDCl$_3$, δ): −0.10 (3H, s), −0.08 (3H, s), 0.81 (9H, s), 0.91 (3H, t, J=7 Hz), 1.25–1.90 (8H, m), 2.20–2.60 (2H, m), 3.60–4.30 (7H, m), 5.39 (1H, brs), 6.41 (1H, d, J=3 Hz), 6.80–7.15 (5H, m), 7.39 (1H, s), 7.67 (1H, s); MS: 513 (M+H)$^+$; $[α]_D^{27.9}$=+22.50° (C=0.50, EtOH).

(4) 1-[(R)-1-(tert-Butyldimethylsilyloxy)-4-(5-hexyloxy-1-methylindol-3-yl)-2-butyl]imidazole-4-carboxamide (54.8 mg, 51.2%)

IR (Neat): 3600–3000, 2935, 2860, 1668, 1556, 1489, 1252, 1122, 1086, 839 cm$^{-1}$; NMR (CDCl$_3$, δ): −0.08 (3H, s), −0.06 (3H, s), 0.82 (9H, s), 0.91 (3H, t, J=7 Hz), 1.25–1.65 (6H, m), 1.70–1.95 (2H, m), 2.05–2.35 (2H, m), 2.40–2.85 (2H, m), 3.60–3.85 (5H, m), 3.90–4.20 (3H, m), 5.35 (1H, brs), 6.70 (1H, s), 6.80–7.00 (3H, m), 7.18 (1H, d, J=9 Hz), 7.45 (1H, s), 7.66 (1H, s); MS: 527 (M+H)$^+$; $[α]_D^{26.8}$=+14.30° (C=0.50, EtOH).

PREPARATION 23

To a stirred mixture of 3-phenylpropanol (40 mg, 0.294 mmol) and methanesulfonyl chloride (40 mg, 0.353 mmol) in dichloromethane (5 ml) was added dropwise triethylamine (36 mg, 0.353 mmol) at ice-bath temperature. After 1 hour, the reaction mixture was partitioned between dichloromethane and water. The organic layer was washed with brine, dried (magnesium sulfate), and concentrated in vacuo to give the methanesulfonate (62.7 mg, 100%) as an oil. This material was used immediately without further purification.

Under N$_2$, to a solution of 1-[(R)-1-(tert-butyldimethylsilyloxy)-4-(6-hydroxyindol-1-yl)-2-butyl] imidazole-4-carboxamide (80 mg, 0.187 mmol) in DMF (4 ml) was added potassium carbonate (38.7 mg, 0.280 mmol) at room temperature. The reaction mixture was stirred for 20 minutes. And then the methanesulfonate prepared above in DMF (2 ml) was added and the resulting mixture was stirred for 48 hours at 80 to 90° C. The reaction mixture was poured into water (20 ml) and extracted with ethyl acetate. The extract was washed with brine, dried (sodium sulfate) and evaporated in vacuo. The residue was purified by silica gel (4 g) chromatography eluting with chloroform/methanol (100:1 to 10:1) to give 1-[(R)-1-(tert-butyldimethylsilyloxy)-4-(6-(3-phenylpropoxy)indol-1-yl)-2-butyl]imidazole-4-carboxamide (93.6 mg, 81.5%)

IR (Neat): 3600–3000, 2935, 2860, 1666, 1616, 1250, 1124, 1091, 839 cm$^{-1}$; NMR (CDCl$_3$, δ): −0.10 (3H, s), −0.08 (3H, s), 0.80 (9H, s), 2.00–2.60 (4H, m), 2.86 (2H, t, J=8 Hz), 3.60–4.20 (7H, m), 5.40 (1H, brs), 6.44 (1H, d, J=3 Hz), 6.56 (1H, d, J=2 Hz), 6.78 (1H, d, J=3 Hz), 6.80 (1H, dd, J=9 Hz, 2 Hz), 6.95 (1H, brs), 7.10–7.35 (5H, m), 7.38 (1H, s), 7.49 (1H, d, J=9 Hz), 7.67 (1H, s); MS: 547 (M+H)$^+$; $[α]_D^{27.8}$=+8.60° (C=0.50, EtOH).

PREPARATION 24

These compounds were prepared by a similar procedure to that of Preparation 23.

(1) 1-[(R)-1-(tert-Butyldimethylsilyloxy)-4-(6-(4-phenylbutoxy)indol-1-yl)-2-butyl]imidazole-4-carboxamide (92 mg, 78.1%)

IR (Neat): 3700–3000, 2935, 2860, 1668, 1614, 1464, 1250, 1124, 1091, 839 cm$^{-1}$; NMR (CDCl$_3$, δ): −0.10 (3H, s), −0.08 (3H, s), 0.80 (9H, s), 1.75–2.00 (4H, m), 2.20–2.80 (4H, m), 3.60–4.25 (7H, m), 5.32 (1H, brs), 6.43 (1H, d, J=3 Hz), 6.55 (1H, d, J=2 Hz), 6.70–6.85 (2H, m), 6.95 (1H, brs), 7.15–7.35 (6H, m), 7.37 (1H, s), 7.48 (1H, d, J=9 Hz), 7.80 (1H, s); MS: 561 (M+H)$^+$; $[α]_D^{27.3}$=+8.20° (C=0.50, EtOH).

(2) 1-{(R)-1-(tert-Butyldimethylsilyloxy)-4-[6-(3-(4-chlorophenyl)propoxy)indol-1-yl]-2-butyl}imidazole-4-carboxamide (90.5 mg, 83.4%)

IR (Neat): 3700–3000, 2941, 2862, 1668, 1616, 1469, 1254, 1093, 839 cm$^{-1}$; NMR (CDCl$_3$, δ): −0.10 (3H, s), −0.08 (3H, s), 0.81 (9H, s), 2.00–2.55 (4H, m), 2.83 (2H, t, J=8 Hz), 3.60–4.25 (7H, m), 5.38 (1H, brs), 6.44 (1H, d, J=3 Hz), 6.54 (1H, d, J=2 Hz), 6.75–6.90 (2H, m), 6.96 (1H, brs), 7.10–7.35 (5H, m), 7.38 (1H, s), 7.49 (1H, d, J=9 Hz), 7.67 (1H, s); MS: 581 (M+H)$^+$; $[α]_D^{28.2}$=+7.70° (C=0.50, EtOH).

(3) 1-{(R)-1-(tert-Butyldimethylsilyloxy)-4-[6-(3-(1-methylindol-3-yl)propoxy)indol-1-yl]-2-butyl}imidazole-4-carboxamide (78.6 mg, 70.2%)

IR (Neat): 3700–3000, 2937, 2860, 1668, 1617, 1469, 1250, 1091, 839 cm$^{-1}$; NMR (CDCl$_3$, δ): −0.11 (3H, s), −0.09 (3H, s), 0.80 (9H, s), 2.15–2.55 (4H, m), 2.99 (2H, t, J=7 Hz), 3.55–4.20 (10H, m), 5.30 (1H, brs), 6.44 (1H, d, J=3 Hz), 6.56 (1H, d, J=2 Hz), 6.75–7.00 (4H, m), 7.05–7.35 (3H, m), 7.36 (1H, s), 7.49 (1H, d, J=9 Hz), 7.62 (1H, d, J=8 Hz), 7.66 (1H, s); MS: 600 (M+H)$^+$; $[α]_D^{28.4}$=+8.40° (C=0.50, EtOH).

(4) 1-{(R)-1-(tert-Butyldimethylsilyloxy)-4-[6-(3-(1-methylindol-2-yl)propoxy)indol-1-yl]-2-butyl}imidazole-4-carboxamide (78.6 mg, 70.2%)

IR (KBr): 3600–3000, 2935, 2860, 1678, 1618, 1469, 1254, 1126, 1092, 839 cm$^{-1}$; NMR (CDCl$_3$, δ): −0.11 (3H, s), −0.09 (3H, s), 0.80 (9H, s), 1.95–2.50 (4H, m), 3.01 (2H, t, J=7 Hz), 3.55–4.20 (10H, m), 5.33 (1H, brs), 6.32 (1H, s), 6.44 (1H, d, J=3 Hz), 6.53 (1H, d, J=2 Hz), 6.79 (1H, d, J=3 Hz), 6.81 (1H, dd, J=9 Hz, 2 Hz), 7.03 (1H, brs), 7.00–7.35 (3H, m), 7.36 (1H, s), 7.45–7.60 (2H, m), 7.66 (1H, s); MS: 600 (M+H)$^+$.

(5) 1-[(R)-1-(tert-Butyldimethylsilyloxy)-4-(1-methyl-5-(3-phenylpropoxy)indol-3-yl)-2-butyl]imidazole-4-carboxamide (34.5 mg, 30.3%)

IR (Neat): 3700–3000, 2937, 2860, 1668, 1545, 1493, 1242, 1122, 1086, 839 cm$^{-1}$; NMR (CDCl$_3$, δ): −0.08 (3H, s), −0.06 (3H, s), 0.82 (9H, s), 2.00–2.30 (4H, m), 2.40–2.95 (4H, m), 3.60–3.85 (5H, m), 3.90–4.20 (3H, m), 5.35 (1H, brs), 6.71 (1H, s), 6.80–7.00 (3H, m), 7.10–7.40 (4H, m), 7.44 (1H, s), 7.66 (1H, s); MS: 561 (M+H)$^+$; $[\alpha]_D^{26.8}$=+12.30° (C=0.50, EtOH).

(6) 1-{(R)-1-(tert-Butyldimethylsilyloxy)-4-[5-(3-(4-chlorophenyl)propoxy)-1-methylindol-3-yl]-2-butyl}imidazole-4-carboxamide (418 mg, 62.2%)

IR (Neat): 3700–3000, 2951, 2860, 1668, 1599, 1238, 1090 cm$^{-1}$; NMR (CDCl$_3$, δ): −0.09 (3H, s), −0.06 (3H, s), 0.82 (9H, s), 2.00–2.30 (4H, m), 2.40–2.95 (4H, m), 3.60–3.85 (5H, m), 3.90–4.20 (3H, m), 5.35 (1H, brs), 6.72 (1H, s), 6.80–7.00 (3H, m), 7.10–7.35 (5H, m), 7.45 (1H, s), 7.66 (1H, s); MS: 595 (M+H)$^+$ ($^{35}$Cl), 597 (M+H)$^+$ ($^{37}$Cl); $[\alpha]_D^{22.6}$=+12.30° (C=0.50, EtOH).

PREPARATION 25

This compound was prepared by a similar procedure to that of Preparation 18.

1-[2-((4S)-2,2-Dimethyl-1,3-dioxolan-4-yl)ethyl]-1H-5-benzyloxyindole (2.34 g, 98.8%).

IR (Neat): 2983, 2935, 2873, 1487, 1236, 1149, 1053 cm$^{-1}$; NMR (CDCl$_3$, δ): 1.34 (3H, s), 1.45 (3H, s), 1.85–2.20 (2H, m), 3.35–4.40 (5H, m), 5.10 (2H, s), 6.40 (1H, d, J=3 Hz), 6.95 (1H, dd, J=9 Hz, 2 Hz), 7.09 (1H, d, J=3 Hz), 7.17 (1H, d, J=2 Hz), 7.25–7.55 (6H, m); MS: 352 (M+H)$^+$.

PREPARATION 26

This compound was prepared by a similar procedure to that of Preparation 20.

1-[(R)-1-(tert-Butyldimethylsilyloxy)-4-(5-hydroxyindol-1-yl)-2-butyl]imidazole-4-carboxamide (348 mg, 82.6%)

IR (KBr): 3600–3000, 2935, 2858, 1666, 1593, 1246, 1128, 840 cm$^{-1}$; NMR (CDCl$_3$, δ): −0.10 (3H, s), −0.08 (3H, s), 0.81 (9H, s), 2.20–2.55 (2H, m), 3.55–4.25 (5H, m), 5.37 (1H, brs), 5.42 (1H, brs), 6.38 (1H, d, J=3 Hz), 6.80 (1H, dd, J=9 Hz, 2 Hz), 6.86 (1H, d, J=3 Hz), 6.90–7.10 (3H, m), 7.38 (1H, s), 7.66 (1H, s); MS: 429 (M+H)$^+$.

PREPARATION 27

To a solution of ethyl 3-(1-methylindol-2-yl)acryrate (3.0 g, 13.1 mmol) in THF (60 ml) 10% palladium on carbon (600 mg) was added and the mixture was stirred under hydrogen (2 atm) for 2.5 hours at room temperature. The mixture was filtered through Celite and washed with THF. The filtrate was concentrated in vacuo to give ethyl 3-(1-methylindol-2-yl)propionate (3.12 g, 103%) as a yellow solid.

IR (KBr): 2981, 2925, 2858, 1728, 1184 cm$^{-1}$; NMR (CDCl$_3$, δ): 1.27 (3H, t, J=7 Hz), 2.65–2.85 (2H, m), 3.00–3.15 (2H, m), 3.69 (3H, s), 4.17 (2H, q, J=7 Hz), 6.25 (1H, s), 7.00–7.35 (3H, m), 7.53 (1H, d, J=7 Hz); MS: 232 (M+H)$^+$.

PREPARATION 28

To an ice-cooled solution of ethyl 3-(1-methylindol-2-yl)propionate (2.0 g, 8.65 mmol) in tetrahydrofuran (20 ml) was added lithium aluminum hydride (328 mg, 8.65 mmol) by small portions under nitrogen atmosphere. After the mixture was stirred for 1 hour, water and aqueous 15% sodium hydroxide solution were added successively to the mixture. The resulting precipitates were filtrated off through Celite and washed with tetrahydrofuran. The filtrate was dried over magnesium sulfate and concentrated under reduced pressure. The residue was purified by silica gel (36 g) chromatography eluting with dichloromethane-methanol (100:1 to 50:1) to give 3-(1-methylindol-2-yl)propan-1-ol (1.05 g, 64.1%) as a yellow syrup.

IR (KBr): 3286, 2935, 2877, 1547; 1468, 1234, 1055 cm$^{-1}$; NMR (CDCl$_3$, δ): 1.37 (1H, br), 2.01 (2H, m), 2.87 (2H, t, J=8 Hz), 3.69 (3H, s), 3.78 (2H, t, J=6 Hz), 6.28 (1H, s), 7.00–7.35 (3H, m), 7.53 (1H, d, J=7 Hz); MS: 190 (M+H)$^+$.

PREPARATION 29

Methyltriphenylphosphonium bromide (2.06 g, 5.77 mmol) was dried in vacuo for 2 hours then suspended with stirring in tetrahydrofuran (15 ml) under nitrogen. The mixture was cooled to −78° C. and n-butyllithium in tetrahydrofuran (3.75 ml, 5.77 mmol) was added dropwise. After stirring for 2 hours being allowed to warm to room temperature, the mixture was again cooled to −78° C. and 3-(1-methylindol-3-yl)propionaldehyde (90° mg, 4.81 mmol) in tetrahydrofuran (6 ml) was added dropwise. After 2 hours stirring at room temperature, the reaction was quenched by addition of aqueous ammonium chloride. This mixture was extracted with ethyl acetate, and the extracts were washed with brine, dried (magnesium sulfate) and evaporated in vacuo. The residue was purified by silica gel (36 g) chromatography eluting with hexane/ethyl acetate (20:1) to give 3-(3-butenyl)-1-methylindole (539 mg, 60.5%) as a colorless oil.

IR (Neat): 2962, 2924, 1697, 1543, 1522, 1238, 1088 cm$^{-1}$; NMR (CDCl$_3$, δ): 2.46 (2H, m), 2.85 (2H, t, J=8 Hz), 3.74 (3H, s), 4.90–5.20 (2H, m), 5.80–6.05 (1H, m), 6.84 (1H, s), 7.00–7.35 (3H, m), 7.60 (1H, d, J=8 Hz).

PREPARATION 30

To a mixture of tert-butyl alcohol (14 ml) and water (14 ml) was added AD-mix-a (4.0 g). The mixture was stirred at room temperature until both phases are clear, and then cooled to 0° C. 3-(3-butenyl)-1-methylindole (530 mg, 2.86 mmol) was added, and the heterogeneous slurry was stirred vigorously at 0° C. for 4 hours. While the mixture was stirred at 0° C., solid sodium sulfite (4.29 g) was added and the mixture was allowed to warm to room temperature and stirred for 1 hour. This mixture was extracted with ethyl acetate, and the extracts were washed with brine, dried (magnesium sulfate) and evaporated in vacuo. The residue was purified by silica gel (15 g) chromatography eluting with chloroform/methanol (100:1 to 20:1) to give (S)-4-(1-methylindol-3-yl)butane-1,2-diol (602 mg, 96.1%).

IR (Neat): 3700–2800, 1697, 1649, 1542, 1522, 1238, 1088 cm$^{-1}$; NMR (CDCl$_3$, δ): 1.75–2.00 (3H, m), 2.08 (1H, brs), 2.75–3.05 (2H, m), 3.35–3.90 (6H, m), 6.87 (1H, s), 7.00–7.35 (3H, m), 7.60 (1H, d, J=8 Hz); MS: 242 (M+Na)$^+$.

PREPARATION 31

To an ice cooled solution of (S)-4-(1-methylindol-3-yl)butane-1,2-diol (600 mg, 2.74 mmol) in DMF (10 ml) was added imidazole (559 mg, 8.21 mmol) followed by tert-butyldimethylsilyl chloride (433 mg, 2.87 mmol). After 30 minutes the ice-bath was removed and then the mixture was stirred overnight at room temperature.

The reaction mixture was poured into water (100 ml) and extracted with ethyl acetate. The organic layer was washed with brine, dried (magnesium sulfate), and concentrated in vacuo. The residue was purified by silica gel (15 g) column chromatography eluting with hexane/ethyl acetate (10:1) to give (S)-1-(tert-butyldimethylsilyloxy)-4-(1-methylindol-3-yl)butan-2-ol (633 g, 69.3%) as a colorless oil.

IR (Neat): 3700–3100, 3053, 2927, 2858, 1545, 1462, 1240, 1090 cm$^{-1}$; NMR (CDCl$_3$, δ): −0.06 (6H, s), 0.84 (9H, s), 1.65–1.85 (2H, m), 2.39 (1H, d, J=3 Hz), 2.65–3.00 (2H, m), 3.30–3.75 (6H, m), 6.79 (1H, s), 6.95–7.30 (3H, m), 7.54 (1H, d, J=8 Hz); MS: 334 (M+H)$^+$.

PREPARATION 32

To an ice cooled solution of 5-benzyloxy-1-methylindole-3-carboxaldehyde (13.0 9, 49.0 mmol) and triethyl phosphonoacetate (13.2 g, 58.8 mmol) in DMF (100 ml) was added sodium hydride (60% in mineral oil, 2.74 g, 68.6 mmol). The mixture was stirred overnight at room temperature. The reaction mixture was poured into ice-water (700 ml) and stirred 30 minutes. The resulting precipitates were collected by filtration, washed with water and dried in vacuo to give ethyl 3-(5-benzyloxy-1-methylindol-3-yl)acrylate (14.2 g, 86.3t) as a pale yellow solid.

IR (Neat): 2991, 2947, 2902, 1703, 1618, 1380, 1280, 1228, 1176, 1066, 1003 cm$^{-1}$; NMR (CDCl$_3$, δ): 1.36 (3H, t, J=7 Hz), 3.78 (3H, s), 4.27 (2H, q, J=7 Hz), 5.15 (2H, s), 6.30 (1H, d, J=16 Hz), 7.03 (1H, dd, J=9 Hz, 2 Hz), 7.15–7.60 (8H, m), 7.86 (1H, d, J=16 Hz); MS: 336 (M+H)$^+$.

PREPARATION 33

This compound was prepared by a similar procedure to that of Preparation 27. In this case ethanol and tetrahydrofuran were used as solvent.
Ethyl 3-(5-Benzyloxy-1-methylindol-3-yl)propionate (10.6 g, 90.0%)

IR (Neat): 3438, 2962, 2924, 1730, 1618, 1236, 1086 cm$^{-1}$; NMR (CDCl$_3$, δ): 1.25 (3H, t, J=7 Hz), 2.66 (2H, t, J=8 Hz), 3.04 (2H, t, J=8 Hz), 3.71 (3H, s), 4.14 (2H, q, J=7 Hz), 5.11 (2H, s), 6.84 (1H, s), 6.96 (1H, dd, J=9 Hz, 2 Hz), 7.12 (1H, d, J=2 Hz), 7.18 (2H, d, J=9 Hz), 7.30–7.55 (5H, m); MS: 338 (M+H)$^+$.

PREPARATION 34

Under nitrogen, to a stirred solution of ethyl 3-(5-benzyloxy-1-methylindol-3-yl)propionate (12.0 g, 35.6 mmol) in dichloromethane (120 ml) was added dropwise 1.0 M DIBAL in hexane (37.4 ml, 35.6 mmol) at −78° C. (dry-ice/acetone) for 25 minutes. After 30 minutes, methanol (5.7 ml) was added dropwise at −78° C. and then the mixture was stirred at room temperature for 30 minutes. The mixture was filtered through Celite and washed with dichloromethane. The filtrate was concentrated in vacuo and then the residue was purified by silica gel (90 g) chromatography eluted with toluene/ethyl acetate (10:1 to 5:1) to give 3-(5-benzyloxy-1-methylindol-3-yl)propionaldehyde (8.03 g, 77.0%)

IR (KBr): 2924, 1712, 1491, 1223, 1063, 1016 cm$^{-1}$; NMR (CDCl$_3$, δ): 2.80 (2H, t, J=7 Hz), 3.05 (2H, t, J=7 Hz), 3.71 (3H, s), 5.12 (2H, s), 6.82 (1H, s), 6.97 (1H, dd, J=9 Hz, 2 Hz), 7.09 (1H, d, J=2 Hz), 7.15–7.55 (6H, m), 9.83 (1H, s); MS: 294 (M+H)$^+$.

PREPARATION 35

This compound was prepared by a similar procedure to that of Preparation 29.
5-Benzyloxy-3-(3-butenyl)-1-methylindole (6.92 g, 87.7%)

IR (Neat): 2918, 2850, 1626, 1489, 1223, 1055, 1026, 914 cm$^{-1}$; NMR (CDCl$_3$, δ): 2.43 (2H, q, J=7 Hz), 2.79 (2H, t, J=7 Hz), 3.71 (3H, s), 4.90–5.20 (4H, m), 5.80–6.05 (1H, m), 6.82 (1H, s), 6.95 (1H, dd, J=9 Hz, 2 Hz), 7.12 (1H, d, J=2 Hz), 7.18 (1H, d, J=9 Hz), 7.30–7.55 (5H, m); MS: 292 (M+H)$^+$.

PREPARATION 36

This compound was prepared by a similar procedure to that of Preparation 30.
(S)-4-(5-benzyloxy-1-methylindol-3-yl)butane-1,2-diol (4.30 g, 53.5%)

IR (KBr): 3365, 2933, 2887, 1491, 1227, 1093, 1055, 1038 cm$^{-1}$; NMR (CDCl$_3$, δ): 1.65–1.95 (3H, m), 2.03 (1H, d, J=4 Hz), 2.70–3.00 (2H, m), 3.35–3.90 (6H, m), 5.12 (2H, s), 6.83 (1H, s), 6.96 (1H, dd, J=9 Hz, 2 Hz), 7.11 (1H, d, J=2 Hz), 7.18 (1H, d, J=9 Hz), 7.30–7.55 (5H, m); MS: 326 (M+H)$^+$; $[\alpha]_D^{23.5}$=−21.6° (C=0.50, EtOH).

PREPARATION 37

This compound was prepared by a similar procedure to that of Preparation 31.
(S)-4-(5-Benzyloxy-1-methylindol-3-yl)-1-(tert-butyldimethylsilyloxy)butan-2-ol (4.85 g, 84.5%)

IR (Neat): 3458, 2931, 2858, 1489, 1252, 1116, 1076, 839 cm$^{-1}$ NMR (CDCl$_3$, δ): 0.07 (6H, s), 0.90 (9H, s), 1.65–1.90 (2H, m), 2.44 (1H, d, J=4 Hz), 2.65–3.05 (2H, m), 3.30–3.85 (6H, m), 5.11 (2H, s), 6.83 (1H, s), 6.95 (1H, dd, J=9 Hz, 2 Hz), 7.13 (1H, d, J=2 Hz), 7.18 (1H, d, J=9 Hz), 7.30–7.55 (5H, m); MS: 440 (M+H)$^+$; $[\alpha]_D^{23.2}$=−25.50° (C=0.50, EtOH).

PREPARATION 38

This compound was prepared by a similar procedure to that of Preparation 20.
1-[(R)-1-(tert-Butyldimethylsilyloxy)-4-(5-hydroxy-1-methylindol-3-yl)-2-butyl]imidazole-4-carboxamide (281 mg, 95.8%)

IR (KBr): 3600–3000, 2935, 1658, 1591, 1483, 1255, 1124, 841 cm$^{-1}$; NMR (CDCl$_3$, δ): −0.09 (3H, s), −0.06 (3H, s), 0.82 (9H, s), 2.00–2.75 (4H, m), 3.55–4.15 (6H, m), 5.49 (1H, brs), 6.07 (1H, brs), 6.72 (1H, s), 6.80–6.90 (2H, m), 7.03 (1H, brs), 7.14 (1H, d, J=9 Hz), 7.49 (1H, s), 7.72 (1H, s); MS: 443 (M+H)$^+$; $[\alpha]_D^{24.1}$=+23.10° (C=0.50, EtOH).

PREPARATION 39

This compound was prepared by a similar procedure to that of Preparation 28. In this case diethylether was used as solvent instead of tetrahydrofuran.
(3S,4S)-4-Benzyloxy-3-(tert-butyldimethylsilyloxy)pentan-1-ol (3.43 g, 81.1%)

IR (Neat): 3700–3100, 2956, 2860, 1462, 1248, 1090 cm$^{-1}$; NMR (CDCl$_3$, δ): −0.01 (3H, s), 0.09 (3H, s), 0.86 (9H, s), 1.17 (3H, d, J=6 Hz), 1.50–2.05 (2H, m), 2.44 (1H, t, J=6 Hz), 3.45–4.00 (4H, m), 4.50 (1H, d, J=12 Hz), 4.63 (1H, d, J=12 Hz), 7.20–7.45 (5H, m); MS: 325 (M+H)$^+$.

PREPARATION 40

This compound was prepared by a similar procedure to that of Preparation 31.
(3S,4S)-4-Benzyloxy-1-(tert-butyldimethylsilyloxy)pentan-3-ol (8.04 g, 73.9%)

IR (Neat): 3600–3000, 2958, 2929, 2860, 1238, 1087 cm$^{-1}$; NMR (CDCl$_3$, δ): 0.06 (6H, s), 0.89 (9H, s), 1.20 (3H, d, J=6 Hz), 1.69 (2H, m), 3.06 (1H, d, J=3 Hz), 3.35–3.95 (4H, m), 4.47 (1H, d, J=12 Hz), 4.66 (1H, d, J=12 Hz), 7.20–7.40 (5H, m); MS: 325 (M+H)$^+$.

PREPARATION 41

To a stirred mixture of 1-[(2S,3R)-2-benzyloxy-5-hydroxy-3-pentyl]imidazole-4-carboxamide (330 mg, 1.09 mmol) and methanesulfonyl chloride (249 mg, 2.18 mmol) in dichloromethane (10 ml) was added dropwise triethylamine (220 mg, 2.18 mmol) at ice-bath temperature. After 1 hour, the reaction mixture was partitioned between dichloromethane and water. The organic layer was washed with brine, dried (magnesium sulfate), and concentrated in vacuo to give 1-[(2S,3R)-2-benzyloxy-5-methanesulfonyloxy-3-pentyl]imidazole-4-carboxamide (430 mg, 103%) as an oil. This material was used for the next reaction without further purification.

IR (Neat): 3344, 3149, 2972, 2935, 2873, 1664, 1597, 1346, 1234, 1171, 1097, 1041 cm$^{-1}$.

PREPARATION 42

To a stirred solution of 2-oxobenzothiazole (83 mg, 0.549 mmol) in DMF (3 ml) was added NaH (60% in mineral oil, 22 mg, 0.549 mmol) at room temperature. After 10 minutes, 1-[(2S,3R)-2-benzyloxy-5-methanesulfonyloxy-3-pentyl]imidazole-4-carboxamide in DMF (3 ml) was added and the resulting mixture was stirred for 6 hours at 60 to 70° C. The reaction mixture was poured into water (30 ml) and extracted with ethyl acetate. The organic layer was washed with brine, dried (sodium sulfate), and concentrated in vacuo. The residue was purified by silica gel (8 g) column chromatography eluting with chloroform/methanol (100:1 to 30:1) to give 1-[(2S,3R)-2-benzyloxy-5-(2-oxobenzothiazol-3-yl)-3-pentyl]imidazole-4-carboxamide (63 mg, 52.7%).

IR (KBr): 3600–3000, 2970, 1666, 1593, 1238, 1093 cm$^{-1}$; NMR (CDCl$_3$, δ): 1.04 (3H, d, J=6 Hz), 2.05–2.60 (2H, m), 3.55–4.20 (4H, m), 4.36 (1H, d, J=12 Hz), 4.57 (1H, d, J=12 Hz), 5.38 (1H, brs), 6.78 (1H, d, J=7 Hz), 6.96 (1H, brs), 7.10–7.50 (8H, m), 7.54 (1H, s), 7.67 (1H, s); MS: 437 (M+H)$^+$.

PREPARATION 43

These compounds were prepared by a similar procedure to that of Preparation 42.
(1) 1-[(2S,3R)-2-Benzyloxy-5-(indazol-1-yl)-3-pentyl]imidazole-4-carboxamide (57 mg, 47.6%)

IR (KBr): 3600–3000, 2976, 2935, 2871, 1662, 1599, 1259, 1095 cm$^{-1}$; NMR (CDCl$_3$, δ): 1.04 (3H, d, J=6 Hz), 2.20–2.90 (2H, m), 3.55–4.45 (5H, m), 4.54 (1H, d, J=12 Hz), 5.40 (1H, brs), 6.97 (1H, brs), 7.05–7.50 (10H, m), 7.67 (1H, s), 7.73 (1H, d, J=8 Hz); MS: 404 (M+H)$^+$; [α]$_D^{24.2}$=+44.00° (C=0.50, EtOH).
(2) 1-[(2S,3R)-2-Benzyloxy-5-(2-oxindol-1-yl)-3-pentyl]imidazole-4-carboxamide (63 mg, 52.7%)

NMR (CDCl$_3$, δ): 1.06 (3H, d, J=6 Hz), 2.05–2.65 (2H, m), 3.40–4.70 (8H, m), 5.37 (1H, brs), 6.61 (1H, d, J=7 Hz), 6.85–7.10 (2H, m), 7.15–7.60 (8H, m), 7.64 (1H, s); MS: 419 (M+H)$^+$.

PREPARATION 44

This compound was prepared by a similar procedure to that of Preparation 18.
1-[2-((4S)-2,2-Dimethyl-1,3-dioxolan-4-yl)ethyl]-1H-2-methylindole (1.52 g, 88.2%)

IR (Neat): 3051, 2983, 2931, 2875, 1236, 1159, 1085, 1055 cm$^{-1}$; NMR (CDCl$_3$, δ): 1.36 (3H, s), 1.47 (3H, s), 1.75–2.15 (2H, m), 2.45 (3H, s), 3.47 (1H, t, J=7 Hz), 3.90–4.35 (3H, m), 6.24 (1H, s), 7.00–7.25 (2H, m), 7.31 (1H, d, J=8 Hz), 7.52 (1H, d, J=7 Hz); MS: 260 (M+H)$^+$.

PREPARATION 45

A mixture of ethyl 1-[(2S,3R)-2-(benzyloxy)-5-(2,3-dichlorophenyl)-3-pentyl]-1,2,4-triazole-3-carboxylate (103 mg) and iodotrimethylsilane (0.08 ml) in chloroform (4 ml) was stirred at room temperature for 2 hours. The mixture was poured into cold methanol and the whole was evaporated in vacuo. The residue was taken up in ethyl acetate, washed with water, aqueous sodium bisulfite and sodium bicarbonate, successively, and dried. The residue left after evaporation of solvent was purified by column chromatography on silica gel, eluting with a mixture of dichloromethane and methanol (50:1) to give a gummy oil of ethyl 1-[(2S,3R)-2-hydroxy-5-(2,3-dichlorophenyl)-3-pentyl]-1,2,4-triazole-3-carboxylate (32 mg).

NMR (CDCl$_3$, δ): 1.16 (3H, d, J=6 Hz), 1.45 (3H, t, J=7 Hz), 2.22 (1H, d, J=4 Hz), 2.3–2.8 (4H, m), 4.1–4.4 (2H, m), 4.50 (2H, q, J=7 Hz), 6.9–7.4 (3H, m), 8.25 (1H, s); MS: 372 (M+H)$^+$.

PREPARATION 46

The following compound was prepared according to a similar manner to Preparation 45.
Ethyl 1-[(2S,3R)-2-Hydroxy-5-(2,3-dichlorophenyl)-3-pentyl]-1,2,4-triazole-5-carboxylate NMR (CDCl$_3$, δ): 1.19 (3H, d, J=6 Hz), 1.46 (3H, t, J=7 Hz), 2.2–2.8 (4H, m), 2.85 (1H, d, J=3 Hz), 4.0–4.2 (1H, m), 4.47 (2H, q, J=7 Hz), 5.3–5.5 (1H, m), 6.9–7.4 (3H, m), 8.06 (1H, s); MS: 372 (M+H)$^+$.

EXAMPLE 12

These compounds were prepared by a similar procedure to that of Example 2.
(1) 1-{(R)-1-Hydroxy-4-[6-(3-(3-pyridyl)propionylamino)indol-1-yl]-2-butyl}imidazole-4-carboxamide (73.4 mg, 97.2%)

IR (KBr): 3600–2800, 1664, 1593, 1261 cm$^{-1}$; NMR (DMSO-d$_6$, δ): 2.20–2.40 (2H, m), 2.67 (2H, t, J=8 Hz), 2.95 (2H, t, J=8 Hz), 3.50–4.25 (5H, m), 5.09 (1H, brs), 6.36 (1H, d, J=3 Hz), 7.00–7.16 (2H, m), 7.18 (1H, d, J=3 Hz), 7.20–7.40 (2H, m), 7.43 (1H, d, J=9 Hz), 7.65–7.90 (4H, m), 8.30–8.55 (2H, m), 9.87 (1H, brs); MS: 447 (M+H)$^+$.
(2) 1-[(R)-1-Hydroxy-4-(6-(6-phenylhexanoylamino)indol-1-yl)-2-butyl]imidazole-4-carboxamide (47 mg, 86.6%)

IR (KBr): 3700–3000, 2929, 2856, 1657, 1591, 1490, 1261 cm$^{-1}$; NMR (DMSO-d$_6$, δ): 1.20–1.75 (6H, m), 2.20–2.70 (6H, m), 3.50–4.20 (5H, m), 5.06 (1H, brs), 6.36 (1H, d, J=3 Hz), 7.00–7.35 (9H, m), 7.43 (1H, d, J=9 Hz), 7.70–7.90 (3H, m), 9.80 (1H, brs); MS: 488 (M+H)$^+$.
(3) 1-[(R)-4-(6-Acetylaminoindol-1-yl)-1-hydroxy-2-butyl]imidazole-4-carboxamide (41 mg, 86.9%)

IR (KBr): 3600–3000, 2962, 2926, 1662, 1593, 1267 cm$^{-1}$; NMR (DMSO-d$_6$, δ): 2.05 (3H, s), 2.20–2.40 (2H, m), 3.50–4.20 (5H, m), 5.11 (1H, brs), 6.36 (1H, d, J=3 Hz), 7.00–7.15 (2H, m), 7.17 (1H, d, J=3 Hz), 7.30 (1H, brs) 7.43 (1H, d, J=9 Hz), 7.70–7.85 (3H, m), 9.89 (1H, brs); MS: 356 (M+H)$^+$.
(4) 1-{(R)-4-[6-((2-Benzothiazolylthio)acetylamino)indol-1-yl]-1-hydroxy-2-butyl}imidazole-4-carboxamide (74.5 mg, 82.7%)

IR (KBr): 3700–2800, 1658, 1593, 1236 cm$^{-1}$; NMR (DMSO-d$_6$, δ): 2.15–2.20 (2H, m), 3.50–4.25 (5H, m), 4.42

(1H, s), 5.05 (1H, t, J=5 Hz), 6.38 (1H, d, J=3 Hz), 6.90–8.10 (12H, m), 10.39 (1H, s); MS: 521 (M+H)$^+$.

(5) 1-[(R)-4-(6-(3-Benzylureido)indol-1-yl)-1-hydroxy-2-butyl]imidazole-4-carboxamide (75 mg, 98.2%)

IR (KBr): 3600–2800, 1654, 1593, 1240 cm$^{-1}$; NMR (DMSO-d$_6$, δ): 2.15–2.40 (2H, m), 3.59 (2H, t, J=5 Hz), 3.85–4.20 (3H, m), 4.32 (2H, d, J=6 Hz), 5.05 (1H, t, J=5 Hz), 6.32 (1H, d, J=3 Hz), 6.56 (1H, t, J=6 Hz), 6.90 (1H, dd, J=8 Hz, 2 Hz), 6.95–7.45 (9H, m), 7.62 (1H, d, J=2 Hz), 7.73 (1H, s), 7.79 (1H, s), 8.46 (1H, s); MS: 447 (M+H)$^+$.

(6) 1-[(R)-1-Hydroxy-4-(6-(3-phenethylureido)indol-1-yl)-2-butyl]imidazole-4-carboxamide (60 mg, 89.2%)

IR (KBr): 3600–3000, 2937, 1657, 1591, 1556, 1242, 1086 cm$^{-1}$; NMR (DMSO-d$_6$, δ): 2.20–2.40 (2H, m), 2.76 (2H, t, J=7 Hz), 3.10–3.45 (2H, m), 3.60 (2H, t, J=5 Hz), 3.85–4.20 (3H, m), 5.06 (1H, t, J=5 Hz), 6.07 (1H, t, J=6 Hz), 6.32 (1H, d, J=3 Hz), 6.75–7.45 (10H, m), 7.61 (1H, s), 7.74 (1H, s), 7.79 (1H, s), 8.40 (1H, s); MS: 461 (M+H)$^+$.

(7) 1-[(R)-1-Hydroxy-4-(6-(3-phenylpropylamino)indol-1-yl)-2-butyl]imidazole-4-carboxamide (12.7 mg, 30.5%)

IR (KBr): 3600–3000, 2933, 2858, 1664, 1618, 1577, 1236, 1080 cm$^{-1}$; NMR (CDCl$_3$, δ): 1.80–2.10 (4H, m), 2.15–2.55 (2H, m), 2.77 (2H, t, J=8 Hz), 3.17 (2H, t, J=8 Hz), 3.60–4.20 (5H, m), 5.40 (1H, brs), 6.20 (1H, d, J=2 Hz), 6.36 (1H, d, J=3 Hz), 6.49 (1H, dd, J=9 Hz, 2 Hz), 6.68 (1H, d, J=3 Hz), 6.97 (1H, brs), 7.05–7.50 (8H, m), 7.71 (1H, s); MS: 432 (M+H)$^+$.

(8) 1-[(R)-1-Hydroxy-4-(3-methyl-6-(4-phenylbutyrylamino)indol-1-yl)-2-butyl]imidazole-4-carboxamide (38.1 mg, 77.0%)

IR (KBr): 3600–3000, 2927, 2866, 1657, 1592, 1257 cm$^{-1}$; NMR (DMSO-d$_6$, δ): 1.80–2.05 (2H, m), 2.15–2.40 (4H, m), 2.64 (2H, t, J=8 Hz), 3.59 (2H, t, J=5 Hz), 3.80–4.20 (3H, m), 5.05 (1H, t, J=5 Hz), 6.93 (1H, s), 7.00–7.45 (9H, m), 7.65–7.85 (3H, m), 9.80 (1H, s); MS: 474 (M+H)$^+$.

(9) 1-{(R)-1-Hydroxy-4-[3-methyl-6-(3-(1-methylbenzimidazol-2-yl)propionylamino)indol-1-yl]-2-butyl}imidazole-4-carboxamide (68.5 mg, 76.8%)

IR (KBr): 3700–2800, 1664, 1595 cm$^{-1}$; NMR (DMSO-d$_6$, δ): 2.10–2.35 (5H, m), 2.96 (2H, t, J=7 Hz), 3.19 (2H, t, J=7 Hz), 3.58 (2H, brs), 3.70–4.20 (6H, m), 5.04 (1H, brs), 6.93 (1H, s), 7.00–7.63 (8H, m), 7.65–7.85 (3H, m), 10.02 (1H, s); MS: 514 (M+H)$^+$.

(10) 1-[(R)-4-(6-Butoxyindol-1-yl)-1-hydroxy-2-butyl]imidazole-4-carboxamide (40.8 mg, 92.6%)

IR (KBr): 3317, 3236, 3163, 2954, 1676, 1581, 1238, 1088 cm$^{-1}$; NMR (DMSO-d$_6$, δ): 0.95 (3H, t, J=7 Hz), 1.35–1.85 (4H, m), 2.10–2.40 (2H, m), 3.50–4.20 (7H, m), 5.05 (1H, brs), 6.33 (1H, d, J=3 Hz), 6.65 (1H, dd, J=9 Hz, 2 Hz), 6.73 (1H, d, J=2 Hz), 7.07 (1H, brs), 7.11 (1H, d, J=3 Hz), 7.27 (1H, brs), 7.38 (1H, d, J=9 Hz), 7.70 (1H, s), 7.80 (1H, s); MS: 371 (M+H)$^+$.

(11) 1-[(R)-4-(6-Hexyloxyindol-1-yl)-1-hydroxy-2-butyl]imidazole-4-carboxamide (39.3 mg, 78.5%)

IR (KBr): 3500–3000, 2931, 2862, 1662, 1614, 1252, 1080 cm$^{-1}$; NMR (DMSO-d$_6$, δ): 0.89 (3H, t, J=7 Hz), 1.15–1.55 (6H, m), 1.60–1.85 (2H, m), 2.10–2.40 (2H, m), 3.50–4.20 (7H, m), 5.04 (1H, brs), 6.33 (1H, d, J=3 Hz), 6.64 (1H, dd, J=9 Hz, 2 Hz), 6.74 (1H, d, J=2 Hz), 7.06 (1H, brs), 7.11 (1H, d, J=3 Hz), 7.26 (1H, brs), 7.38 (1H, d, J=9 Hz), 7.70 (1H, s), 7.80 (1H, s); MS: 399 (M+H)$^+$; [α]$_D^{27.6}$=+18.90° (C=0.50, EtOH).

(12) 1-[(R)-1-Hydroxy-4-(6-(3-phenylpropoxy)indol-1-yl)-2-butyl]imidazole-4-carboxamide (55.6 mg, 78.1%)

IR (KBr): 3319, 3186, 2935, 2860, 1680, 1612, 1238, 1084 cm$^{-1}$; NMR (DMSO-d$_6$, δ): 1.90–2.40 (4H, m), 2.78 (2H, t, J=8 Hz), 3.60 (2H, t, J=5 Hz), 3.80–4.20 (5H, m), 5.04 (1H, t, J=5 Hz), 6.34 (1H, d, J=3 Hz), 6.68 (1H, dd, J=9 Hz, 2 Hz), 6.73 (1H, d, J=2 Hz), 7.00–7.45 (9H, m), 7.70 (1H, s), 7.80 (1H, s); MS: 433 (M+H)$^+$.

(13) 1-[(R)-1-Hydroxy-4-(6-(4-phenylbutoxy)indol-1-yl)-2-butyl]imidazole-4-carboxamide (72.7 mg, 100%)

IR (KBr): 3357, 3182, 2937, 2866, 1664, 1612, 1464, 1252, 1084 cm$^{-1}$; NMR (DMSO-d$_6$, δ): 1.75–1.90 (4H, m), 2.10–2.40 (2H, m), 2.55–2.75 (2H, br), 3.60 (2H, t, J=5 Hz), 3.80–4.20 (5H, m), 5.04 (1H, t, J=5 Hz), 6.33 (1H, d, J=3 Hz), 6.64 (1H, dd, J=9 Hz, 2 Hz), 6.73 (1H, d, J=2 Hz), 7.00–7.45 (9H, m), 7.70 (1H, s), 7.80 (1H, s); MS: 447 (M+H)$^+$.

(14) 1-{(R)-4-[6-(3-(4-Chlorophenyl)propoxy)indol-1-yl]-1-hydroxy-2-butyl}imidazole-4-carboxamide (61.6 mg, 93.6%)

IR (KBr): 3600–3000, 2935, 2871, 1658, 1618, 1491, 1250, 1088 cm$^{-1}$; NMR (DMSO-d$_6$, δ): 1.90–2.40 (4H, m), 2.77 (2H, t, J=8 Hz), 3.50–4.20 (7H, m), 5.05 (1H, brs), 6.34 (1H, d, J=3 Hz), 6.67 (1H, dd, J=9 Hz, 2 Hz), 6.70 (1H, d, J=2 Hz), 7.08 (1H, brs), 7.12 (1H, d, J=3 Hz), 7.15–7.45 (6H, m), 7.70 (1H, s), 7.80 (1H, s); MS: 467 (M+H)$^+$.

(15) 1-{(R)-1-Hydroxy-4-[6-(3-(1-methylindol-3-yl)propoxy)indol-1-yl]-2-butyl}imidazole-4-carboxamide (47.3 mg, 83.5%)

IR (KBr): 3600–3000, 2933, 2875, 1658, 1618, 1469, 1246, 1084 cm$^{-1}$; NMR (DMSO-d$_6$, δ): 2.00–2.40 (4H, m), 2.87 (2H, t, J=7 Hz), 3.50–4.20 (10H, m), 5.05 (1H, brs), 6.34 (1H, d, J=3 Hz), 6.69 (1H, dd, J=9 Hz, 2 Hz), 6.76 (1H, d, J=2 Hz), 6.90–7.20 (5H, m), 7.28 (1H, brs), 7.30–7.45 (2H, m), 7.55 (1H, d, J=8 Hz), 7.70 (1H, s), 7.80 (1H, s); MS: 486 (M+H)$^+$; [α]$_D^{28.0}$=+17.20° (C=0.50, EtOH).

(16) 1-{(R)-1-Hydroxy-4-[6-(3-(1-methylindol-2-yl)propoxy)indol-1-yl]-2-butyl}imidazole-4-carboxamide (50.9 mg, 66.2%)

IR (KBr): 3700–3000, 2937, 1660, 1618, 1238, 1086 cm$^{-1}$; NMR (DMSO-d$_6$, δ): 2.05–2.40 (4H, m), 2.96 (2H, t, J=8 Hz), 3.50–4.20 (10H, m), 5.04 (1H, t, J=5 Hz), 6.27 (1H, s), 6.34 (1H, d, J=3 Hz), 6.70 (1H, dd, J=9 Hz, 2 Hz), 6.74 (1H, d, J=3 Hz), 6.85–7.20 (4H, m), 7.29 (1H, brs), 7.35–7.50 (3H, m), 7.70 (1H, s), 7.81 (1H, s); MS: 486 (M+H)$^+$; [α]$_D^{28.0}$=+17.20° (C=0.50, EtOH).

(17) 1-[(R)-1-Hydroxy-4-(5-(3-phenylpropoxy)indol-1-yl)-2-butyl]imidazole-4-carboxamide (51.3 mg, 76.3%)

IR (KBr): 3600–3000, 2937, 2868, 1658, 1599, 1485, 1238, 1151, 1088 cm$^{-1}$; NMR (DMSO-d$_6$, δ): 1.90–2.40 (4H, m), 2.76 (2H, t, J=8 Hz), 3.59 (2H, t, J=5 Hz), 3.80–4.20 (5H, m), 5.03 (1H, t, J=5 Hz), 6.32 (1H, d, J=3 Hz), 6.77 (1H, dd, J=9 Hz, 2 Hz), 6.95–7.40 (10H, m), 7.69 (1H, s), 7.78 (1H, s); MS: 433 (M+H)$^+$.

(18) 1-[(R)-4-(5-Hexyloxyindol-1-yl)-1-hydroxy-2-butyl]imidazole-4-carboxamide (38.2 mg, 92.7%)

IR (KBr): 3600–3000, 2929, 2862, 1658, 1485, 1238, 1151, 1078 cm$^{-1}$; NMR (DMSO-d$_6$, δ): 0.88 (3H, t, J=7 Hz), 1.10–1.85 (8H, m), 2.10–2.40 (2H, m), 3.59 (2H, t, J=5 Hz), 3.80–4.20 (5H, m), 5.04 (1H, t, J=5 Hz), 6.32 (1H, d, J=3 Hz), 6.74 (1H, dd, J=9 Hz, 2 Hz), 6.90–7.40 (5H, m), 7.69 (1H, s), 7.78 (1H, s); MS: 399 (M+H)$^+$; [α]$_D^{28.3}$=+35.90° (C=0.50, EtOH).

(19) 1-[(R)-1-Hydroxy-4-(1-methylindol-3-yl)-2-butyl]imidazole-4-carboxamide (156 mg, 90.4%) as a white Solid.

IR (KBr): 3600–3000, 2939, 2879, 1657, 1593, 1471, 1419, 1242, 1072 cm$^{-1}$; NMR (DMSO-d$_6$, δ): 2.00–2.25 (2H, m), 2.40–2.60 (2H, m), 3.55–3.80 (5H, m), 4.17 (1H, m), 5.00 (1H, t, J=5 Hz), 6.9–7.50 (7H, m), 7.73 (1H, s), 7.77 (1H, s); MS: 313 (M+H)$^+$; [α]$_D^{28.0}$=+22.50° (C=0.50, EtOH).

(20) 1-[(R)-4-(5-Hexyloxy-1-methylindol-3-yl)-1-hydroxy-2-butyl]imidazole-4-carboxamide (38.8 mg, 93.5%)

IR (KBr): 3600–3000, 2931, 2860, 1676, 1622, 1495, 1227, 1057 cm$^{-1}$; NMR (DMSO-d$_6$, δ): 0.88 (3H, t, J=7 Hz), 1.10–1.55 (6H, m), 1.60–1.80 (2H, m), 2.00–2.20 (2H, m), 2.35–2.60 (2H, m), 3.50–3.80 (5H, m), 3.93 (2H, t, J=6 Hz), 4.15 (1H, m), 4.99 (1H, t, J=5 Hz), 6.75 (1H, dd, J=9 Hz, 2 Hz), 6.86 (1H, d, J=2 Hz), 6.90–7.35 (4H, m), 7.72 (1H, s), 7.77 (1H, s); MS: 413 (M+H)$^+$.

(21) 1-[(R)-1-Hydroxy-4-(1-methyl-5-(3-phenylpropoxy)indol-3-yl)-2-butyl]imidazole-4-carboxamide (26.2 mg, 99.8%)

IR (KBr): 3700–3000, 2933, 2866, 1653, 1556, 1493, 1236, 1130, 1074 cm$^{-1}$; NMR (DMSO-d$_6$, δ): 1.90–2.20 (4H, m), 2.30–2.60 (2H, m), 2.77 (2H, t, J=8 Hz), 3.50–3.80 (5H, m), 3.95 (2H, t, J=6 Hz), 4.15 (1H, m), 4.99 (1H, t, J=5 Hz), 6.78 (1H, dd, J=9 Hz, 2 Hz), 6.86 (1H, d, J=2 Hz), 6.90–7.40 (9H, m), 7.73 (1H, s), 7.77 (1H, s); MS: 447 (M+H)$^+$; [α]$_D^{27.2}$=+24.60° (C=0.50, EtOH).

(22) 1-{(R)-4-[5-(3-(4-Chlorophenyl)propoxy)-1-methylindol-3-yl]-1-hydroxy-2-butyl}imidazole-4-carboxamide (228 mg, 70.5%)

IR (KBr): 3600–3000, 2929, 2862, 1658, 1593, 1489, 1232, 1130, 1082 cm$^{-1}$; NMR (DMSO-d$_6$, δ): 1.90–2.25 (4H, m), 2.30–2.60 (2H, m), 2.77 (2H, t, J=8 Hz), 3.55–3.80 (5H, m), 3.94 (2H, t, J=6 Hz), 4.15 (1H, m), 4.99 (1H, t, J=5 Hz), 6.77 (1H, dd, J=9 Hz, 2 Hz), 6.85 (1H, d, J=2 Hz), 6.95–7.45 (8H, m), 7.72 (1H, s), 7.77 (1H, s); MS: 481 (M+H)$^+$ ($^{35}$Cl), 483 (M+H)$^+$ ($^{37}$Cl); [α]$_D^{27.3}$=+21.30° (C=0.50, EtOH).

(23) 1-[(R)-1-Hydroxy-4-(5-hydroxy-1-methylindol-3-yl)-2-butyl]imidazole-4-carboxamide (223 mg, 85.1%)

IR (KBr): 3600–3000, 2947, 2883, 1657, 1593, 1489, 1230, 1136, 1070 cm$^{-1}$; NMR (DMSO-d$_6$, δ): 1.95–2.55 (4H, m), 3.55–3.75 (5H, m), 4.16 (1H, m), 5.00 (1H, t, J=5 Hz), 6.63 (1H, dd, J=9 Hz, 2 Hz), 6.73 (1H, d, J=2 Hz), 6.95 (1H, s), 7.04 (1H, brs), 7.14 (1H, d, J=9 Hz), 7.27 (1H, brs), 7.72 (1H, s), 7.76 (1H, s), 8.64 (1H, brs); MS: 329 (M+H)$^+$; [α]$_D^{24.1}$=+28.70° (C=0.50, EtOH).

(24) 1-[(R)-1-Hydroxy-4-(2-methylindol-1-yl)-2-butyl]imidazole-4-carboxamide (79.5 mg, 99.8%)

NMR (DMSO-d$_6$, δ): 2.05–2.40 (5H, m), 3.55–3.95 (3H, m), 4.05–4.40 (2H, m), 5.11 (1H, t, J=5 Hz), 6.22 (1H, s), 6.90–7.50 (6H, m), 7.81 (1H, s), 7.88 (1H, s); MS: 313 (M+H)$^+$.

EXAMPLE 13

These compounds were prepared by a similar procedure to that of Preparation 21.

(1) 1-[(R)-4-(5-Butoxy-1-methylindol-3-yl)-1-hydroxy-2-butyl]imidazole-4-carboxamide (21.4 mg, 26.1%)

IR (KBr): 3600–3000, 2935, 2870, 1641, 1585, 1481, 1236, 1201, 1078 cm$^{-1}$; NMR (DMSO-d$_6$, δ): 0.94 (3H, t, J=7 Hz), 1.30–1.80 (4H, m), 1.95–2.25 (2H, m), 2.30–2.60 (2H, m), 3.50–3.80 (5H, m), 3.93 (2H, t, J=6 Hz), 4.15 (1H, m), 4.99 (1H, brs), 6.75 (1H, dd, J=9 Hz, 2 Hz), 6.86 (1H, d, J=2 Hz), 6.95–7.40 (4H, m), 7.72 (1H, s), 7.77 (1H, s); MS: 385 (M+H)$^+$.

(2) 1-[(2S,3R)-5-(6-Butoxyindol-1-yl)-2-hydroxy-3-pentyl]imidazole-4-carboxamide (25.5 mg, 49.5%)

IR (KBr): 3600–3000, 2960, 2871, 1662, 1616, 1595, 1248, 1088 cm$^{-1}$; NMR (DMSO-d$_6$, δ): 0.84 (3H, d, J=6 Hz), 0.95 (3H, t, J=7 Hz), 1.35–1.85 (4H, m), 2.10–2.60 (2H, m), 3.65–4.10 (6H, m), 5.10 (1H, brs), 6.33 (1H, d, J=3 Hz), 6.64 (1H, dd, J=9 Hz, 2 Hz), 6.66 (1H, d, J=2 Hz), 7.09 (1H, d, J=3 Hz), 7.10 (1H, brs), 7.28 (1H, brs), 7.38 (1H, d, J=9 Hz), 7.72 (1H, s), 7.80 (1H, s); MS: 385 (M+H)$^+$.

EXAMPLE 14

These compounds were prepared by a similar procedure to that of Preparation 20.

(1) 1-{(2S,3R)-2-Hydroxy-5-[6-(4-phenylbutyrylamino)indol-1-yl]-3-pentyl}imidazole-4-carboxamide (46 mg, 66.8%)

IR (KBr): 3600–3000, 2970, 2935, 1658, 1593, 1491, 1257 cm$^{-1}$; NMR (DMSO-d$_6$, δ): 0.83 (3H, d, J=6 Hz), 1.80–2.05 (2H, m), 2.15–2.60 (4H, m), 2.65 (1H, t, J=8 Hz), 3.70–4.10 (4H, m), 5.12 (1H, d, J=7 Hz), 6.35 (1H, d, J=3 Hz), 6.95–7.55 (10H, m), 7.65–7.90 (3H, m), 9.82 (1H, s); MS: 474 (M+H)$^+$.

(2) 1-{(2S,3R)-2-Hydroxy-5-[6-(3-(1-methylbenzimidazol-2-yl)propionylamino)indol-1-yl]-3-pentyl}imidazole-4-carboxamide (72 mg, 63.1%)

IR (KBr): 3700–3000, 2972, 2935, 1660, 1595, 1483, 1240, 1147, 1095 cm$^{-1}$; NMR (DMSO-d$_6$, δ): 0.82 (3H, d, J=6 Hz), 2.10–2.55 (2H, m), 2.97 (2H, t, J=7 Hz), 3.20 (2H, t, J=7 Hz), 3.60–4.05 (7H, m), 5.12 (1H, d, J=5 Hz), 6.35 (1H, d, J=3 Hz), 6.95–7.60 (9H, m), 7.65–7.90 (3H, m), 10.04 (1H, brs); MS: 514 (M+H)$^+$.

(3) 1-[(2S,3R)-2-Hydroxy-5-(indol-1-yl)-3-pentyl]imidazole-4-carboxamide (22.1 mg, 86.3%)

IR (KBr): 3600–2800, 1658, 1263, 1236, 1088 cm$^{-1}$; NMR (DMSO-d$_6$, δ): 0.84 (3H, d, J=6 Hz), 2.20–2.60 (2H, m), 3.65–4.20 (4H, m), 5.12 (1H, d, J=5 Hz), 6.43 (1H, d, J=3 Hz), 6.90–7.45 (6H, m), 7.54 (1H, d, J=7 Hz), 7.73 (1H, s), 7.80 (1H, s); MS: 313 (M+H)$^+$; [α]$_D^{28.3}$=+28.50° (C=0.50, EtOH).

(4) 1-[(2S,3R)-5-(3-Cyanoindol-1-yl)-2-hydroxy-3-pentyl]imidazole-4-carboxamide (16.7 mg, 29.8%)

IR (Neat): 3700–3000, 2964, 2216, 1651, 1539, 1238, 1090 cm$^{-1}$; NMR (DMSO-d$_6$, δ): 0.84 (3H, d, J=6 Hz), 2.20–2.65 (2H, m), 3.65–4.30 (4H, m), 5.13 (1H, d, J=5 Hz), 7.07 (1H, brs), 7.15–7.85 (7H, m), 8.20 (1H, s).

(5) 1-[(2S,3R)-2-Hydroxy-5-(6-hydroxyindol-1-yl)-3-pentyl]imidazole-4-carboxamide (108 mg, 89.7%)

IR (KBr): 3700–2800, 1657, 1593, 1234, 1088 cm$^{-1}$; NMR (DMSO-d$_6$, δ): 0.84 (3H, d, J=6 Hz), 2.05–2.55 (2H, m), 3.65–4.05 (4H, m), 5.13 (1H, d, J=5 Hz), 6.27 (1H, d, J=3 Hz), 6.55 (1H, dd, J=8 Hz, 2 Hz), 6.60 (1H, d, J=2 Hz), 6.98 (1H, brs), 7.30 (1H, d, J=8 Hz), 7.32 (1H, brs), 7.73 (1H, s), 7.79 (1H, s), 9.00 (1H, brs); MS: 329 (M+H)$^+$.

(6) 1-[(2S,3R)-2-Hydroxy-5-(indazol-1-yl)-3-pentyl]imidazole-4-carboxamide (39.5 mg, 95.9%)

IR (KBr): 3600–3000, 2972, 2929, 1660, 1597, 1417, 1263, 1238, 1120, 1093 cm$^{-1}$; NMR (DMSO-d$_6$, δ): 0.83 (3H, d, J=6 Hz), 2.20–2.70 (2H, m), 3.65–4.00 (2H, m), 4.21 (2H, t, J=7 Hz), 5.11 (1H, brs), 6.90–7.50 (6H, m), 7.60–7.80 (3H, m); MS: 314 (M+H)$^+$; [α]$_D^{22.8}$=+54.80° (C=0.50, EtOH).

(7) 1-[(2S,3R)-2-Hydroxy-5-(1-naphthyl)-3-pentyl]-1,2,4-triazole

NMR (CDCl$_3$, δ): 1.11 (3H, d, J=6 Hz), 2.2–3.1 (5H, m), 4.0–4.3 (2H, m), 7.1–8.2 (9H, m); MS: 282 (M+H)$^+$; [α]$_D^{24}$=+31.0° (c 0.50, EtOH).

(8) 1-[(2S,3R)-2-Hydroxy-5-(1-naphthyl)-3-pentyl]-7-azabenzimidazole

NMR (CDCl$_3$, δ): 1.26 (3H, d, J=6 Hz), 2.4–3.0 (4H, m), 4.2–4.6 (2H, m), 5.03 (1H, brs), 7.1–8.4 (11H, m); MS: 332 (M+H)$^+$; [α]$_D^{25}$=+12.4° (c 0.50, EtOH).

EXAMPLE 15

To an ice cooled solution of 1-[(2S,3R)-2-benzyloxy-5-(6-chloroindol-1-yl)-3-pentyl]imidazole-4-carboxamide (47.9 mg, 0.110 mmol) in chloroform (5 ml) was added trimethylsilyl iodide (42.6 mg, 0.213 mmol). After 3 minutes, the ice bath was removed, and then stirred at room temperature for 3 hours. The reaction was quenched by addition of methanol. This mixture was extracted with ethyl acetate, and the extracts were washed with brine, dried (sodium sulfate) and evaporated in vacuo. The residue was purified by silica gel (1.5 g) chromatography eluting with chloroform/methanol (50:1 to 10:1) to give 1-[(2S,3R)-5-(6-chloroindol-1-yl)-2-hydroxy-3-pentyl]imidazole-4-carboxamide (20.1 mg, 52.7%).

IR (KBr): 3700–3000, 2972, 2933, 2871, 1664, 1593, 1261, 1099 cm$^{-1}$; NMR (DMSO-d$_6$, δ): 0.85 (3H, d, J=6 Hz), 2.20–2.60 (2H, m), 3.60–4.20 (4H, m), 5.14 (1H, brs), 6.20–7.90 (9H, m); MS: 347 (M+H)$^+$ ($^{35}$Cl), 349 (M+H)$^+$ ($^{37}$Cl).

EXAMPLE 16

This compound was prepared by a similar procedure to that of Preparation 23.

1-{(2S,3R)-2-Hydroxy-5-[6-(3-(4-chlorophenyl)propoxy)indol-1-yl]-3-pentyl}imidazole-4-carboxamide (27.2 mg, 41.3%)

IR (KBr): 3600–3000, 2937, 1660, 1616, 1595, 1489, 1248, 1090 cm$^{-1}$; NMR (DMSO-d$_6$, δ): 0.84 (3H, d, J=6 Hz), 1.90–2.55 (4H, m), 2.77 (2H, t, J=8 Hz), 3.65–4.10 (6H, m), 5.11 (1H, brs), 6.33 ((H, d, J=3 Hz), 6.64 (1H, d, J=2 Hz), 6.66 (1H, dd, J=9 Hz, 2 Hz), 7.00–7.50 (8H, m), 7.72 (1H, s), 7.80 (1H, s); MS: 481 (M+H)$^+$.

EXAMPLE 17

These compounds were prepared by a similar procedure to that of Example 15.

(1) 1-[(2S,3R)-2-Hydroxy-5-(2-oxobenzothiazol-3-yl)-3-pentyl]imidazole-4-carboxamide (15.5 mg, 33.4%)

IR (KBr): 3600–3000, 2970, 1662, 1593, 1412, 1331, 1238, 1130 cm$^{-1}$; NMR (DMSO-d$_6$, δ): 0.84 (3H, d, J=6 Hz), 2.05–2.55 (2H, m), 3.45–4.30 (4H, m), 5.14 (1H, d, J=5 Hz), 6.90–7.50 (5H, m), 7.55–7.80 (3H, m); MS: 347 (M+H)$^+$.

(2) 1-[(2S,3R)-2-Hydroxy-5-(2-oxindol-1-yl)-3-pentyl]imidazole-4-carboxamide (15.5 mg, 33.4%)

IR (KBr): 3700–2800, 1695, 1653, 1543, 1238, 1089 cm$^{-1}$; NMR (CDCl$_3$, δ): 1.09 (3H, d, J=6 Hz), 2.05–2.80 (3H, m), 3.40–4.40 (6H, m), 5.47 (1H, brs), 6.65 (1H, d, J=8 Hz), 6.80–7.80 (6H, m); MS: 329 (M+H)$^+$.

EXAMPLE 18

To a stirred solution of oxalyl chloride (0.102 ml) in dichloromethane (4 ml) were added dropwise a solution of dimethyl sulfoxide (0.166 ml) in dichloromethane (2 ml) and then a solution of 1-[(2S,3R)-2-hydroxy-5-(2,3-dichlorophenyl)-3-pentyl]imidazole-4-carboxamide (0.2 g) in dichloromethane (2 ml) at −60° C. under nitrogen atmosphere. The mixture was stirred for 20 minutes and triethylamine (0.487 ml) was added dropwise at the same temperature. The resulting mixture was stirred at −60° C. for 5 minutes and at −20° C. for 30 minutes, then washed with water, dried over anhydrous magnesium sulfate, and evaporated in vacuo to give an oil (0.19 g). Column chromatography (CH$_2$Cl$_2$:MeOH=30:1) over silica gel afforded a pale brown powder of 1-[(R)-2-oxo-5-(2,3-dichlorophenyl)-3-pentyl]imidazole-4-carboxamide (79.4 mg).

NMR (CDCl$_3$, δ): 2.16 (3H, s), 2.1–2.8 (4H, m), 4.64 (1H, dd, J=11, 4 Hz), 5.49 (1H, s), 6.9–7.4 (4H, m), 7.50 (1H, d, J=1 Hz), 7.66 (1H, d, J=1 Hz); MS: 340 (M+H)$^+$.

EXAMPLE 19

A mixture of 1-[(R)-2-oxo-5-(2,3-dichlorophenyl)-3-pentyl]imidazole-4-carboxamide (34 mg), hydroxylamine hydrochloride (7.65 mg) and sodium acetate (9.03 mg) in methanol (1 ml) was stirred at 70° C. for 2 hours. Ethyl acetate and water were added, and the organic layer was separated, washed with aqueous sodium bicarbonate, dried over anhydrous magnesium sulfate, and evaporated in vacuo to give a powder (34 mg). Column chromatography (CH$_2$Cl$_2$:MeOH=20:1) over silica gel afforded a white powder of 1-[(R)-2-(hydroxyimino)-5-(2,3-dichlorophenyl)-3-pentyl]imidazole-4-carboxamide (25.8 mg, E,Z-mixture).

MS: 355 (M+H)$^+$.

EXAMPLE 20

Methyl magnesium bromide (1 M in THF; 0.265 ml) was added dropwise to a stirred solution of 1-[(R)-2-oxo-5-(2,3-dichlorophenyl)-3-pentyl]imidazole-4-carboxamide (30 mg) in THF (1.4 ml) at 2 to 4° C. under nitrogen atmosphere. The mixture was stirred at the same temperature for 4 hours. The reaction was quenched by an addition of aqueous ammonium chloride and the mixture was extracted with ethyl acetate. The extract was washed with brine, dried over anhydrous magnesium sulfate, and evaporated in vacuo to give an oil (29 mg). Column chromatography (CH$_2$Cl$_2$:MeOH=20:1) over silica gel afforded a pale brown powder of 1-[(R)-2-hydroxy-5-(2,3-dichlorophenyl)-2-methyl-3-pentyl]imidazole-4-carboxamide (8.2 mg).

NMR (CDCl$_3$, δ): 1.12 (3H, s), 1.27 (3H, s), 1.62 (1H, s), 2.1–2.7 (4H, m), 3.79 (1H, dd, J=11 Hz, 3 Hz), 5.39 (1H, s), 6.9–7.4 (4H, m), 7.51 (1H, d, J=1 Hz), 7.76 (1H, d, J=1 Hz); MS: 356 (M+H)$^+$.

EXAMPLE 21

A mixture of ethyl 1-[(2S,3R)-2-hydroxy-5-(2,3-dichlorophenyl)-3-pentyl]-1,2,4-triazole-3-carboxylate (11.6 mg) and ammonium hydroxide (28% in water; 0.5 ml) in tetrahydrofuran (3 ml) was heated in a steel sealed tube at 120° C. overnight. The mixture was taken up in dichloromethane, washed with water, dried, and evaporated. The residue was purified by column chromatography on silica gel, eluting with a mixture of dichloromethane and methanol (20:1) to give a white powder of 1-[(2S,3R)-2-hydroxy-5-(2,3-dichlorophenyl)-3-pentyl]-1,2,4-triazole-3-carboxamide (4.2 mg).

NMR (DMSO-d$_6$, δ): 0.87 (3H, d, J=6 Hz), 2.1–2.8 (4H, m), 3.8–4.0 (1H, m), 4.1–4.3 (1H, m), 5.20 (1H, d, J=5 Hz), 7.2–7.6 (4H, m), 7.75 (1H, s), 8.67 (1H, s); MS: 343 (M+H)$^+$.

EXAMPLE 22

These compounds were prepared by a similar procedure to that of Example 21.

(1) N-Methyl-1-[(2S,3R)-2-hydroxy-5-(2,3-dichlorophenyl)-3-pentyl]-1,2,4-triazole-3-carboxamide NMR (CDCl$_3$, δ): 1.14 (3H, d, J=6 Hz), 2.2–2.8 (5H, m), 3.04 (3H, d, J=5 Hz), 4.1–4.3 (2H, m), 6.9–7.4 (4H, m), 8.15 (1H, s); MS: 357 (M+H)$^+$.

(2) 1-[(2S,3R)-2-Hydroxy-5-(2,3-dichlorophenyl)-3-pentyl]-1,2,4-triazole

NMR (CDCl$_3$, δ): 1.16 (3H, d, J=6 Hz), 2.2–2.7 (5H, m), 4.0–4.3 (2H, m), 6.9–7.4 (3H, m), 8.02 (1H, s), 8.15 (1H, s); MS: 300 (M+H)$^+$.

What is claimed is:

1. A compound of formula (I) or a salt thereof:

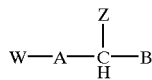
(I)

wherein B is:

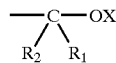

wherein X and $R_1$ are both hydrogen, and $R_2$ is hydrogen or lower alkyl;

wherein X is hydrogen, and $R_1$ and $R_2$ are independently hydrogen or lower alkyl;

A is ethylene;

W is N-containing heterobicyclic group or aryl, each of which may have one or more substituent(s) selected from the group consisting of cyano, hydroxy, halogen, oxo, optionally substituted lower alkoxy, lower alkyl, optionally substituted amino, nitro and —NH—C(O)—$R_3$, wherein $R_3$ is lower alkyl, optionally substituted ar(lower)alkyl, ar(lower)alkylamino, aryl, heterocyclic (lower)alkyl, or heterocyclicthio(lower)alkyl, each of which may have one or more substituent(s); and Z is imidazolyl, which may have one or two substituent(s) selected from the group consisting of carbamoyl, N-substituted carbamoyl, lower alkoxycarbonyl and guanidinocarbonyl, provided that when W is aryl, which may have two or more substituent(s), then Z is imidazolyl which may have one or more substituent(s) and $R_1$ and $R_2$ are both lower alkyl.

2. The compound of claim 1, wherein

W is indolyl, benzothiazolyl, indazolyl, phenyl or naphthyl, each of which may have one or two substituent(s) selected from the group consisting of cyano, hydroxy, halogen, oxo, lower alkoxy, pheny(lower)alkoxy, halophenyl(lower)alkoxy, indolyl(lower)alkoxy which may have lower alkyl, lower alkyl, phenyl(lower)alkylamino, amino, nitro and —NH—C(O)—$R_3$, wherein $R_3$ is lower alkyl, phenyl(lower)alkyl, lower alkylphenyl(lower)alkyl, lower alkoxyphenyl(lower)alkyl, phenyl(lower)alkylamino, phenyl, benzimidazolyl(lower)alkyl which may have lower alkyl, pyridyl(lower)alkyl, benzothiazolylthio(lower)alkyl or indolyl(lower)alkyl which may have one or two oxo; and Z is imidazolyl, which may have one substituent selected from the group consisting of carbamoyl, (lower)alkylcarbamoyl, (lower)alkoxycarbonyl and guanidinocarbonyl.

3. The compound of claim 2, wherein

Z is imidazolyl which may have carbamoyl or guanidinocarbonyl.

4. The compound of claim 3, wherein

W is indolyl which may have one or two substituent(s) selected from the group consisting of cyano, hydroxy, halogen, oxo, lower alkoxy, phenyl(lower)alkoxy, halophenyl(lower)alkoxy, indolyl(lower)alkoxy which may have lower alkyl, lower alkyl, phenyl(lower)alkylamino, amino, nitro, and —NH—C(O)$R_3$, wherein $R_3$ is lower alkyl, phenyl(lower)alkyl, lower alkylphenyl(lower)alkyl, lower alkoxyphenyl(lower)alkyl, phenyl(lower)alkylamino, phenyl, benzimidazolyl(lower)alkyl which may have lower alkyl, pyridyl(lower)alkyl, benzothiazolylthio(lower)alkyl or indolyl(lower)alkyl which may have one or two oxo; benzothiazolyl which may have oxo; indazolyl; phenyl which may have one or two halogen(s); or naphthyl.

5. The compound of claim 4, wherein

W is indolyl which has one or two substituent(s) selected from the group consisting of lower, alkyl, lower alkoxy and halophenyl(lower)alkoxy; or benzothiazolyl which has one oxo; and Z is imidazolyl which has carbamoyl.

6. A process for preparing a compound of the formula (I):

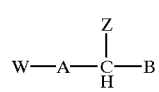
(I)

wherein

B is lower alkanoyl, hydroxyimino(lower)alkyl or

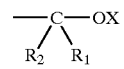

wherein $R_1$ is hydrogen or lower alkyl; $R_2$ is hydrogen or lower alkyl; and

X is hydrogen or hydroxy protective group;

A is lower alkylene;

W is heterocyclic or carbocyclic group, each of which may have one or more substituent(s);

Z is imidazolyl, which may have one or more substituent(s); or a salt thereof, provided that when W is aryl which may have one or more substituent(s), then Z is imidazolyl which may have one or more substituent(s) and B is lower alkanoyl or hydroxyimino(lower)alkyl; or Z is imidazolyl which may have one or more substituent(s) and $R_1$ and $R_2$ are both lower alkyl; comprising:

(1) reacting a compound of the formula:

Z—H or a salt thereof, with a compound of the following formula

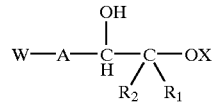

wherein A, $R_1$, $R_2$, W, X and Z are each as defined above, or its reactive derivative at the hydroxy group, or a salt thereof, to give a compound of the following formula:

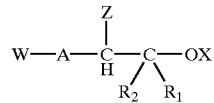

wherein A, $R_1$, $R_2$, W, X and Z are each as defined above, or a salt thereof, or (2) subjecting a compound of the following formula:

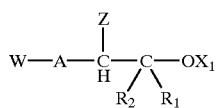

wherein A, $R_1$, $R_2$, W and Z are each as defined above,
$X_1$ is a hydroxy protective group, or a salt thereof to deprotection of the hydroxy protective group to give a compound of the following formula

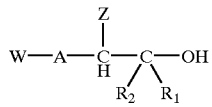

wherein A, $R_1$, $R_2$, W and Z are each as defined above, or a salt thereof, or
(3) subjecting a compound of the following formula:

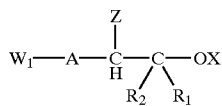

wherein A, $R_1$, $R_2$, X and Z are each as defined above,
$W_1$ is heterocyclic group or carbocyclic group, each of which has nitro, or a salt thereof to reduction reaction of the nitro group to give a compound of the following formula:

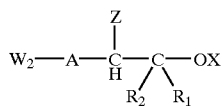

wherein A, $R_1$, $R_2$, X and Z are each as defined above,
$W_2$ is heterocyclic group or carbocyclic group, each of which has amino, or a salt thereof, or
(4) reacting a compound of the following formula:

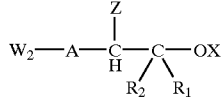

wherein A, $R_1$, $R_2$, $W_2$, X and Z are each as defined above, or its reactive derivative at the amino group, or a salt thereof, with a compound of the following formula:

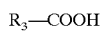

wherein $R_3$ is lower alkyl, optionally substituted ar(lower)alkyl, ar(lower)alkylamino, heterocyclic (lower)alkyl or heterocyclicthio(lower)alkyl, each of which may have one or more substituent(s); or its reactive derivative at carboxy group, or a salt thereof, to give a compound of the following formula:

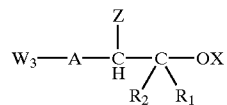

wherein A, $R_1$, $R_2$, X and Z are each as defined above,
$W_3$ is heterocyclic group or carbocyclic group, each of which has a group of the following formula —NH—C(O)—$R_3$ (wherein $R_3$ is as defined above) or a salt thereof, or (5) reacting a compound of the following formula:

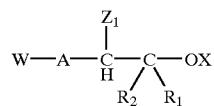

wherein $R_1$, $R_2$, A, W and X are each as defined above, $Z_1$ is imidazolyl, which has carboxy, or its reactive derivative at the carboxy group, or a salt thereof, with guanidine or a salt thereof, to give a compound of the following formula:

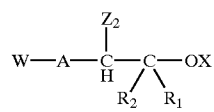

wherein $R_1$, $R_2$, A, W and X are each as defined above, $Z_2$ is imidazolyl, which has guanidinocarbonyl, or a salt thereof, or
(6) subjecting a compound of the following formula:

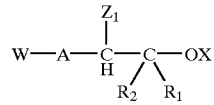

wherein $R_1$, $R_2$, A, W, X and $Z_1$ are each as defined above, or its reactive derivative at the carboxy group, or a salt thereof to amidation to give a compound of the following formula:

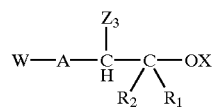

wherein $R_1$, $R_2$, A, W and X are each as defined above,
$Z_3$ is imidazolyl, which has carbamoyl, or a salt thereof,
(7) reacting a compound of the following formula:

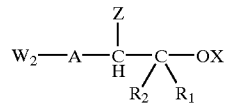

wherein $W_2$, A, X, Z, $R_1$ and $R_2$ are each as defined above, or its reactive derivative at the amino group, or a salt thereof, with a compound of the following formula:

R₄—CHO wherein R₄ is lower alkyl, carbocyclic(lower)alkyl or heterocyclic(lower)alkyl, to give a compound of the following formula:

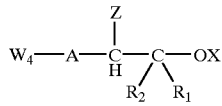

wherein A, X, Z, R₁ and R₂ are each as defined above, and W₄ is carbocyclic or heterocyclic group, each of which has (lower)alkylamino, carbocyclic (lower)alkylamino or heterocyclic(lower) alkylamino, or a salt thereof, or (8) subjecting a compound of the following formula:

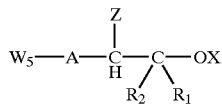

wherein A, X, Z, R₁ and R₂ are each as defined above, and

W₅ is carbocyclic or heterocyclic group, each of which has a hydroxy protective group, or a salt thereof, to deprotection of the hydroxy protective group, and then reacting the deprotected compound with a compound of the following formula:

R₅—Y or R—OR₇ wherein R₅ and R₆ are lower alkyl, heterocyclic (lower)alkyl or carbocyclic(lower)alkyl, R₇ is hydrogen or methanesufonyl, and Y is halogen, to give a compound of the following formula:

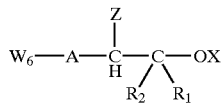

wherein A, X, Z, R₁ and R₂ are each as defined above, and W₆ is heterocyclic or carbocyclic group, each of which has —OR₅ or —OR₆, wherein R₅ and R₆ are each as defined above, or a salt thereof, or (9) subjecting a compound of the following formula:

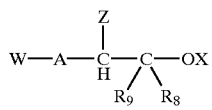

wherein W, A, X and Z are each as defined above, R₈ is hydrogen and R₉ is lower alkyl, or a reactive derivative at the hydroxy group, or a salt thereof, to oxidation reaction to give a compound of the following formula:

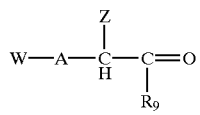

wherein W, A, Z and R₉ are each as defined above, or a salt thereof, or

(10) reacting a compound of the following formula:

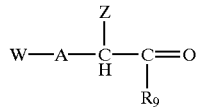

wherein W, A, Z and R₉ are each as defined above, or salt thereof, with hydroxylamine or a salt thereof, to give a compound of the following formula:

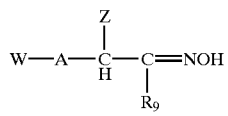

wherein W A, Z and R₉ are each as defined above, or a salt thereof, or

(11) reacting a compound of the following formula:

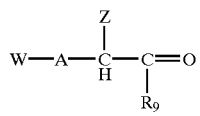

wherein W, A, Z and R₉ are each as defined above, or a salt thereof, with a compound of the following formula:

R₁₀—Y wherein Y is as defined above, and R₁₀ are lower alkyl, to give a compound of the following formula:

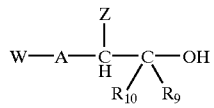

wherein W, A, Z, R and R₁₀ are each as defined above, or a salt thereof.

7. A pharmaceutical composition or medicament comprising a pharmaceutically acceptable carrier or excipient and a compound of the formula (I):

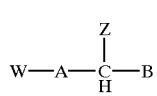

(I)

wherein

B is:

lower alkanoyl, hydroxyimino(lower)alkyl or

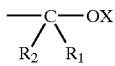

wherein $R_1$ is hydrogen or lower alkyl; $R_2$ is hydrogen or lower alkyl; and X is hydrogen or hydroxy protective group;

A is lower alkylene;

W is heterocyclic or carbocyclic group, each of which may have one or more substituent(s);

Z is imidazolyl, which may have one or more substituent (s); or a salt thereof, provided that when W is aryl which may have one or more substituent(s), then Z is imidazolyl which may have one or more substituent (s) and B is lower alkanoyl or hydroxyimino(lower)alkyl; or Z is imidazolyl which may have one or more substituent (s) and $R_1$ and $R_2$ are both lower alkyl.

8. An adenosine deaminase inhibiting agent comprising a compound of the formula (I):

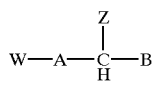

(I)

wherein

B is:
lower alkanoyl,
hydroxyimino(lower)alkyl or

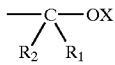

wherein $R_1$ is hydrogen or lower alkyl; $R_2$ is hydrogen or lower alkyl; and X is hydrogen or hydroxy protective group;

A is lower alkylene;

W is heterocyclic or carbocyclic group, each of which may have one or more substituent(s);

Z is imidazolyl, which may have one or more substituent (s); or a salt thereof, provided that when W is aryl which may have one or more substituent(s), then Z is imidazolyl which may have one or more substituent (s) and B is lower alkanoyl or hydroxyimino(lower)alkyl; or Z is imidazolyl which may have one or more substituent (s) and $R_1$ and $R_2$ are both lower alkyl.

9. A method for inhibiting adenosine deaminase in a biological system comprising contacting said biological system with a compound of formula (I):

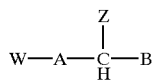

(I)

wherein

B is:
lower alkanoyl, hydroxyimino(lower)alkyl or

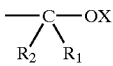

wherein $R_1$ is hydrogen or lower alkyl; $R_2$ is hydrogen or lower alkyl; and X is hydrogen or hydroxy protective group;

A is lower alkylene;

W is heterocyclic or carbocyclic group, each of which may have one or more substituent(s);

Z is imidazolyl, which may have one or more substituent (s); or a salt thereof, provided that when W is aryl which may have one or more substituent(s), then Z is imidazolyl which may have one or more substituent (s) and B is lower alkanoyl or hydroxyimino(lower)alkyl; or Z is imidazolyl which may have one or more substituent (s) and $R_1$ and $R_2$ are both lower alkyl.

10. The method of claim 9, comprising administering an effective amount of the compound of formula (I) to a subject having an autoimmune disease.

11. The method of claim 9 comprising administering an effective amount of the compound of formula (I) to a subject having an inflammatory condition.

12. The method of claim 9 comprising administering an effective amount of the compound of formula (I) to a subject having a transplanted organ or tissue.

13. The method of claim 12, wherein said organ or tissue is a xenograft.

14. The method of claim 12, wherein said organ or tissue is an allograft.

15. The method of claim 9 comprising administering an effective amount of the compound of formula (I) to a subject having leukemia.

16. The method of claim 9 comprising administering an effective amount of the compound of formula (I) to a patient having a disease that arises from, or is aggravated by, insufficient blood flow through a particular organ or a portion thereof.

17. The compound of claim 1 in the form of a solvate.

18. The compound of claim 1 in the form of a hydrate or an ethanolate.

19. The compound of claim 1 in the form of an individual tautomer or an individual isomer.

20. The compound of claim 1 in the form of a mixture of tautomers or a mixture of isomers.

21. A pharmaceutical composition or medicament comprising the compound of claim 1 and a pharmaceutically acceptable carrier or excipient.

22. The composition of claim 7 in the form of a capsule, micro-capsule, tablet, granule, powder or troche.

23. The composition of claim 7 in the form of an aerosol or inhalation.

24. The composition of claim 7 in the form of a suspension, emulsion or syrup.

25. The composition of claim 7 in a form suitable for injection.

26. The composition of claim 7 in the form of a suppository or ointment.

27. A method for the manufacture of a medicament or a pharmaceutical composition comprising admixing a compound of the formula (I):

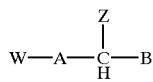

wherein

B is:
  lower alkanoyl,
  hydroxyimino(lower)alkyl or

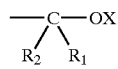

wherein $R_1$ is hydrogen or lower alkyl; $R_2$ is hydrogen or lower alkyl; and X is hydrogen or hydroxy protective group;

A is lower alkylene;

W is heterocyclic or carbocyclic group, each of which may have one or more substituent(s);

Z is imidazolyl, which may have one or more substituent(s); or a salt thereof, provided that when W is aryl which may have one or more substituent(s), then Z is imidazolyl which may have one or more substituent(s) and B is lower alkanoyl or hydroxyimino(lower)alkyl; or Z is imidazolyl which may have one or more substituent(s) and $R_1$ and $R_2$ are both lower alkyl;

and a pharmaceutically acceptable carrier or excipient.

* * * * *